US012241102B2

(12) United States Patent
Mori et al.

(10) Patent No.: US 12,241,102 B2
(45) Date of Patent: Mar. 4, 2025

(54) METHOD FOR SYNTHESIZING BETALAIN PIGMENT

(71) Applicant: Masashi Mori, Ishikawa (JP)

(72) Inventors: Masashi Mori, Ishikawa (JP); Tomohiro Imamura, Ishikawa (JP); Yasuki Higashimura, Ishikawa (JP); Hiroharu Mizukoshi, Ishikawa (JP)

(73) Assignee: Masashi Mori, Ishikawa (JP)

( * ) Notice: Subject to any disclaimer, the term of this patent is extended or adjusted under 35 U.S.C. 154(b) by 900 days.

(21) Appl. No.: 17/285,922

(22) PCT Filed: Oct. 18, 2019

(86) PCT No.: PCT/JP2019/041002
§ 371 (c)(1),
(2) Date: Apr. 16, 2021

(87) PCT Pub. No.: WO2020/080503
PCT Pub. Date: Apr. 23, 2020

(65) Prior Publication Data
US 2021/0324364 A1 Oct. 21, 2021

(30) Foreign Application Priority Data
Oct. 19, 2018 (JP) ............................ JP2018-197998

(51) Int. Cl.

| | |
|---|---|
| *C12N 9/00* | (2006.01) |
| *C12N 9/02* | (2006.01) |
| *C12N 9/04* | (2006.01) |
| *C12P 19/60* | (2006.01) |

(52) U.S. Cl.
CPC ............ *C12N 9/93* (2013.01); *C12N 9/0004* (2013.01); *C12N 9/0006* (2013.01); *C12P 19/60* (2013.01)

(58) Field of Classification Search
None
See application file for complete search history.

(56) References Cited

FOREIGN PATENT DOCUMENTS

| | | |
|---|---|---|
| JP | 2016182044 A | 10/2016 |
| JP | 2019106980 A | 7/2019 |

OTHER PUBLICATIONS

Grewal, Parbir; et al; "Bioproduction of a betalain color palette in *Saccharomyces cerevisiae*" Metabolic Engineering, 45, 180-188, 2018 (Year: 2018).*
International Search Report and Written Opinion issued in corresponding International Patent Application No. PCT/JP2019/041002 (with English translation of International Search Report) dated Nov. 19, 2019 (12 pages).

(Continued)

*Primary Examiner* — David W Berke-Schlessel
(74) *Attorney, Agent, or Firm* — Kilyk & Bowersox, P.L.L.C.

(57) ABSTRACT

It is an object to provide a method of synthesizing amaranthin or gomphrenin-I-glucuronide. Genes each having an amaranthin or gomphrenin-I-glucuronide synthesis ability have been isolated from *quinoa* and the like, and the isolated genes have been used to verify the amaranthin or gomphrenin-I-glucuronide synthesis ability in non-betalain-producing plants.

15 Claims, 23 Drawing Sheets

Specification includes a Sequence Listing.

(56) References Cited

OTHER PUBLICATIONS

Nowacki et al., "Betanin-Enriched Red Beetroot (*Beta vulgaris* L.) Extract Induces Apoptosis and Autophagic Cell Death in MCF-7 Cells," Phytotherapy Research, 2015, vol. 29, Issue 12, pp. 1964-1973 (abstract only)(3 pages).
Sasaki et al., "Amaranthin in feather cockscombs is synthesized via glucuronylation at the cyclo-DOPA glucoside step in the betacyanin biosyntheticpathway," Journal of Plant Research, 2005, vol. 118, pp. 439-442 (abstract only)(8 pages).
Yanuar et al., "Virtual Screening of Indonesian Herbal Database as HIV-1 Protease Inhibitor," Biomedical Informatics, 2014, vol. 10, No. 2, pp. 52-55.

* cited by examiner

Quercetin 3-O-glucoside → Quercetin 3-O-beta-glucosyl-(1->2)-beta-glucoside

Betanin
(Betanidin 5-O-glucoside)

Amaranthin
(Betanidin 5-O-beta-(1->2)-glucuronosyl-beta-glucoside)

| Meas. m/z | Ion Formula | m/z | err [ppm] | err [mDa] |
|---|---|---|---|---|
| 727.182871 | C30H35N2O19 | 727.182853 | 0 | 0 |

| Meas. m/z | Ion Formula | m/z | err [ppm] | err [mDa] |
|---|---|---|---|---|
| 551.150667 | C24H27N2O13 | 551.150765 | 0.2 | 0.1 |
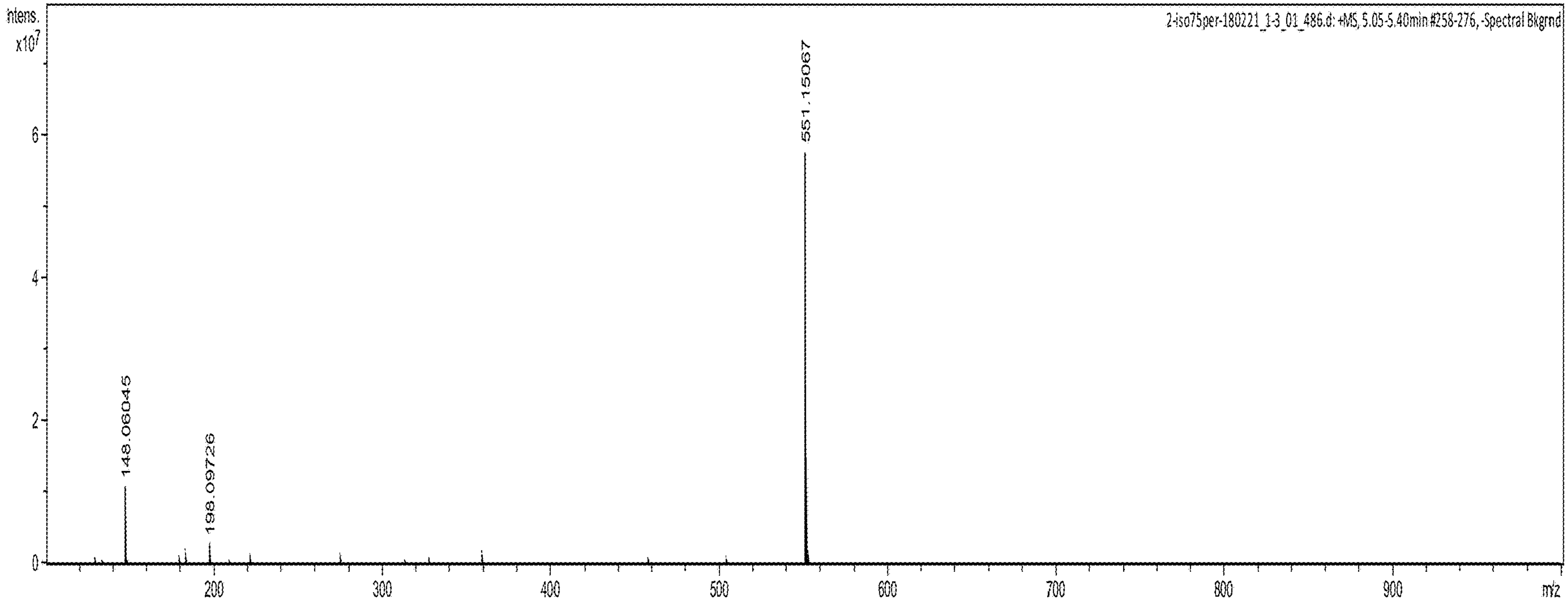
FIG. 7C (con’t)

CqCYP76AD1-1 + CqDODA-1 + DbB6GT+ p19

+CqAmaSy1 -

Bar : 4 cm

DbB6GT : *Dorotheanthus bellidiformis* Betanidin-6-O-glucosyltransferase
(*Dorotheanthus bellidiformis* : LIVINGSTONE DAISY (PLANT)

SEQUENCE LISTING

```
<160> NUMBER OF SEQ ID NOS: 55

<210> SEQ ID NO 1
<211> LENGTH: 1389
<212> TYPE: DNA
<213> ORGANISM: Chenopodium quinoa

<400> SEQUENCE: 1

atgtcacaaa acaaagacaa ccaaattcta aacgttacat tttacccatg gtttgcacta      60

ggccacctta cttcttttct ccgcttagcc aacaaacttg ccgaaagagg tcacaatgtc     120

tcttattttc tcccaccaaa aacacaatca aaattagctt ctcacaacca ctacccaacc     180

caccttacct tcatccccat ccccgtccca cccgtcgaag gcctccctcc tggggccgag     240

acaaccaacg atgtacccgc ctcattaggc cctctcatca tgaccgccat ggacatgaca     300

cgtgacacta tcgagtctca tctagtccgt ctcaaacccg atattgtttt ttacgacttc     360
```

-continued

```
acttgttgga tgcccgaact aggccgaaaa cacgggttta aagccatgca ctatatcaca    420

gcatacatag caagatatgc atatcttgca ccatacaaaa aaataccagg atatcaccct    480

aatgcggatg atctattgac accaccacca gagtttccgt cacaatcaat caggatgctc    540

ccccaagagg ctgagatcat tgcgggtgcc cttaagacac cattcggtct aggaggacta    600

acactagctg agaggctagg tgtttcgttt cgagaatgcg acgcattcgg agttaagact    660

tgtgcggaga tggaagggga gtattgtaaa ttttttgaga aaatatttgg taagccagtg    720

ttactagcag ggccaatggt acctaaacgg ccatcttcgg aacttgataa ttattttgat    780

gattggctaa atagtttcg tacgtctagt gttatatatt gtgcacttgg aagtgaatgc    840

gctctgaatt tgaaccaatt tcaagagctt gttcttggat tggagcttac aggtaggcca    900

tttttggcag cgttaaagcc accaatgaat taccaaacaa tagaatcagc attgccagaa    960

ggacttgcgg aaagaataaa aggcagggga ctaattcatg gggttgggt gcaacagcag    1020

ctcatcttac aacatccttc ggtaggatgt tttattacac attgtggtgc aggatctcta    1080

tccgaagcta tggtaagcga atgtcaagtc gtgctgatgc ctcaagcaat cgaccagttc    1140

atcagtgcgc ggatgatgag cttagagtgg aaggttgggg tcgaagttga gaagagaaag    1200

aattatggtt tgttcaccaa ggaggccgtc cataaggcgg tctccttggt gatggaagaa    1260

gatagtgaag ttgggagaga tgtaagggct aatcatgcta aatggagaga gtttatttta    1320

actgaaggtc ttgaggattc ttatattagt agcttcatac agagtttgca acaattgata    1380

ggatcataa                                                            1389
```

<210> SEQ ID NO 2
<211> LENGTH: 462
<212> TYPE: PRT
<213> ORGANISM: Chenopodium quinoa

<400> SEQUENCE: 2

```
Met Ser Gln Asn Lys Asp Asn Gln Ile Leu Asn Val Thr Phe Tyr Pro
1               5                   10                  15

Trp Phe Ala Leu Gly His Leu Thr Ser Phe Leu Arg Leu Ala Asn Lys
            20                  25                  30

Leu Ala Glu Arg Gly His Asn Val Ser Tyr Phe Leu Pro Pro Lys Thr
        35                  40                  45

Gln Ser Lys Leu Ala Ser His Asn His Tyr Pro Thr His Leu Thr Phe
    50                  55                  60

Ile Pro Ile Pro Val Pro Pro Val Glu Gly Leu Pro Pro Gly Ala Glu
65                  70                  75                  80

Thr Thr Asn Asp Val Pro Ala Ser Leu Gly Pro Leu Ile Met Thr Ala
                85                  90                  95

Met Asp Met Thr Arg Asp Thr Ile Glu Ser His Leu Val Arg Leu Lys
            100                 105                 110

Pro Asp Ile Val Phe Tyr Asp Phe Thr Cys Trp Met Pro Glu Leu Gly
        115                 120                 125

Arg Lys His Gly Phe Lys Ala Met His Tyr Ile Thr Ala Tyr Ile Ala
    130                 135                 140

Arg Tyr Ala Tyr Leu Ala Pro Tyr Lys Lys Ile Pro Gly Tyr His Pro
145                 150                 155                 160

Asn Ala Asp Asp Leu Leu Thr Pro Pro Pro Glu Phe Pro Ser Gln Ser
                165                 170                 175

Ile Arg Met Leu Pro Gln Glu Ala Glu Ile Ile Ala Gly Ala Leu Lys
            180                 185                 190
```

-continued

```
Thr Pro Phe Gly Leu Gly Gly Leu Thr Leu Ala Glu Arg Leu Gly Val
        195                 200                 205

Ser Phe Arg Glu Cys Asp Ala Phe Gly Val Lys Thr Cys Ala Glu Met
    210                 215                 220

Glu Gly Glu Tyr Cys Lys Phe Phe Glu Lys Ile Phe Gly Lys Pro Val
225                 230                 235                 240

Leu Leu Ala Gly Pro Met Val Pro Lys Arg Pro Ser Ser Glu Leu Asp
                245                 250                 255

Asn Tyr Phe Asp Asp Trp Leu Asn Ser Phe Arg Thr Ser Ser Val Ile
            260                 265                 270

Tyr Cys Ala Leu Gly Ser Glu Cys Ala Leu Asn Leu Asn Gln Phe Gln
        275                 280                 285

Glu Leu Val Leu Gly Leu Glu Leu Thr Gly Arg Pro Phe Leu Ala Ala
    290                 295                 300

Leu Lys Pro Pro Met Asn Tyr Gln Thr Ile Glu Ser Ala Leu Pro Glu
305                 310                 315                 320

Gly Leu Ala Glu Arg Ile Lys Gly Arg Gly Leu Ile His Gly Gly Trp
                325                 330                 335

Val Gln Gln Gln Leu Ile Leu Gln His Pro Ser Val Gly Cys Phe Ile
            340                 345                 350

Thr His Cys Gly Ala Gly Ser Leu Ser Glu Ala Met Val Ser Glu Cys
        355                 360                 365

Gln Val Val Leu Met Pro Gln Ala Ile Asp Gln Phe Ile Ser Ala Arg
    370                 375                 380

Met Met Ser Leu Glu Trp Lys Val Gly Val Glu Val Glu Lys Arg Lys
385                 390                 395                 400

Asn Tyr Gly Leu Phe Thr Lys Glu Ala Val His Lys Ala Val Ser Leu
                405                 410                 415

Val Met Glu Glu Asp Ser Glu Val Gly Arg Asp Val Arg Ala Asn His
            420                 425                 430

Ala Lys Trp Arg Glu Phe Ile Leu Thr Glu Gly Leu Glu Asp Ser Tyr
        435                 440                 445

Ile Ser Ser Phe Ile Gln Ser Leu Gln Gln Leu Ile Gly Ser
    450                 455                 460


<210> SEQ ID NO 3
<211> LENGTH: 1389
<212> TYPE: DNA
<213> ORGANISM: Chenopodium quinoa

<400> SEQUENCE: 3

atgtcacaaa acaaagacac ccaaattcta aacgttgcat tttacccatg gtttgcacta      60

ggccacctta cttcttttct ccgcttagcc aacaaactag ccgaaagagg tcacaaagtc     120

tcctatttta tcccaccaaa aacacgatca aagttagctt ctcacaacca ctacccaacc     180

caccttacct tcatccccat ccccgtccca ccggtcgaag gcctccctcc cggggccgag     240

acaaccaacg atgtacccgc ctcatccggc ccactcatca tgaacgccat ggacatgaca     300

cgtgacacca tcgagaccca tctagtccga ctcaaacccg atattgtttt ttacgacttc     360

acttgttgga tgcccgaact agcccgaaaa cacgggttta aagcaataca ctatatcaca     420

gcatacatag caagatatgc atatcttgca ccatacaaaa aaataccagg gtatcaccct     480

aatgcgaatg atctattaac accaccacca gagtttccgt ctcaatcaat caggatgctc     540

ccccaagagg ccgagatcat ggcgggtgcc ggtaagacgc catttggtct agggggacta     600
```

-continued

```
acactggctg agaggctagg tgtttcgttt cgagaatgcg acgcattcgg ggttaagact    660

tgtacggaga tggaagggga gtattgtaag ttttttgaga aaatatttgg taagccagtg    720

ttactagcag ggccaatggt gcctaaaacg ccatcttcga aacttgataa gtattttgat    780

gattggttga atagttttgg taatgctagt gttatatatt gtgcacttgg aagtgaatgt    840

gctctgaaat tgaaccaatt tcaagagctt gttcttggac tagagcttac aggtaggcca    900

tttttggcag ccttaaagcc accaatgaat taccaaacaa tagaatcagc attaccagaa    960

ggatttgcgg aaagaacaaa aagcagggga cttattcatg gtggttgggt gcaacaacaa   1020

ctcatcgtac aacatccttc ggtaggatgt tttataacac attgtggtgc aggatctcta   1080

tccgaagcta tggtaagcga atgtcaagtc gtgttgatgc ctcaagcaat cgaccagttc   1140

atcagtgcgc gaatgatgag cttagagtgg aaggttgggg tcgaagttga gaagagaaag   1200

aatgatggtt tgttcaccaa ggaggccgtc cataaggcgg tctccttggt gatggaagaa   1260

gacagtgaag ttggaagaga tgtaagggct aatcatgcta aatggagaga gtttatatta   1320

actgaaggtc ttgaggattc ttatattagt agcttcatta tgagtttgca acaattgatt   1380

ggatcatga                                                           1389
```

```
<210> SEQ ID NO 4
<211> LENGTH: 462
<212> TYPE: PRT
<213> ORGANISM: Chenopodium quinoa

<400> SEQUENCE: 4

Met Ser Gln Asn Lys Asp Thr Gln Ile Leu Asn Val Ala Phe Tyr Pro
1               5                   10                  15

Trp Phe Ala Leu Gly His Leu Thr Ser Phe Leu Arg Leu Ala Asn Lys
            20                  25                  30

Leu Ala Glu Arg Gly His Lys Val Ser Tyr Phe Ile Pro Pro Lys Thr
        35                  40                  45

Arg Ser Lys Leu Ala Ser His Asn His Tyr Pro Thr His Leu Thr Phe
    50                  55                  60

Ile Pro Ile Pro Val Pro Pro Val Glu Gly Leu Pro Pro Gly Ala Glu
65                  70                  75                  80

Thr Thr Asn Asp Val Pro Ala Ser Ser Gly Pro Leu Ile Met Asn Ala
                85                  90                  95

Met Asp Met Thr Arg Asp Thr Ile Glu Thr His Leu Val Arg Leu Lys
            100                 105                 110

Pro Asp Ile Val Phe Tyr Asp Phe Thr Cys Trp Met Pro Glu Leu Ala
        115                 120                 125

Arg Lys His Gly Phe Lys Ala Ile His Tyr Ile Thr Ala Tyr Ile Ala
    130                 135                 140

Arg Tyr Ala Tyr Leu Ala Pro Tyr Lys Lys Ile Pro Gly Tyr His Pro
145                 150                 155                 160

Asn Ala Asn Asp Leu Leu Thr Pro Pro Pro Glu Phe Pro Ser Gln Ser
                165                 170                 175

Ile Arg Met Leu Pro Gln Glu Ala Glu Ile Met Ala Gly Ala Gly Lys
            180                 185                 190

Thr Pro Phe Gly Leu Gly Gly Leu Thr Leu Ala Glu Arg Leu Gly Val
        195                 200                 205

Ser Phe Arg Glu Cys Asp Ala Phe Gly Val Lys Thr Cys Thr Glu Met
    210                 215                 220
```

-continued

```
Glu Gly Glu Tyr Cys Lys Phe Phe Glu Lys Ile Phe Gly Lys Pro Val
225                 230                 235                 240

Leu Leu Ala Gly Pro Met Val Pro Lys Thr Pro Ser Ser Lys Leu Asp
                245                 250                 255

Lys Tyr Phe Asp Asp Trp Leu Asn Ser Phe Gly Asn Ala Ser Val Ile
            260                 265                 270

Tyr Cys Ala Leu Gly Ser Glu Cys Ala Leu Lys Leu Asn Gln Phe Gln
        275                 280                 285

Glu Leu Val Leu Gly Leu Glu Leu Thr Gly Arg Pro Phe Leu Ala Ala
    290                 295                 300

Leu Lys Pro Pro Met Asn Tyr Gln Thr Ile Glu Ser Ala Leu Pro Glu
305                 310                 315                 320

Gly Phe Ala Glu Arg Thr Lys Ser Arg Gly Leu Ile His Gly Gly Trp
                325                 330                 335

Val Gln Gln Gln Leu Ile Val Gln His Pro Ser Val Gly Cys Phe Ile
            340                 345                 350

Thr His Cys Gly Ala Gly Ser Leu Ser Glu Ala Met Val Ser Glu Cys
        355                 360                 365

Gln Val Val Leu Met Pro Gln Ala Ile Asp Gln Phe Ile Ser Ala Arg
    370                 375                 380

Met Met Ser Leu Glu Trp Lys Val Gly Val Glu Val Glu Lys Arg Lys
385                 390                 395                 400

Asn Asp Gly Leu Phe Thr Lys Glu Ala Val His Lys Ala Val Ser Leu
                405                 410                 415

Val Met Glu Glu Asp Ser Glu Val Gly Arg Asp Val Arg Ala Asn His
            420                 425                 430

Ala Lys Trp Arg Glu Phe Ile Leu Thr Glu Gly Leu Glu Asp Ser Tyr
        435                 440                 445

Ile Ser Ser Phe Ile Met Ser Leu Gln Gln Leu Ile Gly Ser
    450                 455                 460
```

<210> SEQ ID NO 5
<211> LENGTH: 1359
<212> TYPE: DNA
<213> ORGANISM: Beta vulgaris

<400> SEQUENCE: 5

```
atgggtgaaa acaaagaatc gcaagttttg aaggtagcat tctacccttg gtttgcactt      60

ggccacctta cttcattcct tcgcttagcc aacaaacttg ctgaaagagg tcaccaggtc     120

tcatattttc tgccgaagaa tacacaactt aaattagctt ctcaaaacca cttcccagac     180

catctcacct tcatccccat caccgttcca tccgtagacg gccttcctcc tggggccgag     240

acgaccaacg atgtatcctt gtcgggtgcg caccttatca tggctgccat ggacatgact     300

cgtgatacta ttgatgccca tctggccctt ctcaagcccg actttgtttt ctatgatttc     360

gcttattgga tgcctcaact ggctcggaaa catgggatca aatcagtgca ctacatcact     420

ggattaatag caagatatac tctagctatc tcccgtatca caggggcgta tccacccgat     480

ctctcgtccc caatttttca gatgcgtgcc catgagatga aggttatgga gcatataagt     540

gagaagccat tcgcaccagg aggtgtgacg ttgccggaga tgttcaggat atcgttcgaa     600

gaatgtgatg ctgtcggagt caagacttgt aaggaaatgg aaggaattta ctgtgagttt     660

gctgagaaga cgttagataa gcctgtgctt ctcgcagggc ctgttgtccc aaaactacca     720

tcttctaaac ttgatgacta tgttgatgcc tggctaagta cttttggttc tggtactgtt     780
```

-continued

```
atattttgtg ctcttggaag tgaatgtatt cttgaacaaa accagtttca agatattctt    840

cttggactcg agctcacagg taagccattt ttggcggccc tgaagccgcc caagaattgc    900

aaaagtttag agtcgggttt accagaagga ttcagtgaga gagtaagagg aagaggaatg    960

atccatggag gttgggtgca gcaacaactg atcttacaac atccatcagt gggatgtttc   1020

ataactcatt gtggggttgg atctctatca gaagctatgg taagccaatg tcaagttgta   1080

cttatgcctc aagcagtcga tcaattcatg aatgcgaggc agatgagttt agaattgaag   1140

atcggagtta aggtcgagtc cacagagact gatggttttt tcactaggga agccctctgt   1200

aaggcggtct cccttgtgat ggatgaacaa agtgaagttg cgagagaagt gaaggcaaat   1260

catgctaaat ggagagattt tattttaacc gaaggtcttg aggactctta tattagtagc   1320

ttcattcaga gtctacaaca cttgcttcag atgaactga                          1359
```

<210> SEQ ID NO 6
<211> LENGTH: 452
<212> TYPE: PRT
<213> ORGANISM: Beta vulgaris

<400> SEQUENCE: 6

```
Met Gly Glu Asn Lys Glu Ser Gln Val Leu Lys Val Ala Phe Tyr Pro
1               5                   10                  15

Trp Phe Ala Leu Gly His Leu Thr Ser Phe Leu Arg Leu Ala Asn Lys
            20                  25                  30

Leu Ala Glu Arg Gly His Gln Val Ser Tyr Phe Leu Pro Lys Asn Thr
        35                  40                  45

Gln Leu Lys Leu Ala Ser Gln Asn His Phe Pro Asp His Leu Thr Phe
    50                  55                  60

Ile Pro Ile Thr Val Pro Ser Val Asp Gly Leu Pro Pro Gly Ala Glu
65                  70                  75                  80

Thr Thr Asn Asp Val Ser Leu Ser Gly Ala His Leu Ile Met Ala Ala
                85                  90                  95

Met Asp Met Thr Arg Asp Thr Ile Asp Ala His Leu Ala Leu Leu Lys
            100                 105                 110

Pro Asp Phe Val Phe Tyr Asp Phe Ala Tyr Trp Met Pro Gln Leu Ala
        115                 120                 125

Arg Lys His Gly Ile Lys Ser Val His Tyr Ile Thr Gly Leu Ile Ala
    130                 135                 140

Arg Tyr Thr Leu Ala Ile Ser Arg Ile Thr Gly Ala Tyr Pro Pro Asp
145                 150                 155                 160

Leu Ser Ser Pro Ile Phe Gln Met Arg Ala His Glu Met Lys Val Met
                165                 170                 175

Glu His Ile Ser Glu Lys Pro Phe Ala Pro Gly Gly Val Thr Leu Pro
            180                 185                 190

Glu Met Phe Arg Ile Ser Phe Glu Glu Cys Asp Ala Val Gly Val Lys
        195                 200                 205

Thr Cys Lys Glu Met Glu Gly Ile Tyr Cys Glu Phe Ala Glu Lys Thr
    210                 215                 220

Leu Asp Lys Pro Val Leu Leu Ala Gly Pro Val Val Pro Lys Leu Pro
225                 230                 235                 240

Ser Ser Lys Leu Asp Asp Tyr Val Asp Ala Trp Leu Ser Thr Phe Gly
                245                 250                 255

Ser Gly Thr Val Ile Phe Cys Ala Leu Gly Ser Glu Cys Ile Leu Glu
            260                 265                 270
```

-continued

```
Gln Asn Gln Phe Gln Asp Ile Leu Leu Gly Leu Glu Leu Thr Gly Lys
        275                 280                 285

Pro Phe Leu Ala Ala Leu Lys Pro Pro Lys Asn Cys Lys Ser Leu Glu
    290                 295                 300

Ser Gly Leu Pro Glu Gly Phe Ser Glu Arg Val Arg Gly Arg Gly Met
305                 310                 315                 320

Ile His Gly Gly Trp Val Gln Gln Gln Leu Ile Leu Gln His Pro Ser
                325                 330                 335

Val Gly Cys Phe Ile Thr His Cys Gly Val Gly Ser Leu Ser Glu Ala
            340                 345                 350

Met Val Ser Gln Cys Gln Val Val Leu Met Pro Gln Ala Val Asp Gln
        355                 360                 365

Phe Met Asn Ala Arg Gln Met Ser Leu Glu Leu Lys Ile Gly Val Lys
    370                 375                 380

Val Glu Ser Thr Glu Thr Asp Gly Phe Phe Thr Arg Glu Ala Leu Cys
385                 390                 395                 400

Lys Ala Val Ser Leu Val Met Asp Glu Gln Ser Glu Val Ala Arg Glu
                405                 410                 415

Val Lys Ala Asn His Ala Lys Trp Arg Asp Phe Ile Leu Thr Glu Gly
            420                 425                 430

Leu Glu Asp Ser Tyr Ile Ser Ser Phe Ile Gln Ser Leu Gln His Leu
        435                 440                 445

Leu Gln Met Asn
    450


<210> SEQ ID NO 7
<211> LENGTH: 1371
<212> TYPE: DNA
<213> ORGANISM: Amaranthus hypochondriacus

<400> SEQUENCE: 7

atgggttaca aagaagagtc ctctgttatg catatagcat tttacccatg gctagctcta      60

ggccatataa cctccttcct tcgtttagcc aacaaacttg cacaaaaagg tcatactatc     120

tcattcttca tccctaccaa aacccaatcc aaattagctt ctcaaaacca cttccctaac     180

cacctcacct tcgtccccgt cgatatcccg tctatcgacg ggcttcctcc aggggccgag     240

accaccaacg atgtgtcggt ctcggccgca ccccttatca tgtccgctat ggacatgacc     300

cgtgactcta tcgaaaccca attagtccat cttaaacccg attttgtttt ctatgacttt     360

gcgtattgga tgcctgaatt gggtaaaaaa catgggttca aatccgtgca ttacatcaca     420

ggttatatag caagatacgc tgcttttgct gcttacatta cagcacccga ccatactaac     480

actttagacc caccaccagg gctttcttcc ccaatattta agatgcaggc ccatgagtcc     540

cggattctat cagcggtaag taaacggccg tttgggtcaa caggtaaaac gatgactgaa     600

atgtttggta tatcgtttag ggaatgcgat gcgattggag ctaaaacttg tacggaaatg     660

gaaggggaat attatgagtt tgttaaaaag actttaggta agccattgtt gttagccggg     720

cctgttgttc ctattcaacc agcatctaag ttagatgaga aagttgatga atggttaaat     780

ggttttggag ctgaaactgt gatttattgt gcacttggaa gtgaatgtgt tctagaactt     840

tctcagtttc aacagattct tcttggatta gagctaacag gtaggccatt ttttgcagcc     900

ctaaagcccc ccaagaatta tgaaactata gagtcagcct tgccgaaaga gttcgaggag     960

agaataaaag gaaaaggaat cattgatagt ggttgggttc aacaacaact aatattaaaa    1020

catccatcaa taggatgttt tataacacat tgtggagttg gatctctgtc tgaagctatg    1080
```

-continued

```
gtaagccatt gtcaagtggt gtttatgcct caagccgtgg accaattcat caacgcaagg   1140

caaatgagcc ttgagttgaa gatcggggtg gaagttgagt cgcgagagga ggatggtttt   1200

tacaccaagg aggccgtcag taaagcggtc tccttggtga tggatgaaca tagtgaagtt   1260

ggtagagaag taagagctaa acatgctaaa tggagagatt ttattttaaa acaaggtctt   1320

gaggattctt atattactag ctttatcaat agtttacgac aattgcttta a            1371


<210> SEQ ID NO 8
<211> LENGTH: 456
<212> TYPE: PRT
<213> ORGANISM: Amaranthus hypochondriacus

<400> SEQUENCE: 8

Met Gly Tyr Lys Glu Glu Ser Ser Val Met His Ile Ala Phe Tyr Pro
1               5                   10                  15

Trp Leu Ala Leu Gly His Ile Thr Ser Phe Leu Arg Leu Ala Asn Lys
            20                  25                  30

Leu Ala Gln Lys Gly His Thr Ile Ser Phe Phe Ile Pro Thr Lys Thr
        35                  40                  45

Gln Ser Lys Leu Ala Ser Gln Asn His Phe Pro Asn His Leu Thr Phe
    50                  55                  60

Val Pro Val Asp Ile Pro Ser Ile Asp Gly Leu Pro Pro Gly Ala Glu
65                  70                  75                  80

Thr Thr Asn Asp Val Ser Val Ser Ala Ala Pro Leu Ile Met Ser Ala
                85                  90                  95

Met Asp Met Thr Arg Asp Ser Ile Glu Thr Gln Leu Val His Leu Lys
            100                 105                 110

Pro Asp Phe Val Phe Tyr Asp Phe Ala Tyr Trp Met Pro Glu Leu Gly
        115                 120                 125

Lys Lys His Gly Phe Lys Ser Val His Tyr Ile Thr Gly Tyr Ile Ala
    130                 135                 140

Arg Tyr Ala Ala Phe Ala Ala Tyr Ile Thr Ala Pro Asp His Thr Asn
145                 150                 155                 160

Thr Leu Asp Pro Pro Pro Gly Leu Ser Ser Pro Ile Phe Lys Met Gln
                165                 170                 175

Ala His Glu Ser Arg Ile Leu Ser Ala Val Ser Lys Arg Pro Phe Gly
            180                 185                 190

Ser Thr Gly Lys Thr Met Thr Glu Met Phe Gly Ile Ser Phe Arg Glu
        195                 200                 205

Cys Asp Ala Ile Gly Ala Lys Thr Cys Thr Glu Met Glu Gly Glu Tyr
    210                 215                 220

Tyr Glu Phe Val Lys Lys Thr Leu Gly Lys Pro Leu Leu Leu Ala Gly
225                 230                 235                 240

Pro Val Val Pro Ile Gln Pro Ala Ser Lys Leu Asp Glu Lys Val Asp
                245                 250                 255

Glu Trp Leu Asn Gly Phe Gly Ala Glu Thr Val Ile Tyr Cys Ala Leu
            260                 265                 270

Gly Ser Glu Cys Val Leu Glu Leu Ser Gln Phe Gln Gln Ile Leu Leu
        275                 280                 285

Gly Leu Glu Leu Thr Gly Arg Pro Phe Phe Ala Ala Leu Lys Pro Pro
    290                 295                 300

Lys Asn Tyr Glu Thr Ile Glu Ser Ala Leu Pro Lys Glu Phe Glu Glu
305                 310                 315                 320
```

-continued

```
Arg Ile Lys Gly Lys Gly Ile Ile Asp Ser Gly Trp Val Gln Gln Gln
                325                 330                 335

Leu Ile Leu Lys His Pro Ser Ile Gly Cys Phe Ile Thr His Cys Gly
            340                 345                 350

Val Gly Ser Leu Ser Glu Ala Met Val Ser His Cys Gln Val Val Phe
        355                 360                 365

Met Pro Gln Ala Val Asp Gln Phe Ile Asn Ala Arg Gln Met Ser Leu
    370                 375                 380

Glu Leu Lys Ile Gly Val Glu Val Glu Ser Arg Glu Glu Asp Gly Phe
385                 390                 395                 400

Tyr Thr Lys Glu Ala Val Ser Lys Ala Val Ser Leu Val Met Asp Glu
                405                 410                 415

His Ser Glu Val Gly Arg Glu Val Arg Ala Lys His Ala Lys Trp Arg
            420                 425                 430

Asp Phe Ile Leu Lys Gln Gly Leu Glu Asp Ser Tyr Ile Thr Ser Phe
        435                 440                 445

Ile Asn Ser Leu Arg Gln Leu Leu
    450                 455
```

```
<210> SEQ ID NO 9
<211> LENGTH: 1386
<212> TYPE: DNA
<213> ORGANISM: Amaranthus hypochondriacus

<400> SEQUENCE: 9

atgtctcaca acaaagaatc caacccaaat cttcacgtag cattttaccc ttggtttgca     60

ttaggccact taacttcatt ccttcgttta gccaacaaac tagccgaaag aggccttcaa    120

gtctcttatt ttatcccatc caaaacccaa ccaaaactat cccctcacaa ccaccaccct    180

aaccacctta ccttcatacc catcaccgtc ccacacgtcg acggcctccc acccggagcc    240

gagaccacca acgatgtccc cggctcagcc gtacccctca tcatgaccgc aatggactta    300

acccaagaca taattgaggc ccatctagcc caactcaaac ccaactttgt tttctatgac    360

ttcacttatt ggatacctaa actaggccaa aaacttgggt ttaaatctat ccactatttt    420

accgcattta tatcaagata tggttatctt gcaccttaca aaaaggaagg ataccttcca    480

acggcggccg atcttcttcg gccgccacca ggctacccat ccccaataag gatgaagcct    540

tacgaagcca aaattatggc gggcgcaggt aaaaccgcct ttggactagg cgggtttacg    600

ctggccgaga gattagccgt gtcatttata gagtgtgatg catttggggt taagacttgt    660

aaggagatgg aaggtgaaca ttgtaagttt tttgaggatg tttttggtaa gccagtgctt    720

ttagctggac cagttgtgcc taaacttcca tcttctaaac tagatgaaca ttttgatgag    780

tggttaaatg ggtttgatga atctagtgtg attttttgtg cacttggaag tgaatgttct    840

ttggaaatta accaatttca tgagcttctt cttggattag agctcacagg tagaccattt    900

ttggcggctc taaagccgcc aaaaaattac aaaacaatag aatcagcatt accagaaggt    960

tttgcaagca gaactagaga aagaggaata gttcatgaag gttgggtgca acaacaacta   1020

atcttacaac atcgatcagt aggatgtttt ataactcatt gtggagttgg ttctttatcc   1080

gaagctatga taagcaaatg tcaagtagtg atgatacctc aagcaattga tcaattcatc   1140

aatgcaagga tgatgagttt agagtggaag attggagtcg aaatcgagac gagggaggat   1200

gatggttggt tcactaggga ggatgttcac aaggcaatta caatggtgat ggatggagaa   1260

agtgatgttg ggagagaagt tagggctaac catgctaaat ggagggactt tattttaaca   1320
```

```
caaggtgttg aagattctta tattagtagc tttatagaga gtttacaaca attgttaatt   1380

gtatag                                                              1386


<210> SEQ ID NO 10
<211> LENGTH: 461
<212> TYPE: PRT
<213> ORGANISM: Amaranthus hypochondriacus

<400> SEQUENCE: 10

Met Ser His Asn Lys Glu Ser Asn Pro Asn Leu His Val Ala Phe Tyr
1               5                   10                  15

Pro Trp Phe Ala Leu Gly His Leu Thr Ser Phe Leu Arg Leu Ala Asn
            20                  25                  30

Lys Leu Ala Glu Arg Gly Leu Gln Val Ser Tyr Phe Ile Pro Ser Lys
        35                  40                  45

Thr Gln Pro Lys Leu Ser Pro His Asn His His Pro Asn His Leu Thr
    50                  55                  60

Phe Ile Pro Ile Thr Val Pro His Val Asp Gly Leu Pro Pro Gly Ala
65                  70                  75                  80

Glu Thr Thr Asn Asp Val Pro Gly Ser Ala Val Pro Leu Ile Met Thr
                85                  90                  95

Ala Met Asp Leu Thr Gln Asp Ile Ile Glu Ala His Leu Ala Gln Leu
            100                 105                 110

Lys Pro Asn Phe Val Phe Tyr Asp Phe Thr Tyr Trp Ile Pro Lys Leu
        115                 120                 125

Gly Gln Lys Leu Gly Phe Lys Ser Ile His Tyr Phe Thr Ala Phe Ile
    130                 135                 140

Ser Arg Tyr Gly Tyr Leu Ala Pro Tyr Lys Lys Glu Gly Tyr Leu Pro
145                 150                 155                 160

Thr Ala Ala Asp Leu Leu Arg Pro Pro Pro Gly Tyr Pro Ser Pro Ile
                165                 170                 175

Arg Met Lys Pro Tyr Glu Ala Lys Ile Met Ala Gly Ala Gly Lys Thr
            180                 185                 190

Ala Phe Gly Leu Gly Gly Phe Thr Leu Ala Glu Arg Leu Ala Val Ser
        195                 200                 205

Phe Ile Glu Cys Asp Ala Phe Gly Val Lys Thr Cys Lys Glu Met Glu
    210                 215                 220

Gly Glu His Cys Lys Phe Phe Glu Asp Val Phe Gly Lys Pro Val Leu
225                 230                 235                 240

Leu Ala Gly Pro Val Val Pro Lys Leu Pro Ser Ser Lys Leu Asp Glu
                245                 250                 255

His Phe Asp Glu Trp Leu Asn Gly Phe Asp Glu Ser Ser Val Ile Phe
            260                 265                 270

Cys Ala Leu Gly Ser Glu Cys Ser Leu Glu Ile Asn Gln Phe His Glu
        275                 280                 285

Leu Leu Leu Gly Leu Glu Leu Thr Gly Arg Pro Phe Leu Ala Ala Leu
    290                 295                 300

Lys Pro Pro Lys Asn Tyr Lys Thr Ile Glu Ser Ala Leu Pro Glu Gly
305                 310                 315                 320

Phe Ala Ser Arg Thr Arg Glu Arg Gly Ile Val His Glu Gly Trp Val
                325                 330                 335

Gln Gln Gln Leu Ile Leu Gln His Arg Ser Val Gly Cys Phe Ile Thr
            340                 345                 350

His Cys Gly Val Gly Ser Leu Ser Glu Ala Met Ile Ser Lys Cys Gln
```

-continued

```
        355                 360                 365

Val Val Met Ile Pro Gln Ala Ile Asp Gln Phe Ile Asn Ala Arg Met
    370                 375                 380

Met Ser Leu Glu Trp Lys Ile Gly Val Glu Ile Glu Thr Arg Glu Asp
385                 390                 395                 400

Asp Gly Trp Phe Thr Arg Glu Asp Val His Lys Ala Ile Thr Met Val
                405                 410                 415

Met Asp Gly Glu Ser Asp Val Gly Arg Glu Val Arg Ala Asn His Ala
            420                 425                 430

Lys Trp Arg Asp Phe Ile Leu Thr Gln Gly Val Glu Asp Ser Tyr Ile
        435                 440                 445

Ser Ser Phe Ile Glu Ser Leu Gln Gln Leu Leu Ile Val
    450                 455                 460


<210> SEQ ID NO 11
<211> LENGTH: 1263
<212> TYPE: DNA
<213> ORGANISM: Arabidopsis thaliana

<400> SEQUENCE: 11

atgggttaca aagaagagtc ctctgttatg cacatagcat tttacccatg gttagctcta     60

ggccatataa cctccttcct tcgtttagcc aacaaacttg cacaaaaagg tcacactatc    120

tcattcttca tccctaccaa aacccaatcc aaattagctt ctcaaaacca cttccctaac    180

cacctcacct tcatccccgt cgatatcccg tctatcgacg ggcttcctct aggggccgag    240

actaacgatg tgtcggtctc ggccgcaccc cttatcatgt ccgctatgga catgacccgt    300

gaatctatcg aaacccaatt agtccatctt aaacccgact ttgtttttcta tgactttgct    360

tattggatgc ctgaattggg taaaaaacat gggttcaaat ccgtgcatta catcacagga    420

tatttaacaa gatacgctgc ttttgctgct tacattacag cacccgatca tactgacatt    480

ttgggcccac caccagggct ttcttcccca atctttaaga cacgggccca cgaggcccgg    540

gtcggtctat cagcagtgat caaaaaaccg tttggattaa caggtaaaac attgattgaa    600

atgtttggta tatcgtttag ggaatgcgat gcaattggag caaatacttg tatggaaatg    660

gaaggggaat attatgagtt tgtaaacaag actttgggta agccattgtt gttagccggg    720

cctgttgttc caattcaacc agcatctaag ttagatgaga aggttaatga atggttaaat    780

ggttttggtg ctgaaactgt ggtttattgt gcacttggaa agtcagcctt gtcagaagag    840

tttaaggaga gaataaaagg gaaaggaatc attgacggtg gttgggttca gcaacaacta    900

atattgaaac atccatcagt aggatgtttt gtaacacatt gtggaattgg atctctatct    960

gaagctatgg taagccattg tcaaatggtg tttatgcctc aagctgtgga ccagttcatc   1020

aatgcaaggc aaatgagcct tgagttgaag atcggggcgg aagttgagtc gcgagaggag   1080

gatggttttt acaccaagga ggccatcagt aaggcggtct cctcggtgat ggatgaacat   1140

agtgaagttg gtcgagaagt aagagctaac catgctaaat ggagagactt tattttaaaa   1200

caaggtcttg aggactctta tattattagc ttcatcaata gtttacaaca attgcttcat   1260

taa                                                                 1263


<210> SEQ ID NO 12
<211> LENGTH: 420
<212> TYPE: PRT
<213> ORGANISM: Arabidopsis thaliana

<400> SEQUENCE: 12
```

-continued

```
Met Gly Tyr Lys Glu Glu Ser Ser Val Met His Ile Ala Phe Tyr Pro
1               5                   10                  15

Trp Leu Ala Leu Gly His Ile Thr Ser Phe Leu Arg Leu Ala Asn Lys
            20                  25                  30

Leu Ala Gln Lys Gly His Thr Ile Ser Phe Phe Ile Pro Thr Lys Thr
        35                  40                  45

Gln Ser Lys Leu Ala Ser Gln Asn His Phe Pro Asn His Leu Thr Phe
    50                  55                  60

Ile Pro Val Asp Ile Pro Ser Ile Asp Gly Leu Pro Leu Gly Ala Glu
65                  70                  75                  80

Thr Asn Asp Val Ser Val Ser Ala Ala Pro Leu Ile Met Ser Ala Met
                85                  90                  95

Asp Met Thr Arg Glu Ser Ile Glu Thr Gln Leu Val His Leu Lys Pro
            100                 105                 110

Asp Phe Val Phe Tyr Asp Phe Ala Tyr Trp Met Pro Glu Leu Gly Lys
        115                 120                 125

Lys His Gly Phe Lys Ser Val His Tyr Ile Thr Gly Tyr Leu Thr Arg
    130                 135                 140

Tyr Ala Ala Phe Ala Ala Tyr Ile Thr Ala Pro Asp His Thr Asp Ile
145                 150                 155                 160

Leu Gly Pro Pro Pro Gly Leu Ser Ser Pro Ile Phe Lys Thr Arg Ala
                165                 170                 175

His Glu Ala Arg Val Gly Leu Ser Ala Val Ile Lys Lys Pro Phe Gly
            180                 185                 190

Leu Thr Gly Lys Thr Leu Ile Glu Met Phe Gly Ile Ser Phe Arg Glu
        195                 200                 205

Cys Asp Ala Ile Gly Ala Asn Thr Cys Met Glu Met Glu Gly Glu Tyr
    210                 215                 220

Tyr Glu Phe Val Asn Lys Thr Leu Gly Lys Pro Leu Leu Leu Ala Gly
225                 230                 235                 240

Pro Val Val Pro Ile Gln Pro Ala Ser Lys Leu Asp Glu Lys Val Asn
                245                 250                 255

Glu Trp Leu Asn Gly Phe Gly Ala Glu Thr Val Val Tyr Cys Ala Leu
            260                 265                 270

Gly Lys Ser Ala Leu Ser Glu Glu Phe Lys Glu Arg Ile Lys Gly Lys
        275                 280                 285

Gly Ile Ile Asp Gly Gly Trp Val Gln Gln Gln Leu Ile Leu Lys His
    290                 295                 300

Pro Ser Val Gly Cys Phe Val Thr His Cys Gly Ile Gly Ser Leu Ser
305                 310                 315                 320

Glu Ala Met Val Ser His Cys Gln Met Val Phe Met Pro Gln Ala Val
                325                 330                 335

Asp Gln Phe Ile Asn Ala Arg Gln Met Ser Leu Glu Leu Lys Ile Gly
            340                 345                 350

Ala Glu Val Glu Ser Arg Glu Glu Asp Gly Phe Tyr Thr Lys Glu Ala
        355                 360                 365

Ile Ser Lys Ala Val Ser Ser Val Met Asp Glu His Ser Glu Val Gly
    370                 375                 380

Arg Glu Val Arg Ala Asn His Ala Lys Trp Arg Asp Phe Ile Leu Lys
385                 390                 395                 400

Gln Gly Leu Glu Asp Ser Tyr Ile Ile Ser Phe Ile Asn Ser Leu Gln
                405                 410                 415
```

Gln Leu Leu His
420

<210> SEQ ID NO 13
<211> LENGTH: 1494
<212> TYPE: DNA
<213> ORGANISM: Chenopodium quinoa

<400> SEQUENCE: 13
atggatcatg caacactagc aatgatactt gctatttggt ttgttgtttt tcatttcatt 60
aaaatgttat tcactagcca aactaccaaa cttcttcccc ccggtcctaa accattgcca 120
ctaatcggaa acatccttga agttggtgag aaacctcacc agtcatttgc taatcttgct 180
aagattcatg gtccattgat atcattacgt ctaggaagtg tcacaactat tgttgtatcc 240
tcggctgaag tagccaaaga aatgttctta aaaaaagacc acccactttc taaccgcact 300
gttcctaatt ctgtcactgc tggggatcac cataagctga ctatgtcgtg gttgcctgtt 360
tctccaaagt ggcggaactt tagaaaaatc accgccgttc atttactttc tcctcaaaga 420
cttgatgctt gccaaaccct aagacatgcc aaagtgcaac agcttttcca atatgtacaa 480
gaatgtgcac aaaaaggaca agctgttgat attggcaagg cagcatttac aacctccctt 540
aatttgttat caaaattatt cttttcggtc gaattagccc accataaatc ccatacatct 600
caacaattca aagaacttat atggaatatt atggaagata ttggcaaacc taactacgct 660
gattattttc caatcttagg atgcttagac ccatcaggaa ttcgacgtcg attggcgtct 720
aattttgaca agttgattgc agtttttcaa agcataatat gtcaaaggat tggcaacggc 780
caggattctg cttcgacgaa gacgaccgat gatgtgctag acattcttct tgacctccac 840
aaacaaaaag agctcagtat gggcgagata aatcatctgc tcgtggatat ttttgatgct 900
gggactgaca ctacatcaag tacttttgaa tgggtaatgg cagagttaat tcgaaatcct 960
aagatgatgg aaaaagctca agaagaaatt gagcaagtct tgggcaagga tagacaaatt 1020
caagaatcag acattattaa gctaccttac ttacaagcca ttatcaaaga aacattgcgg 1080
ctacacccac caactgtatt tctcttgcct cgtaaagctg atagtgatgt tgaattatat 1140
ggctatgttg tgccgaaaga tgcacaaata cttgttaatt tatgggccat tggaagagac 1200
cctcaagcgt gggtgaaacc tgacgtgttt ttacctgaga ggtttttagg atccgaaatt 1260
gatgtgaaag gaagagattt tggactctta ccttttggag ctggaaggag aatatgcccc 1320
gggatgaatt tggctattag aatgttaact ttgatgttag ctacgcttct tcaattcttc 1380
aattggaagc ttgaagaagg tatgaaagca gaagatctag acatggatga gaaatttggg 1440
attgccttac aaaagactaa acctcttcag attattcccg ttcttaggta ttga 1494

<210> SEQ ID NO 14
<211> LENGTH: 497
<212> TYPE: PRT
<213> ORGANISM: Chenopodium quinoa

<400> SEQUENCE: 14

Met Asp His Ala Thr Leu Ala Met Ile Leu Ala Ile Trp Phe Val Val
1 5 10 15

Phe His Phe Ile Lys Met Leu Phe Thr Ser Gln Thr Thr Lys Leu Leu
20 25 30

Pro Pro Gly Pro Lys Pro Leu Pro Leu Ile Gly Asn Ile Leu Glu Val
35 40 45

Gly Glu Lys Pro His Gln Ser Phe Ala Asn Leu Ala Lys Ile His Gly

-continued

```
    50                  55                  60

Pro Leu Ile Ser Leu Arg Leu Gly Ser Val Thr Thr Ile Val Val Ser
65                  70                  75                  80

Ser Ala Glu Val Ala Lys Glu Met Phe Leu Lys Lys Asp His Pro Leu
                85                  90                  95

Ser Asn Arg Thr Val Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Gln Arg Leu Asp Ala Cys
    130                 135                 140

Gln Thr Leu Arg His Ala Lys Val Gln Gln Leu Phe Gln Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Gln Phe Lys Glu Leu Ile Trp
        195                 200                 205

Asn Ile Met Glu Asp Ile Gly Lys Pro Asn Tyr Ala Asp Tyr Phe Pro
    210                 215                 220

Ile Leu Gly Cys Leu Asp Pro Ser Gly Ile Arg Arg Arg Leu Ala Ser
225                 230                 235                 240

Asn Phe Asp Lys Leu Ile Ala Val Phe Gln Ser Ile Ile Cys Gln Arg
                245                 250                 255

Ile Gly Asn Gly Gln Asp Ser Ala Ser Thr Lys Thr Thr Asp Asp Val
            260                 265                 270

Leu Asp Ile Leu Leu Asp Leu His Lys Gln Lys Glu Leu Ser Met Gly
        275                 280                 285

Glu Ile Asn His Leu Leu Val Asp Ile Phe Asp Ala Gly Thr Asp Thr
    290                 295                 300

Thr Ser Ser Thr Phe Glu Trp Val Met Ala Glu Leu Ile Arg Asn Pro
305                 310                 315                 320

Lys Met Met Glu Lys Ala Gln Glu Glu Ile Glu Gln Val Leu Gly Lys
                325                 330                 335

Asp Arg Gln Ile Gln Glu Ser Asp Ile Ile Lys Leu Pro Tyr Leu Gln
            340                 345                 350

Ala Ile Ile Lys Glu Thr Leu Arg Leu His Pro Pro Thr Val Phe Leu
        355                 360                 365

Leu Pro Arg Lys Ala Asp Ser Asp Val Glu Leu Tyr Gly Tyr Val Val
    370                 375                 380

Pro Lys Asp Ala Gln Ile Leu Val Asn Leu Trp Ala Ile Gly Arg Asp
385                 390                 395                 400

Pro Gln Ala Trp Val Lys Pro Asp Val Phe Leu Pro Glu Arg Phe Leu
                405                 410                 415

Gly Ser Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
        435                 440                 445

Leu Thr Leu Met Leu Ala Thr Leu Leu Gln Phe Phe Asn Trp Lys Leu
    450                 455                 460

Glu Glu Gly Met Lys Ala Glu Asp Leu Asp Met Asp Glu Lys Phe Gly
465                 470                 475                 480
```

Ile Ala Leu Gln Lys Thr Lys Pro Leu Gln Ile Ile Pro Val Leu Arg
485 490 495

Tyr

<210> SEQ ID NO 15
<211> LENGTH: 1476
<212> TYPE: DNA
<213> ORGANISM: Chenopodium quinoa

<400> SEQUENCE: 15
atggagtcat caacaaaaga acaagaacaa caacacataa tcctcctccc atttttagca 60
caaggccatc tccgaccatt cctccacctc gctcaccgcc ttctctctct aacacccttc 120
aatctctctc tcctcactac ccctttaaac gccgctaatc tccgccgtca atccgacaac 180
ttcaacatca accttaacat catcgaactc cccttcacta gcaccgacca cggtctccca 240
cccaacaccg aaaataccga taaactctca ttaacctcca tcatcaaact cttccatgca 300
tccacttcac tcgaacctca tgtacgtgac tacctcacgc gccaccacct gcacgaccca 360
cccgtgtgca taatcttcga cgtgttcttg ggctgggccg ataacgtggc ccgatcagtt 420
gggtccaccg gaatctgctt caacactggt ggggcctacg gtgtcggtgc gtatgtttca 480
atctggagca atctacctca ccggaatgtc ggcgatgatg aggagttttc attggctggt 540
ttcccggaag atcggaaact ccgacgtaat cagcttcatc ggtttttaag gtttgctgat 600
gggtccgatg aatggtcgag gtttttccaa cctcagatta aatcatcctt gaattgttct 660
gggtggttgt gtaattccat cgaggagatt gaaccgttag ggtttcaagt tttaggaat 720 ttcacgaaat ctcctatttg gggaattggt cctttgatta tgacatcttc gaaaaaagat 780
gatgatgaga aggaagaggc ttgtttgagg tggttgaatc aatttgaaaa tgactcagtt 840
ttgtacattt gtttcgggtc acagaataca gtgactccga ttcagatgat ggagttagcg 900
aaaggtttgg aggagagtaa gatcccgttc ttgtgggtga ttcggccgcc attcgggttc 960
gatttcaatg gggagtttaa acccgaatgg ctgcctgaga agtttgagga aagaatgatg 1020
gagaaaaaac aggggatgtt ggtgagagat tgggtgcctc agttggatat tttgaggcat 1080
gaggctactg gtggattttt gagtcattgt ggttggaatt cggtattgga aggtttaaga 1140
gaaggagtgc caatactcgg gtggccgttg gcggccgagc aagcgtataa ttcaaagatg 1200
atggtggagg aaatggggt ggcggtcgag ttgacgaggg ggttggaagg ggaggtgaag 1260
aaagagtggg tgaagagtgt ggtggaaatg gtgttggata gaaaggaggg gagttgtggg 1320
tgggaaatga agaagaaagc tgttgagatt ggggagaaat tgaaggatgc ttggaaaatt 1380
gagggagatt acaaaggatc ttctgttaag gcaatggata attttgtaga gtttatagtt 1440
tcttgtaggg gaaagaaatc taaagaagat gcttga 1476

<210> SEQ ID NO 16
<211> LENGTH: 491
<212> TYPE: PRT
<213> ORGANISM: Chenopodium quinoa

<400> SEQUENCE: 16

Met Glu Ser Ser Thr Lys Glu Gln Glu Gln Gln His Ile Ile Leu Leu
1 5 10 15

Pro Phe Leu Ala Gln Gly His Leu Arg Pro Phe Leu His Leu Ala His
20 25 30

Arg Leu Leu Ser Leu Thr Pro Phe Asn Leu Ser Leu Leu Thr Thr Pro

-continued

```
        35                  40                  45

Leu Asn Ala Ala Asn Leu Arg Arg Gln Ser Asp Asn Phe Asn Ile Asn
    50                  55                  60

Leu Asn Ile Ile Glu Leu Pro Phe Thr Ser Thr Asp His Gly Leu Pro
65                  70                  75                  80

Pro Asn Thr Glu Asn Thr Asp Lys Leu Ser Leu Thr Ser Ile Ile Lys
                85                  90                  95

Leu Phe His Ala Ser Thr Ser Leu Glu Pro His Val Arg Asp Tyr Leu
            100                 105                 110

Thr Arg His His Leu His Asp Pro Pro Val Cys Ile Ile Phe Asp Val
        115                 120                 125

Phe Leu Gly Trp Ala Asp Asn Val Ala Arg Ser Val Gly Ser Thr Gly
    130                 135                 140

Ile Cys Phe Asn Thr Gly Gly Ala Tyr Gly Val Gly Ala Tyr Val Ser
145                 150                 155                 160

Ile Trp Ser Asn Leu Pro His Arg Asn Val Gly Asp Asp Glu Glu Phe
                165                 170                 175

Ser Leu Ala Gly Phe Pro Glu Asp Arg Lys Leu Arg Arg Asn Gln Leu
            180                 185                 190

His Arg Phe Leu Arg Phe Ala Asp Gly Ser Asp Glu Trp Ser Arg Phe
        195                 200                 205

Phe Gln Pro Gln Ile Lys Ser Ser Leu Asn Cys Ser Gly Trp Leu Cys
    210                 215                 220

Asn Ser Ile Glu Glu Ile Glu Pro Leu Gly Phe Gln Val Phe Arg Asn
225                 230                 235                 240

Phe Thr Lys Ser Pro Ile Trp Gly Ile Gly Pro Leu Ile Met Thr Ser
                245                 250                 255

Ser Lys Lys Asp Asp Asp Glu Lys Glu Glu Ala Cys Leu Arg Trp Leu
            260                 265                 270

Asn Gln Phe Glu Asn Asp Ser Val Leu Tyr Ile Cys Phe Gly Ser Gln
        275                 280                 285

Asn Thr Val Thr Pro Ile Gln Met Met Glu Leu Ala Lys Gly Leu Glu
    290                 295                 300

Glu Ser Lys Ile Pro Phe Leu Trp Val Ile Arg Pro Pro Phe Gly Phe
305                 310                 315                 320

Asp Phe Asn Gly Glu Phe Lys Pro Glu Trp Leu Pro Glu Lys Phe Glu
                325                 330                 335

Glu Arg Met Met Glu Lys Lys Gln Gly Met Leu Val Arg Asp Trp Val
            340                 345                 350

Pro Gln Leu Asp Ile Leu Arg His Glu Ala Thr Gly Gly Phe Leu Ser
        355                 360                 365

His Cys Gly Trp Asn Ser Val Leu Glu Gly Leu Arg Glu Gly Val Pro
    370                 375                 380

Ile Leu Gly Trp Pro Leu Ala Ala Glu Gln Ala Tyr Asn Ser Lys Met
385                 390                 395                 400

Met Val Glu Glu Met Gly Val Ala Val Glu Leu Thr Arg Gly Leu Glu
                405                 410                 415

Gly Glu Val Lys Lys Glu Trp Val Lys Ser Val Val Glu Met Val Leu
            420                 425                 430

Asp Arg Lys Glu Gly Ser Cys Gly Trp Glu Met Lys Lys Lys Ala Val
        435                 440                 445

Glu Ile Gly Glu Lys Leu Lys Asp Ala Trp Lys Ile Glu Gly Asp Tyr
    450                 455                 460
```

-continued

```
Lys Gly Ser Ser Val Lys Ala Met Asp Asn Phe Val Glu Phe Ile Val
465                 470                 475                 480

Ser Cys Arg Gly Lys Lys Ser Lys Glu Asp Ala
                485                 490


<210> SEQ ID NO 17
<211> LENGTH: 272
<212> TYPE: PRT
<213> ORGANISM: Chenopodium quinoa

<400> SEQUENCE: 17

Met Lys Met Gly Gly Glu Asn Asn Asn Ile Ile Asn Glu Thr Phe Phe
1               5                   10                  15

Ile Thr His Gly Asn Pro Ile Leu Thr Val Glu Asp Thr His Pro Leu
            20                  25                  30

Arg Pro Phe Phe Glu Thr Trp Thr Lys Lys Ile Phe Ser Lys Lys Pro
        35                  40                  45

Lys Ala Ile Leu Val Ile Ser Gly His Trp Glu Thr Asp His Pro Ala
    50                  55                  60

Val Asn Ala Val His Leu Asn Asp Thr Ile Tyr Asp Phe Asp Asp Tyr
65                  70                  75                  80

Pro Gln Ala Met Tyr Lys Leu Lys Tyr Pro Ala Pro Gly Ser Pro Asp
                85                  90                  95

Leu Ala Ser Arg Ile Glu Glu Ile Leu Lys Lys Ser Gly Phe Asp Thr
            100                 105                 110

Val His Ile Asp Lys Lys Arg Gly Leu Asp His Gly Ala Trp Val Pro
        115                 120                 125

Leu Met Tyr Met Tyr Pro Glu Ala Asp Ile Pro Val Cys Gln Leu Ser
    130                 135                 140

Val Gln Pro Lys Met Asp Gly Thr Tyr His Tyr Asn Leu Gly Arg Ala
145                 150                 155                 160

Leu Ala Pro Leu Lys Asp Glu Gly Val Leu Ile Ile Gly Ser Gly Ser
                165                 170                 175

Ala Thr His Pro Leu Asp Glu Thr Pro His Tyr His Gly Gly Val Ala
            180                 185                 190

Pro Trp Ala Ala Asp Phe Asp Ser Trp Leu Asp Leu Ala Leu Thr Lys
        195                 200                 205

Gly Arg Phe Glu Glu Val Asn Thr Tyr Glu Thr Lys Ala Pro Asn Trp
    210                 215                 220

Glu Leu Ala His Pro Phe Pro Glu His Phe Tyr Pro Leu His Val Val
225                 230                 235                 240

Val Gly Ala Ala Gly Glu Lys Trp Lys Ala Glu Leu Ile His Thr Ser
                245                 250                 255

Trp Asp His Gly Thr Leu Cys His Ala Ser Tyr Lys Phe Thr Ser Thr
            260                 265                 270


<210> SEQ ID NO 18
<211> LENGTH: 819
<212> TYPE: DNA
<213> ORGANISM: Chenopodium quinoa

<400> SEQUENCE: 18

atgaaaatgg gtggggaaaa taacaatata atcaatgaaa ccttcttcat aacccatgga     60

aacccgattt tgaccgtaga agacacacat cccttaaggc cattctttga aacttggact    120

aaaaaaatat tttcgaagaa gccgaaggcg atacttgtga tctccggtca ctgggaaact    180
```

-continued

```
gatcatcctg ctgttaatgc tgttcatctt aatgatacta tctacgattt tgatgactat    240

cctcaagcaa tgtacaagtt gaagtatcca gcaccagggt caccagactt ggctagcaga    300

atagaagaaa ttctgaaaaa gtccgggttc gacacggtgc acattgacaa aaaacgtggg    360

cttgatcatg gtgcatgggt gcctcttatg tacatgtatc cggaggctga cattccggtg    420

tgtcagctct ccgtgcagcc gaaaatggac ggaacgtacc actacaactt gggacgggcg    480

ttggctccgc tgaaagacga aggtgtactc attattggtt ccggaagtgc aacacaccca    540

ttggacgaaa cccctcatta tcatggtggt gttgctcctt gggctgctga ctttgactca    600

tggcttgacc tagctctcac taaaggaagg tttgaagaag tgaatacata tgaaaccaaa    660

gcaccaaact gggaattggc acatccattc ccggagcatt tttatccatt gcacgtcgtc    720

gttggggcgg ctggtgaaaa gtggaaggct gagcttattc atactagttg ggaccatggt    780

accttatgtc atgcctccta caagtttact tccacctaa                           819
```

```
<210> SEQ ID NO 19
<211> LENGTH: 276
<212> TYPE: PRT
<213> ORGANISM: Chenopodium quinoa

<400> SEQUENCE: 19

Met Lys Met Val Val Glu Glu Gly Lys Asn Asn Glu Met Lys Phe Asn
1               5                   10                  15

Glu Thr Phe Phe Ile Thr His Gly Asn Pro Ile Leu Thr Val Glu Asp
            20                  25                  30

Thr His Pro Leu Arg Pro Phe Phe Glu Thr Trp Thr Glu Lys Ile Phe
        35                  40                  45

Ser Lys Lys Pro Lys Ala Ile Leu Val Ile Ser Gly His Trp Glu Thr
    50                  55                  60

Asp His Pro Ala Val Asn Ala Val His Ile Asn Asp Thr Ile Tyr Asp
65                  70                  75                  80

Phe Asp Asp Tyr Pro Glu Ala Met Tyr Lys Phe Lys Tyr Pro Ala Pro
                85                  90                  95

Gly Ser Leu Glu Leu Ala Lys Gly Val Gln Gln Leu Leu Asn Lys Ser
            100                 105                 110

Lys Phe Glu Thr Val His Ile Asp Gln Lys Arg Gly Leu Asp His Gly
        115                 120                 125

Val Trp Val Pro Leu Met Tyr Met Tyr Pro Glu Ala Asp Ile Pro Val
    130                 135                 140

Cys Gln Leu Ser Val Gln Pro Lys Met Asp Gly Thr Tyr His Tyr Asn
145                 150                 155                 160

Leu Gly Arg Ala Leu Ala Pro Leu Arg Asp Glu Gly Ile Leu Ile Ile
                165                 170                 175

Gly Ser Gly Ser Ala Thr His Pro Leu Asp Glu Thr Pro His Tyr His
            180                 185                 190

Gly Gly Val Ala Pro Trp Ala Ala Glu Phe Asp Ser Trp Leu Asp Thr
        195                 200                 205

Ala Leu Thr Asn Gly Arg Ile Glu Glu Val Asn Thr Tyr Glu Thr Lys
    210                 215                 220

Ala Pro Asn Trp Glu Leu Ala His Pro Phe Pro Glu His Phe Tyr Pro
225                 230                 235                 240

Leu His Val Val Val Gly Ala Ala Gly Glu Lys Trp Lys Ala Glu Leu
                245                 250                 255
```

-continued

```
Ile His Thr Ser Trp Asp His Gly Thr Leu Cys His Gly Ala Tyr Lys
            260                 265                 270

Phe Thr Ser Ser
        275


<210> SEQ ID NO 20
<211> LENGTH: 831
<212> TYPE: DNA
<213> ORGANISM: Chenopodium quinoa

<400> SEQUENCE: 20

atgaaaatgg ttgttgaaga gggaaaaaat aacgaaatga aattcaatga aaccttcttc      60

ataacccatg gaaacccaat tttgacagta gaagacacac atcccttaag gccattcttt     120

gaaacttgga ctgaaaaaat attttcgaag aagccgaagg cgatacttgt gatctccggt     180

cactgggaaa ctgatcatcc tgctgttaat gctgttcata tcaatgatac tatctacgat     240

tttgatgact atcctgaagc catgtacaag tttaagtatc cggctcccgg gtctctagaa     300

ttggcaaaag ggtgcaaca actactcaac aaatccaagt tcgaaaccgt gcacattgac     360

caaaaacgtg ggcttgatca tggtgtatgg gtgcctctta tgtacatgta tccggaggcc     420

gacatcccgg tatgtcagct ctccgttcag ccgaaaatgg acggaacata ccactacaac     480

ttgggacgtg cgttagcgcc tctaagagac gaaggtatac tcatcattgg ttccggaagt     540

gcaacacacc ccttagacga aacgcctcat tatcatggtg gtgttgctcc ttgggctgcc     600

gagtttgatt cttggctcga cactgctctc actaatggaa ggattgaaga agtgaataca     660

tatgaaacca aagctccaaa ctgggaatta gcacatccgt tcccggagca tttttatcca     720

ttgcacgtcg tcgttggggc ggctggtgaa aagtggaagg ctgagcttat tcatactagt     780

tgggaccatg gtaccctatg tcatggcgct tacaagttca cttccagtta a              831


<210> SEQ ID NO 21
<211> LENGTH: 270
<212> TYPE: PRT
<213> ORGANISM: Chenopodium quinoa

<400> SEQUENCE: 21

Met Gly Gly Glu Asp Lys Asn Ile Ile Asn Glu Thr Phe Phe Ile Thr
1               5                   10                  15

His Gly Asn Pro Ile Leu Thr Val Glu Asp Thr His Pro Leu Arg Pro
            20                  25                  30

Phe Phe Glu Thr Trp Thr Glu Lys Ile Phe Ser Lys Lys Pro Lys Ala
        35                  40                  45

Ile Leu Val Ile Ser Gly His Trp Glu Thr Asp His Pro Ala Val Asn
    50                  55                  60

Ala Val His Ile Asn Asp Thr Ile Tyr Asp Phe Asp Asp Tyr Pro Glu
65                  70                  75                  80

Ala Met Tyr Lys Val Lys Tyr Pro Ala Pro Gly Ser Pro Asp Leu Ala
                85                  90                  95

Ser Arg Val Glu Glu Ile Leu Lys Lys Ser Gly Phe Asp Thr Val His
            100                 105                 110

Ile Asp Lys Lys Arg Gly Leu Asp His Gly Ala Trp Val Pro Leu Met
        115                 120                 125

Tyr Met Tyr Pro Glu Ala Asp Ile Pro Val Cys Gln Leu Ser Val Gln
    130                 135                 140

Pro Lys Met Asp Gly Thr Tyr His Tyr Asn Leu Gly Arg Ala Leu Ala
145                 150                 155                 160
```

```
Pro Leu Lys Asp Glu Gly Val Leu Ile Ile Gly Ser Gly Ser Ala Thr
                165                 170                 175

His Pro Leu Asp Glu Thr Pro His Tyr His Gly Gly Val Ala Pro Trp
            180                 185                 190

Ala Ala Asp Phe Asp Ser Trp Leu Asp Val Ala Leu Thr Lys Gly Arg
        195                 200                 205

Phe Glu Glu Val Asn Thr Tyr Glu Thr Lys Ala Pro Asn Trp Glu Leu
    210                 215                 220

Ala His Pro Phe Pro Glu His Phe Tyr Pro Leu His Val Val Val Gly
225                 230                 235                 240

Ala Ala Gly Glu Lys Trp Lys Ala Glu Leu Ile His Thr Ser Trp Asp
                245                 250                 255

His Gly Thr Leu Cys His Ala Ser Tyr Lys Phe Thr Ser Thr
            260                 265                 270


<210> SEQ ID NO 22
<211> LENGTH: 813
<212> TYPE: DNA
<213> ORGANISM: Chenopodium quinoa

<400> SEQUENCE: 22

atgggtgggg aagataagaa tataatcaat gaaaccttct tcataaccca tggaaaccca      60

attttaacag tagaagacac gcatccctta aggccattct ttgaaacttg gactgaaaaa     120

atattttcga agaagccgaa ggcgatactt gtgatctccg gtcactggga aactgatcat     180

cctgctgtta atgctgttca tatcaatgat actatctacg attttgatga ttatcctgaa     240

gccatgtaca aagtgaagta tccagctcca gggtcaccag acttggctag ccgagtagaa     300

gaaattctga aaaagtccgg gttcgacacg gtgcacattg acaaaaaacg tgggcttgat     360

catggtgcat gggtgcctct tatgtacatg tatccggagg ctgacattcc ggtatgtcag     420

ctctccgttc agccgaaaat ggacggaacg taccactaca acttggggcg ggcgttggcg     480

ccactgaaag acgaaggtgt tctcattatt ggctccggaa gtgcaacaca ccctttggac     540

gaaacccctc attatcatgg tggtgttgct ccttgggctg ctgactttga ctcgtggctt     600

gacgttgctc tcactaaagg aaggtttgaa gaagtgaata catatgaaac caaagcacca     660

aactgggaat tggcacatcc attcccggag catttttatc cattgcacgt cgtcgtcggg     720

gcggctggtg aaaagtggaa ggctgagctt attcatacta gttgggacca tggtacctta     780

tgtcatgcct cctacaagtt tacttccacc taa                                  813


<210> SEQ ID NO 23
<211> LENGTH: 270
<212> TYPE: PRT
<213> ORGANISM: Chenopodium quinoa

<400> SEQUENCE: 23

Met Gly Gly Glu Asp Asn Asn Met Ile Lys Glu Thr Phe Phe Ile Thr
1               5                   10                  15

His Gly Asn Pro Ile Leu Thr Val Val Asp Thr His Pro Leu Arg Pro
            20                  25                  30

Phe Phe Glu Thr Trp Ser Glu Lys Ile Phe Leu Lys Lys Pro Lys Ala
        35                  40                  45

Ile Leu Val Ile Ser Gly His Trp Glu Thr Asn His Pro Ala Val Asn
    50                  55                  60

Ala Val His Ile Asn Asp Val Ile Tyr Asp Phe Asp Asp Tyr Pro Glu
```

-continued

```
65                  70                  75                  80

Ala Met Tyr Gln Leu Lys Tyr Pro Ala Pro Gly Ser Pro Glu Leu Ala
                85                  90                  95

Ser Ser Val Glu Glu Asn Leu Lys Lys Ser Gly Phe Asp Thr Val His
            100                 105                 110

Ile Asp Lys Lys Arg Gly Leu Asp His Gly Ala Trp Val Pro Leu Met
        115                 120                 125

Tyr Met Tyr Pro Glu Ala Asp Ile Pro Val Cys Gln Leu Ser Val Gln
    130                 135                 140

Pro Lys Leu Asp Gly Thr Tyr His Tyr Asn Leu Gly Arg Ala Leu Ala
145                 150                 155                 160

Pro Leu Lys Asp Glu Gly Val Leu Ile Ile Gly Ser Gly Ser Ala Thr
                165                 170                 175

His Pro Leu Asp Glu Thr Pro His Tyr His Gly Gly Val Ala Pro Trp
            180                 185                 190

Ala Ala Asp Phe Asp Ser Trp Leu Asp Val Ala Leu Thr Lys Gly Arg
        195                 200                 205

Phe Glu Glu Val Asn Thr Tyr Glu Thr Lys Ala Pro Asn Trp Glu Leu
    210                 215                 220

Ala His Pro Phe Pro Glu Asn Phe Tyr Pro Leu His Val Val Ile Gly
225                 230                 235                 240

Ala Ala Gly Glu Met Trp Lys Ala Glu Leu Ile His Asn Ser Trp Asp
                245                 250                 255

His Gly Thr Leu Cys His Gly Ser Tyr Lys Phe Thr Ser Thr
            260                 265                 270
```

<210> SEQ ID NO 24
<211> LENGTH: 813
<212> TYPE: DNA
<213> ORGANISM: Chenopodium quinoa

<400> SEQUENCE: 24

```
atgggaggag aagataacaa tatgatcaaa gaaaccttct tcataaccca tggaaacccg      60

attttgaccg tggtagacac tcatccctta aggccattct ttgaaacatg gagtgaaaaa     120

atatttttga aaaagccgaa ggcgatactt gtgatctctg gtcactggga aactaatcat     180

cctgctgtta atgctgttca tatcaatgat gttatctatg atttcgatga ctatcctgaa     240

gccatgtacc agttgaaata tccagctcca gggtcaccag agttggctag cagtgtagaa     300

gaaaatctga aaaaatccgg gttcgacacg gtgcacattg acaaaaaacg tgggcttgat     360

catggtgcat gggtgcctct tatgtacatg tatccggagg ctgacattcc ggtatgtcag     420

ctctccgttc agccaaaatt ggacggaacg taccactaca acttgggacg ggcgttggcg     480

ccgctgaaag acgaaggtgt actcatcatt ggttccggaa gcgcaacaca ccctttggac     540

gaaacccctc attatcatgg tggtgttgct ccttgggctg ctgactttga ttcttggctt     600

gacgtagctc tcactaaagg aaggtttgaa gaagtgaata catatgaaac caaagcacca     660

aactgggaat tggcacatcc attcccggag aatttttatc cattgcatgt tgtcattggg     720

gcggctggtg aaatgtggaa ggctgagctt attcataata gttgggacca tggtacctta     780

tgtcatggct cctacaagtt tacttccacc taa                                  813
```

<210> SEQ ID NO 25
<211> LENGTH: 272
<212> TYPE: PRT
<213> ORGANISM: Chenopodium quinoa

<400> SEQUENCE: 25

Met Lys Met Ser Gly Glu Asp Asn Ser Met Ile Lys Glu Thr Phe Phe
1               5                   10                  15

Ile Thr His Gly Asn Pro Ile Leu Thr Val Glu Asp Thr His Pro Leu
            20                  25                  30

Arg Pro Phe Phe Glu Thr Trp Arg Glu Lys Ile Phe Thr Met Lys Pro
        35                  40                  45

Lys Ala Ile Leu Val Ile Ser Gly His Trp Glu Thr Asp His Pro Ala
    50                  55                  60

Val Asn Ala Val His Ile Asn Asp Thr Ile Tyr Asp Phe Asp Asp Tyr
65                  70                  75                  80

Pro Gln Ala Met Tyr Lys Leu Lys Tyr Pro Ala Pro Gly Ser Pro Asp
                85                  90                  95

Leu Ala Ser Arg Val Glu Glu Ile Met Lys Lys Ser Gly Phe Asp Thr
            100                 105                 110

Val His Ile Asp Lys Lys Arg Gly Leu Asp His Gly Ala Trp Val Pro
        115                 120                 125

Leu Met Tyr Met Tyr Pro Glu Ala Asp Ile Pro Val Cys Gln Leu Ser
    130                 135                 140

Val Gln Pro Lys Leu Asp Gly Thr Tyr His Tyr Asn Leu Gly Arg Ala
145                 150                 155                 160

Leu Ala Pro Leu Arg Asp Glu Gly Val Leu Ile Ile Gly Ser Gly Ser
                165                 170                 175

Ala Thr His Pro Leu Asp Glu Thr Pro His Tyr His Gly Gly Val Ala
            180                 185                 190

Pro Trp Ala Ala Asp Phe Asp Ser Trp Leu Asp Val Ala Leu Thr Lys
        195                 200                 205

Gly Arg Phe Glu Glu Val Asn Thr Tyr Glu Thr Lys Ala Pro Asn Trp
    210                 215                 220

Glu Leu Ala His Pro Phe Pro Glu His Phe Tyr Pro Leu His Val Val
225                 230                 235                 240

Val Gly Ala Ala Gly Glu Lys Trp Lys Ala Glu Leu Ile His Thr Ser
                245                 250                 255

Trp Asp His Gly Thr Leu Cys His Gly Ser Tyr Lys Phe Thr Ser Thr
            260                 265                 270

<210> SEQ ID NO 26
<211> LENGTH: 819
<212> TYPE: DNA
<213> ORGANISM: Chenopodium quinoa

<400> SEQUENCE: 26
atgaaaatga gtggagaaga taatagcatg atcaaagaaa ctttcttcat aacccatgga 60
aacccgattt tgaccgtaga agacacacat cccttaaggc cattctttga aacatggaga 120
gaaaaaatct ttacgatgaa gccgaaggcg atacttgtga tctctggtca ctgggaaact 180
gatcatcctg ctgttaatgc tgttcatatc aatgatacta tctacgattt cgatgactat 240
cctcaagcca tgtacaagtt gaagtatcca gctccaggat caccagactt ggctagcaga 300
gtagaagaaa ttatgaaaaa atccgggttc gacacagtgc acattgacaa aaaacgtggg 360
cttgatcatg gtgcatgggt gcctcttatg tacatgtatc cggaggctga cataccggta 420
tgtcagctct ccgtccagcc gaagttggac ggaacgtacc actacaactt gggacgagca 480
ttagcgcctc taagagacga aggtgtactc attattggtt ccggaagtgc aacacaccct 540

```
ttggacgaaa cccctcatta tcatggtggt gttgctcctt gggctgctga ctttgactca    600

tggcttgacg tagctctcac taaaggaaga tttgaagaag tgaatacata tgaaaccaaa    660

gcaccaaact gggaattggc acatccattc ccggagcatt tttatccatt gcatgtcgtg    720

gttggggcgg ctggtgaaaa gtggaaggct gagcttattc atactagttg ggaccatggt    780

accttatgtc atggctccta caagtttact tccacctaa                           819


<210> SEQ ID NO 27
<211> LENGTH: 276
<212> TYPE: PRT
<213> ORGANISM: Chenopodium quinoa

<400> SEQUENCE: 27

Met Lys Met Ile Ile Glu Glu Glu Lys Asn Asn Glu Met Asn Phe Asn
1               5                   10                  15

Glu Thr Phe Phe Ile Thr His Gly Asn Pro Ile Leu Thr Val Glu Asp
            20                  25                  30

Thr His Pro Leu Arg Pro Phe Phe Glu Thr Trp Lys Glu Lys Val Phe
        35                  40                  45

Ser Lys Lys Pro Lys Ala Ile Leu Val Ile Ser Gly His Trp Glu Thr
    50                  55                  60

Asp His Pro Ala Val Asn Ala Val His Val Asn Asp Thr Ile Cys Asp
65                  70                  75                  80

Phe Asp Asp Tyr Pro Gln Ala Met Tyr Lys Phe Lys Tyr Pro Ala Pro
                85                  90                  95

Gly Tyr Leu Glu Leu Ala Lys Arg Val Gln Gln Leu Leu Asn Lys Ser
            100                 105                 110

Lys Phe Glu Thr Val His Ile Asp Gln Lys Arg Gly Leu Asp His Gly
        115                 120                 125

Ala Trp Val Pro Leu Met Tyr Met Tyr Pro Glu Ala Asp Ile Pro Val
    130                 135                 140

Cys Gln Leu Ser Val Gln Pro Lys Leu Asp Gly Thr Tyr His Tyr Asn
145                 150                 155                 160

Leu Gly Arg Ala Leu Ala Pro Leu Arg Asp Glu Ser Val Leu Ile Ile
                165                 170                 175

Gly Ser Gly Ser Ala Thr His Pro Leu Asp Glu Thr Pro His Tyr His
            180                 185                 190

Gly Gly Val Ala Pro Trp Ala Ala Glu Phe Asp Ser Trp Leu Asp Thr
        195                 200                 205

Ala Leu Thr Asn Gly Arg Ile Glu Glu Val Asn Thr Tyr Glu Thr Lys
    210                 215                 220

Ala Pro Asn Trp Glu Leu Ala His Pro Phe Pro Glu His Phe Tyr Pro
225                 230                 235                 240

Leu His Val Val Val Gly Ala Ala Gly Glu Lys Trp Lys Ala Glu Leu
                245                 250                 255

Ile His Thr Ser Trp Asp His Gly Thr Leu Cys His Gly Ala Tyr Lys
            260                 265                 270

Phe Thr Ser Ser
        275


<210> SEQ ID NO 28
<211> LENGTH: 831
<212> TYPE: DNA
<213> ORGANISM: Chenopodium quinoa
```

-continued

<400> SEQUENCE: 28

```
atgaaaatga ttattgaaga ggaaaaaaat aacgaaatga atttcaatga aaccttcttc     60

ataacccatg gaaacccgat tttgacagta gaagacacac atcccttaag gccattcttt    120

gaaacatgga aagaaaaagt attttcgaag aagccgaagg cgatacttgt gatctctggt    180

cactgggaaa ctgatcatcc tgctgttaat gctgttcatg tcaatgatac tatctgcgat    240

tttgatgact atcctcaagc catgtacaag tttaagtatc cggctcccgg gtatctagaa    300

ttggcaaaaa gggtgcagca actactcaat aaatccaagt tcgaaaccgt gcacattgac    360

caaaaacgtg ggcttgatca tggtgcatgg gtgcctctta tgtacatgta tccggaggcc    420

gacatcccgg tatgtcagct ctccgttcag ccaaaactgg acggaacata ccactacaac    480

ttgggacgag cattagcgcc tctaagagac gaaagtgtac tcatcattgg ttccggaagt    540

gcaacacacc ccttagacga aacccctcat tatcatggtg gtgttgctcc ttgggctgcc    600

gagtttgatt cttggcttga cactgctctc actaatggaa ggattgaaga agtgaataca    660

tatgaaacca aagctccaaa ctgggaatta gcacatccat tcccagaaca tttttatcca    720

ttgcacgttg tcgtcggggc agctggtgaa aagtggaagg ctgagcttat tcataccagt    780

tgggaccatg gtaccctatg tcatggcgca tacaagttca cttccagtta a             831
```

<210> SEQ ID NO 29
<211> LENGTH: 497
<212> TYPE: PRT
<213> ORGANISM: Chenopodium quinoa

<400> SEQUENCE: 29

```
Met Asp His Ala Thr Leu Ala Met Ile Leu Ala Ile Trp Phe Val Val
1               5                   10                  15

Phe His Phe Ile Lys Met Leu Phe Thr Ser Gln Thr Thr Lys Leu Leu
            20                  25                  30

Pro Pro Gly Pro Lys Pro Leu Pro Leu Ile Gly Asn Ile Leu Glu Val
        35                  40                  45

Gly Glu Lys Pro His Gln Ser Phe Ala Asn Leu Ala Lys Ile His Gly
    50                  55                  60

Pro Leu Ile Ser Leu Arg Leu Gly Ser Val Thr Thr Ile Val Val Ser
65                  70                  75                  80

Ser Ala Glu Val Ala Lys Glu Met Phe Leu Lys Lys Asp His Pro Leu
                85                  90                  95

Ser Asn Arg Thr Val Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125

Lys Ile Thr Ala Val His Leu Leu Ser Pro Gln Arg Leu Asp Ala Cys
    130                 135                 140

Gln Thr Leu Arg His Ala Lys Val Gln Gln Leu Phe Gln Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Gln Phe Lys Glu Leu Ile Trp
        195                 200                 205

Asn Ile Met Glu Asp Ile Gly Lys Pro Asn Tyr Ala Asp Tyr Phe Pro
    210                 215                 220
```

```
Ile Leu Gly Cys Leu Asp Pro Ser Gly Ile Arg Arg Arg Leu Ala Ser
225                 230                 235                 240

Asn Phe Asp Lys Leu Ile Ala Val Phe Gln Ser Ile Ile Cys Gln Arg
                245                 250                 255

Ile Gly Asn Gly Gln Asp Ser Ala Ser Thr Lys Thr Thr Asp Asp Val
            260                 265                 270

Leu Asp Ile Leu Leu Asp Leu His Lys Gln Lys Glu Leu Ser Met Gly
        275                 280                 285

Glu Ile Asn His Leu Leu Val Asp Ile Phe Asp Ala Gly Thr Asp Thr
    290                 295                 300

Thr Ser Ser Thr Phe Glu Trp Val Met Ala Glu Leu Ile Arg Asn Pro
305                 310                 315                 320

Lys Met Met Glu Lys Ala Gln Glu Glu Ile Glu Gln Val Leu Gly Lys
                325                 330                 335

Asp Arg Gln Ile Gln Glu Ser Asp Ile Ile Lys Leu Pro Tyr Leu Gln
            340                 345                 350

Ala Ile Ile Lys Glu Thr Leu Arg Leu His Pro Pro Thr Val Phe Leu
        355                 360                 365

Leu Pro Arg Lys Ala Asp Ser Asp Val Glu Leu Tyr Gly Tyr Val Val
    370                 375                 380

Pro Lys Asp Ala Gln Ile Leu Val Asn Leu Trp Ala Ile Gly Arg Asp
385                 390                 395                 400

Pro Gln Ala Trp Val Lys Pro Asp Val Phe Leu Pro Glu Arg Phe Leu
                405                 410                 415

Gly Ser Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
        435                 440                 445

Leu Thr Leu Met Leu Ala Thr Leu Leu Gln Phe Phe Asn Trp Lys Leu
    450                 455                 460

Glu Glu Gly Met Lys Ala Glu Asp Leu Asp Met Asp Glu Lys Phe Gly
465                 470                 475                 480

Ile Ala Leu Gln Lys Thr Lys Pro Leu Gln Ile Ile Pro Val Leu Arg
                485                 490                 495

Tyr
```

<210> SEQ ID NO 30
<211> LENGTH: 1494
<212> TYPE: DNA
<213> ORGANISM: Chenopodium quinoa

<400> SEQUENCE: 30

```
atggatcatg caacactagc aatgatactt gctatttggt ttgttgtttt tcatttcatt      60

aaaatgttat tcactagcca aactaccaaa cttcttcccc ccggtcctaa accattgcca     120

ctaatcggaa acatccttga agttggtgag aaacctcacc agtcatttgc taatcttgct     180

aagattcatg gtccattgat atcattacgt ctaggaagtg tcacaactat tgttgtatcc     240

tcggctgaag tagccaaaga aatgttctta aaaaaagacc acccactttc taaccgcact     300

gttcctaatt ctgtcactgc tggggatcac cataagctga ctatgtcgtg gttgcctgtt     360

tctccaaagt ggcggaactt tagaaaaatc accgccgttc atttactttc tcctcaaaga     420

cttgatgctt gccaaaccct aagacatgcc aaagtgcaac agcttttcca atatgtacaa     480

gaatgtgcac aaaaaggaca agctgttgat attggcaagg cagcatttac aacctccctt     540
```

```
aatttgttat caaaattatt cttttcggtc gaattagccc accataaatc ccatacatct    600

caacaattca aagaacttat atggaatatt atggaagata ttggcaaacc taactacgct    660

gattattttc caatcttagg atgcttagac ccatcaggaa ttcgacgtcg attggcgtct    720

aattttgaca agttgattgc agtttttcaa agcataatat gtcaaaggat tggcaacggc    780

caggattctg cttcgacgaa gacgaccgat gatgtgctag acattcttct tgacctccac    840

aaacaaaaag agctcagtat gggcgagata aatcatctgc tcgtggatat ttttgatgct    900

gggactgaca ctacatcaag tacttttgaa tgggtaatgg cagagttaat tcgaaatcct    960

aagatgatgg aaaaagctca agaagaaatt gagcaagtct tgggcaagga tagacaaatt   1020

caagaatcag acattattaa gctaccttac ttacaagcca ttatcaaaga aacattgcgg   1080

ctacacccac caactgtatt tctcttgcct cgtaaagctg atagtgatgt tgaattatat   1140

ggctatgttg tgccgaaaga tgcacaaata cttgttaatt tatgggccat tggaagagac   1200

cctcaagcgt gggtgaaacc tgacgtgttt ttacctgaga ggtttttagg atccgaaatt   1260

gatgtgaaag gaagagattt tggactctta ccttttggag ctggaaggag aatatgcccc   1320

gggatgaatt tggctattag aatgttaact ttgatgttag ctacgcttct tcaattcttc   1380

aattggaagc ttgaagaagg tatgaaagca gaagatctag acatggatga gaaatttggg   1440

attgccttac aaaagactaa acctcttcag attattcccg ttcttaggta ttga         1494
```

<210> SEQ ID NO 31
<211> LENGTH: 491
<212> TYPE: PRT
<213> ORGANISM: Chenopodium quinoa

<400> SEQUENCE: 31

```
Met Glu Ser Ser Thr Lys Glu Gln Glu Gln Gln His Ile Ile Leu Leu
1               5                   10                  15

Pro Phe Leu Ala Gln Gly His Leu Arg Pro Phe Leu His Leu Ala His
            20                  25                  30

Arg Leu Leu Ser Leu Thr Pro Phe Asn Leu Ser Leu Leu Thr Thr Pro
        35                  40                  45

Leu Asn Ala Ala Asn Leu Arg Arg Gln Ser Asp Asn Phe Asn Ile Asn
    50                  55                  60

Leu Asn Ile Ile Glu Leu Pro Phe Thr Ser Thr Asp His Gly Leu Pro
65                  70                  75                  80

Pro Asn Thr Glu Asn Thr Asp Lys Leu Ser Leu Thr Ser Ile Ile Lys
                85                  90                  95

Leu Phe His Ala Ser Thr Ser Leu Glu Pro His Val Arg Asp Tyr Leu
            100                 105                 110

Thr Arg His His Leu His Asp Pro Pro Val Cys Ile Ile Phe Asp Val
        115                 120                 125

Phe Leu Gly Trp Ala Asp Asn Val Ala Arg Ser Val Gly Ser Thr Gly
    130                 135                 140

Ile Cys Phe Asn Thr Gly Gly Ala Tyr Gly Val Gly Ala Tyr Val Ser
145                 150                 155                 160

Ile Trp Ser Asn Leu Pro His Arg Asn Val Gly Asp Asp Glu Glu Phe
                165                 170                 175

Ser Leu Ala Gly Phe Pro Glu Asp Arg Lys Leu Arg Arg Asn Gln Leu
            180                 185                 190

His Arg Phe Leu Arg Phe Ala Asp Gly Ser Asp Glu Trp Ser Arg Phe
        195                 200                 205
```

```
Phe Gln Pro Gln Ile Lys Ser Ser Leu Asn Cys Ser Gly Trp Leu Cys
    210                 215                 220

Asn Ser Ile Glu Glu Ile Glu Pro Leu Gly Phe Gln Val Phe Arg Asn
225                 230                 235                 240

Phe Thr Lys Ser Pro Ile Trp Gly Ile Gly Pro Leu Ile Met Thr Ser
                245                 250                 255

Ser Lys Lys Asp Asp Asp Glu Lys Glu Glu Ala Cys Leu Arg Trp Leu
            260                 265                 270

Asn Gln Phe Glu Asn Asp Ser Val Leu Tyr Ile Cys Phe Gly Ser Gln
        275                 280                 285

Asn Thr Val Thr Pro Ile Gln Met Met Glu Leu Ala Lys Gly Leu Glu
    290                 295                 300

Glu Ser Lys Ile Pro Phe Leu Trp Val Ile Arg Pro Pro Phe Gly Phe
305                 310                 315                 320

Asp Phe Asn Gly Glu Phe Lys Pro Glu Trp Leu Pro Glu Lys Phe Glu
                325                 330                 335

Glu Arg Met Met Glu Lys Lys Gln Gly Met Leu Val Arg Asp Trp Val
            340                 345                 350

Pro Gln Leu Asp Ile Leu Arg His Glu Ala Thr Gly Gly Phe Leu Ser
        355                 360                 365

His Cys Gly Trp Asn Ser Val Leu Glu Gly Leu Arg Glu Gly Val Pro
    370                 375                 380

Ile Leu Gly Trp Pro Leu Ala Ala Glu Gln Ala Tyr Asn Ser Lys Met
385                 390                 395                 400

Met Val Glu Glu Met Gly Val Ala Val Glu Leu Thr Arg Gly Leu Glu
                405                 410                 415

Gly Glu Val Lys Lys Glu Trp Val Lys Ser Val Val Glu Met Val Leu
            420                 425                 430

Asp Arg Lys Glu Gly Ser Cys Gly Trp Glu Met Lys Lys Lys Ala Val
        435                 440                 445

Glu Ile Gly Glu Lys Leu Lys Asp Ala Trp Lys Ile Glu Gly Asp Tyr
    450                 455                 460

Lys Gly Ser Ser Val Lys Ala Met Asp Asn Phe Val Glu Phe Ile Val
465                 470                 475                 480

Ser Cys Arg Gly Lys Lys Ser Lys Glu Asp Ala
                485                 490


<210> SEQ ID NO 32
<211> LENGTH: 1476
<212> TYPE: DNA
<213> ORGANISM: Chenopodium quinoa

<400> SEQUENCE: 32

atggagtcat caacaaaaga acaagaacaa caacacataa tcctcctccc atttttagca     60

caaggccatc tccgaccatt cctccacctc gctcaccgcc ttctctctct aacacccttc    120

aatctctctc tcctcactac ccctttaaac gccgctaatc tccgccgtca atccgacaac    180

ttcaacatca accttaacat catcgaactc cccttcacta gcaccgacca cggtctccca    240

cccaacaccg aaaataccga taaactctca ttaacctcca tcatcaaact cttccatgca    300

tccacttcac tcgaacctca tgtacgtgac tacctcacgc gccaccacct gcacgaccca    360

cccgtgtgca taatcttcga cgtgttcttg ggctgggccg ataacgtggc ccgatcagtt    420

gggtccaccg gaatctgctt caacactggt ggggcctacg gtgtcggtgc gtatgtttca    480
```

-continued

```
atctggagca atctacctca ccggaatgtc ggcgatgatg aggagttttc attggctggt    540

ttcccggaag atcggaaact ccgacgtaat cagcttcatc ggtttttaag gtttgctgat    600

gggtccgatg aatggtcgag gtttttccaa cctcagatta aatcatcctt gaattgttct    660

gggtggttgt gtaattccat cgaggagatt gaaccgttag ggtttcaagt ttttaggaat    720

ttcacgaaat ctcctatttg gggaattggt cctttgatta tgacatcttc gaaaaaagat    780

gatgatgaga aggaagaggc ttgtttgagg tggttgaatc aatttgaaaa tgactcagtt    840

ttgtacattt gtttcgggtc acagaataca gtgactccga ttcagatgat ggagttagcg    900

aaaggtttgg aggagagtaa gatcccgttc ttgtgggtga ttcggccgcc attcgggttc    960

gatttcaatg gggagtttaa acccgaatgg ctgcctgaga agtttgagga aagaatgatg   1020

gagaaaaaac aggggatgtt ggtgagagat tgggtgcctc agttggatat tttgaggcat   1080

gaggctactg gtggattttt gagtcattgt ggttggaatt cggtattgga aggtttaaga   1140

gaaggagtgc caatactcgg gtggccgttg gcggccgagc aagcgtataa ttcaaagatg   1200

atggtggagg aaatgggggt ggcggtcgag ttgacgaggg ggttggaagg ggaggtgaag   1260

aaagagtggg tgaagagtgt ggtggaaatg gtgttggata gaaaggaggg gagttgtggg   1320

tgggaaatga agaagaaagc tgttgagatt ggggagaaat tgaaggatgc ttggaaaatt   1380

gagggagatt acaaaggatc ttctgttaag gcaatggata attttgtaga gtttatagtt   1440

tcttgtaggg gaaagaaatc taaagaagat gcttga                             1476
```

<210> SEQ ID NO 33
<211> LENGTH: 48
<212> TYPE: PRT
<213> ORGANISM: Chenopodium quinoa
<220> FEATURE:
<221> NAME/KEY: misc_feature
<222> LOCATION: (19)..(19)
<223> OTHER INFORMATION: Xaa stands for Asp or Glu
<220> FEATURE:
<221> NAME/KEY: misc_feature
<222> LOCATION: (26)..(26)
<223> OTHER INFORMATION: Xaa stands for Leu, Val or Thr
<220> FEATURE:
<221> NAME/KEY: misc_feature
<222> LOCATION: (30)..(30)
<223> OTHER INFORMATION: Xaa stands for Lys or Asn
<220> FEATURE:
<221> NAME/KEY: misc_feature
<222> LOCATION: (33)..(33)
<223> OTHER INFORMATION: Xaa stands for Phe or Ile

<400> SEQUENCE: 33

```
His Pro Leu Asp Glu Thr Pro His Tyr His Gly Gly Val Ala Pro Trp
1               5                   10                  15

Ala Ala Xaa Phe Asp Ser Trp Leu Asp Xaa Ala Leu Thr Xaa Gly Arg
            20                  25                  30

Xaa Glu Glu Val Asn Thr Tyr Glu Thr Lys Ala Pro Asn Trp Glu Leu
        35                  40                  45
```

<210> SEQ ID NO 34
<211> LENGTH: 267
<212> TYPE: PRT
<213> ORGANISM: Mirabilis jalapa

<400> SEQUENCE: 34

```
Met Lys Gly Thr Tyr Tyr Ile Asn His Gly Asp Pro Leu Met Tyr Leu
1               5                   10                  15

Lys Lys His Ile Lys Leu Arg Gln Phe Leu Glu Gly Trp Gln Glu Asn
```

```
        20                  25                  30

Val Val Ile Glu Lys Pro Lys Ser Ile Leu Ile Ile Ser Ala His Trp
        35                  40                  45

Asp Thr Asn Val Pro Thr Val Asn Phe Val Glu His Cys Asp Thr Ile
    50                  55                  60

His Asp Phe Asp Asp Tyr Pro Asp Pro Leu Tyr Gln Ile Gln Tyr Arg
65                  70                  75                  80

Ala Pro Gly Ala Pro Asn Leu Ala Lys Lys Val Glu Glu Leu Leu Lys
                85                  90                  95

Glu Ser Gly Met Glu Cys Glu Ile Asp Thr Lys Arg Gly Leu Asp His
            100                 105                 110

Ala Ala Trp Phe Pro Leu Met Phe Met Tyr Pro Glu Ala Asn Ile Pro
        115                 120                 125

Ile Cys Glu Leu Ser Val Gln Pro Ser Lys Asp Gly Ile His His Tyr
    130                 135                 140

Asn Val Gly Lys Ala Leu Ser Pro Leu Leu Gln Gln Gly Val Leu Ile
145                 150                 155                 160

Ile Gly Ser Gly Gly Thr Val His Pro Ser Asp Asp Thr Pro His Cys
                165                 170                 175

Pro Asn Gly Val Ala Pro Trp Ala Ile Glu Phe Asp Asn Trp Leu Glu
            180                 185                 190

Asp Ala Leu Leu Ser Gly Arg Tyr Glu Asp Val Asn Asn Phe Lys Lys
        195                 200                 205

Leu Ala Pro Asn Trp Glu Ile Ser His Pro Gly Gln Glu His Leu Tyr
    210                 215                 220

Pro Leu His Val Ala Leu Gly Ala Ala Gly Lys Asn Pro Lys Thr Gln
225                 230                 235                 240

Leu Ile His Arg Ser Trp Ala Ala Asn Gly Val Phe Gly Tyr Ser Thr
                245                 250                 255

Tyr Asn Phe Thr Pro Thr Thr Gln Lys Thr Asp
            260                 265
```

```
<210> SEQ ID NO 35
<211> LENGTH: 804
<212> TYPE: DNA
<213> ORGANISM: Mirabilis jalapa

<400> SEQUENCE: 35

atgaaaggaa catactatat aaatcatggt gatccactaa tgtacttaaa aaaacatata      60

aaactaaggc aattcttaga aggatggcaa gaaaatgttg ttattgaaaa accaaagagt     120

atacttatca tttctgctca ttgggatact aatgtaccta ctgtcaactt tgttgaacat     180

tgtgatacta ttcatgattt tgatgactat cctgatcctt tgtaccagat acaatatcga     240

gcaccgggag caccaaattt agcaaaaaag gtggaagagt tactaaaaga gtcaggaatg     300

gaatgtgaga tagatacaaa gagaggactc gatcatgcag catggtttcc actaatgttt     360

atgtatcctg aagctaatat tcctatttgt gagctctcag tccaaccaag caaagatggg     420

atccaccact ataatgttgg gaaagctctt tctcctcttt tgcaacaagg tgttctcatc     480

attggctctg gtggtactgt tcatccttct gatgatactc ctcattgtcc caatggtgtt     540

gctccttggg ctattgagtt tgataactgg cttgaagatg ctcttcttag tggaaggtat     600

gaagatgtga acaacttcaa gaaattggca ccaaattggg agatatctca tccaggacaa     660

gaacatttgt accctttgca tgtggcatta ggggctgctg gcaaaaatcc aaagacacaa     720
```

-continued

```
cttattcatc gaagctgggc tgccaatggt gtctttggat attccaccta caacttcact    780

cccaccactc aaaaaactga ttaa                                            804


<210> SEQ ID NO 36
<211> LENGTH: 1446
<212> TYPE: DNA
<213> ORGANISM: Cleretum bellidiforme

<400> SEQUENCE: 36

atgagcaaaa tagagctggt gttggttcca accccaggga tgggccactt gctctccgcc     60

gtcgagctat ccaagctcat tatccgccgt gagaaccgta tctcagtcct catcctaatc    120

ttaagcttcc cctttgactc cggtttggtt aatgcctacg ttgatttcca gtcacgtgac    180

cctgacaact ccggtagcct aaccttcatc actctcccac cactctccaa catacctgac    240

tgcacttcga gcaccttctt caccaccgtc attgaactcc acaagccaaa tgtcaagcag    300

gttgtcgagg aacgagtcag gtccgggtca cccaagcctg ctgggtttgt tatagacatg    360

ctttgccctg ctatgatgga tgtcgcggag gagcttgagg taccttctta catattgttc    420

acctctgggg ctaacttgtt gaatgtagtg tttcatttcc tgtcactcgc tgataatggc    480

gtggatatcg ccactgaagt taatgatccg gataaggagg tggatgttcc cgggttcagg    540

aaccgggtgc cctgcaaggt cttacccttg cccttccttg agaaagattt tctagtgaag    600

cgcggaagga ggtttagacg atccaacggt attctagtga acacttccaa tgagctggaa    660

tcgtatgcga ttcagacgtt gcttgagcag gctaaggata ataagatccc acccgtttat    720

ccggtaggtc ccattttgga gctgaatagc aaaagccgtt gtgggactaa ggaagatgag    780

gaagtctcga tcatgaggtg gctagacgag cagccagtaa actcggtgct gttcgtttgc    840

tttggaagca tgggaacatt cgatgaggat caagtaaagg agatagccaa tggtctagag    900

cagtcggggt attgctttct atggtcctta cgccagccac ccccggaagg gaaggcgaca    960

ccaagcgagg aggccttcct ggacaccctt ccagaggggt tcgtagagcg tacatcccat   1020

aaggggaaga tcatcgggtg ggctccgcag gtatcaatac tagcccacaa ggctgttggg   1080

ggattcgtgt cacattgtgg ttggaactcg actttagaga gtctctggtt tggggtccca   1140

atggcaacgt ggccaattag cgcggagcag cagctgaacg catttgagct agtgaaagag   1200

ttcgggatgg cggtagagat tcggatggat ttttggcgag attgtaggaa aaatactcag   1260

agctttgtag taacgagtga ggagatagag aatggggtga agaagctgat gagtatggat   1320

gaagaaatgg tcgagaaagt aaagaagatg agtgataaga gtaggaagac tttagaggat   1380

ggcggatctt cgcatcactc gttgggccgt ttcattaatg atctcttgga gaacgctggc   1440

ttctga                                                               1446


<210> SEQ ID NO 37
<211> LENGTH: 481
<212> TYPE: PRT
<213> ORGANISM: Cleretum bellidiforme

<400> SEQUENCE: 37

Met Ser Lys Ile Glu Leu Val Leu Val Pro Thr Pro Gly Met Gly His
1               5                   10                  15

Leu Leu Ser Ala Val Glu Leu Ser Lys Leu Ile Ile Arg Arg Glu Asn
            20                  25                  30

Arg Ile Ser Val Leu Ile Leu Ile Leu Ser Phe Pro Phe Asp Ser Gly
        35                  40                  45
```

```
Leu Val Asn Ala Tyr Val Asp Phe Gln Ser Arg Asp Pro Asp Asn Ser
    50                  55                  60

Gly Ser Leu Thr Phe Ile Thr Leu Pro Pro Leu Ser Asn Ile Pro Asp
65                  70                  75                  80

Cys Thr Ser Ser Thr Phe Phe Thr Thr Val Ile Glu Leu His Lys Pro
                85                  90                  95

Asn Val Lys Gln Val Val Glu Glu Arg Val Arg Ser Gly Ser Pro Lys
            100                 105                 110

Pro Ala Gly Phe Val Ile Asp Met Leu Cys Pro Ala Met Met Asp Val
        115                 120                 125

Ala Glu Glu Leu Glu Val Pro Ser Tyr Ile Leu Phe Thr Ser Gly Ala
    130                 135                 140

Asn Leu Leu Asn Val Val Phe His Phe Leu Ser Leu Ala Asp Asn Gly
145                 150                 155                 160

Val Asp Ile Ala Thr Glu Val Asn Asp Pro Asp Lys Glu Val Asp Val
                165                 170                 175

Pro Gly Phe Arg Asn Arg Val Pro Cys Lys Val Leu Pro Leu Pro Phe
            180                 185                 190

Leu Glu Lys Asp Phe Leu Val Lys Arg Gly Arg Arg Phe Arg Arg Ser
        195                 200                 205

Asn Gly Ile Leu Val Asn Thr Ser Asn Glu Leu Glu Ser Tyr Ala Ile
    210                 215                 220

Gln Thr Leu Leu Glu Gln Ala Lys Asp Asn Lys Ile Pro Pro Val Tyr
225                 230                 235                 240

Pro Val Gly Pro Ile Leu Glu Leu Asn Ser Lys Ser Arg Cys Gly Thr
                245                 250                 255

Lys Glu Asp Glu Glu Val Ser Ile Met Arg Trp Leu Asp Glu Gln Pro
            260                 265                 270

Val Asn Ser Val Leu Phe Val Cys Phe Gly Ser Met Gly Thr Phe Asp
        275                 280                 285

Glu Asp Gln Val Lys Glu Ile Ala Asn Gly Leu Glu Gln Ser Gly Tyr
    290                 295                 300

Cys Phe Leu Trp Ser Leu Arg Gln Pro Pro Pro Glu Gly Lys Ala Thr
305                 310                 315                 320

Pro Ser Glu Glu Ala Phe Leu Asp Thr Leu Pro Glu Gly Phe Val Glu
                325                 330                 335

Arg Thr Ser His Lys Gly Lys Ile Ile Gly Trp Ala Pro Gln Val Ser
            340                 345                 350

Ile Leu Ala His Lys Ala Val Gly Gly Phe Val Ser His Cys Gly Trp
        355                 360                 365

Asn Ser Thr Leu Glu Ser Leu Trp Phe Gly Val Pro Met Ala Thr Trp
    370                 375                 380

Pro Ile Ser Ala Glu Gln Gln Leu Asn Ala Phe Glu Leu Val Lys Glu
385                 390                 395                 400

Phe Gly Met Ala Val Glu Ile Arg Met Asp Phe Trp Arg Asp Cys Arg
                405                 410                 415

Lys Asn Thr Gln Ser Phe Val Val Thr Ser Glu Glu Ile Glu Asn Gly
            420                 425                 430

Val Lys Lys Leu Met Ser Met Asp Glu Glu Met Val Glu Lys Val Lys
        435                 440                 445

Lys Met Ser Asp Lys Ser Arg Lys Thr Leu Glu Asp Gly Gly Ser Ser
    450                 455                 460

His His Ser Leu Gly Arg Phe Ile Asn Asp Leu Leu Glu Asn Ala Gly
```

-continued 465 470 475 480

Phe

<210> SEQ ID NO 38
<211> LENGTH: 30
<212> TYPE: DNA
<213> ORGANISM: Artificial Sequence
<220> FEATURE:
<223> OTHER INFORMATION: primer for Cq3GGT-like1

<400> SEQUENCE: 38
atgtccaagg aaaatggcat tgccaatggc 30

<210> SEQ ID NO 39
<211> LENGTH: 30
<212> TYPE: DNA
<213> ORGANISM: Artificial Sequence
<220> FEATURE:
<223> OTHER INFORMATION: primer for Cq3GGT-like1

<400> SEQUENCE: 39
tcatacgaga atacctttca gactctgtat 30

<210> SEQ ID NO 40
<211> LENGTH: 33
<212> TYPE: DNA
<213> ORGANISM: Artificial Sequence
<220> FEATURE:
<223> OTHER INFORMATION: oriner for Cq3GGT-like3

<400> SEQUENCE: 40
atgtccaagg aaaatggcat tgctaatggc aat 33

<210> SEQ ID NO 41
<211> LENGTH: 35
<212> TYPE: DNA
<213> ORGANISM: Artificial Sequence
<220> FEATURE:
<223> OTHER INFORMATION: primer for Cq3GGT-like3

<400> SEQUENCE: 41
ttatacgaga atgtctttca gactctgtat gaacc 35

<210> SEQ ID NO 42
<211> LENGTH: 34
<212> TYPE: DNA
<213> ORGANISM: Artificial Sequence
<220> FEATURE:
<223> OTHER INFORMATION: primer for Cq3GGT-like2

<400> SEQUENCE: 42
atgtcatcat caaacaataa caatggcaag actt 34

<210> SEQ ID NO 43
<211> LENGTH: 33
<212> TYPE: DNA
<213> ORGANISM: Artificial Sequence
<220> FEATURE:
<223> OTHER INFORMATION: primer for Cq3GGT-like2

<400> SEQUENCE: 43
tcaaaccaaa tcttgtagac tttgaacaaa ctt 33

<210> SEQ ID NO 44
<211> LENGTH: 30

<212> TYPE: DNA
<213> ORGANISM: Artificial Sequence
<220> FEATURE:
<223> OTHER INFORMATION: primer for CqUGT79B30-like2

<400> SEQUENCE: 44
atgtcaaaga ttaacgaaac caatgaatgt 30

<210> SEQ ID NO 45
<211> LENGTH: 33
<212> TYPE: DNA
<213> ORGANISM: Artificial Sequence
<220> FEATURE:
<223> OTHER INFORMATION: primer for CqUGT79B30-like2

<400> SEQUENCE: 45
tcaaaccaaa tcttgtagac tttgaacaaa ctt 33

<210> SEQ ID NO 46
<211> LENGTH: 30
<212> TYPE: DNA
<213> ORGANISM: Artificial Sequence
<220> FEATURE:
<223> OTHER INFORMATION: primer for CqAmaSy2

<400> SEQUENCE: 46
atgtcacaaa acaaagacac ccaaattcta 30

<210> SEQ ID NO 47
<211> LENGTH: 31
<212> TYPE: DNA
<213> ORGANISM: Artificial Sequence
<220> FEATURE:
<223> OTHER INFORMATION: primer for CqAmaSy2

<400> SEQUENCE: 47
tcatgatcca atcaattgtt gcaaactcat a 31

<210> SEQ ID NO 48
<211> LENGTH: 25
<212> TYPE: DNA
<213> ORGANISM: Artificial Sequence
<220> FEATURE:
<223> OTHER INFORMATION: primer for CqAmaSy1

<400> SEQUENCE: 48
atgtcacaaa acaaagacaa ccaaa 25

<210> SEQ ID NO 49
<211> LENGTH: 30
<212> TYPE: DNA
<213> ORGANISM: Artificial Sequence
<220> FEATURE:
<223> OTHER INFORMATION: primer for CqAmaSy1

<400> SEQUENCE: 49
ttatgatcct atcaattgtt gcaaactctg 30

<210> SEQ ID NO 50
<211> LENGTH: 34
<212> TYPE: DNA
<213> ORGANISM: Artificial Sequence
<220> FEATURE:
<223> OTHER INFORMATION: primer for CqUGT79B30-like1

<400> SEQUENCE: 50

-continued atgtctaaca acaaaaactc caaaattcta aaag 34

<210> SEQ ID NO 51
<211> LENGTH: 35
<212> TYPE: DNA
<213> ORGANISM: Artificial Sequence
<220> FEATURE:
<223> OTHER INFORMATION: primer for CqUGT79B30-like1

<400> SEQUENCE: 51
tcactcaagc aacttttgta gattataaat gaagc 35

<210> SEQ ID NO 52
<211> LENGTH: 37
<212> TYPE: DNA
<213> ORGANISM: Artificial Sequence
<220> FEATURE:
<223> OTHER INFORMATION: primer for CqUGT79B30-like5

<400> SEQUENCE: 52
atggataaaa aaatagcaag tatggttgag gaaaaag 37

<210> SEQ ID NO 53
<211> LENGTH: 31
<212> TYPE: DNA
<213> ORGANISM: Artificial Sequence
<220> FEATURE:
<223> OTHER INFORMATION: primer for CqUGT79B30-like5

<400> SEQUENCE: 53
tcatgtaact agatctagta gattttcaac a 31

<210> SEQ ID NO 54
<211> LENGTH: 26
<212> TYPE: DNA
<213> ORGANISM: Artificial Sequence
<220> FEATURE:
<223> OTHER INFORMATION: primer for CqCYP76AD1-1

<400> SEQUENCE: 54
atggatcatg caacactagc aatgat 26

<210> SEQ ID NO 55
<211> LENGTH: 26
<212> TYPE: DNA
<213> ORGANISM: Artificial Sequence
<220> FEATURE:
<223> OTHER INFORMATION: primer for CqCYP76AD1-1

<400> SEQUENCE: 55
tcaataccta agaacgggaa taatct 26

METHOD FOR SYNTHESIZING BETALAIN PIGMENT

TECHNICAL FIELD

The present invention relates to a synthesis method for a betalain pigment, an amaranthin synthesis or gomphrenin-I-glucuronide synthesis composition agent, an amaranthin synthesis method, a gomphrenin-I-glucuronide synthesis method, and a betalain pigment-producing host.

The present application is a National Stage Application of PCT/JP2019/041002, filed Oct. 18, 2019, which claims priority from Japanese Patent Application No. 2018-197998, which is incorporated herein by reference.

BACKGROUND ART (Betalains)

Betalains, which are a group of plant pigments, are produced in plants of the order Caryophyllales and some fungi. The betalain pigments are broadly classified into two groups, i.e., betacyanins, which range from red to violet in color, and betaxanthins, which range from yellow to orange in color. In plants, the betalain pigments are known to be involved in resistance to environmental stresses (Non Patent Literature 1 and Non Patent Literature 2). The betalain pigments are used for food additives because of their vivid colors. In addition, the betalain pigments have high antioxidant activity, and hence are expected to be utilized as pharmaceuticals and supplements. The betalain pigments, though having various physiological actions, are difficult to constantly produce because the production of the betalain pigments is mainly performed through extraction from betalain pigment-producing plants. In recent years, it has been reported that betalains have been successfully produced by introducing betalain biosynthesis genes into non-betalain-producing plants (Non Patent Literature 2). However, although many kinds of betalain pigments exist, few genes for synthesis thereof have been isolated, and hence only certain betalain pigments have been able to be synthesized.

*Quinoa*, which is native to the Andes of South America, is a plant that produces and accumulates betalains. As betalain pigments accumulating in *quinoa* seedlings, amaranthin and celosianin II primarily accumulate (Non Patent Literature 3). Amaranthin is a betalain pigment in which glucuronic acid is bonded to betanin (FIG. 1). Biosynthetic pathways of betalain pigments have been increasingly elucidated in recent years, and genes involved before and in synthesis of betanin, which serves as a precursor of amaranthin, have been reported. However, a gene having an ability to synthesize amaranthin has not been reported. Accordingly, amaranthin is a betalain pigment that is impossible to produce in a non-betalain-producing plant.

In Patent Literature 1, there is a disclosure of a "method of producing a betacyanin, including a step (conversion step) of converting a raw material into a betacyanin in an aqueous medium in the presence of a microorganism having enzyme activity of hydroxylating the 3-position of the phenol ring of tyrosine, DOPA 4,5-dioxygenase activity, L-DOPA oxidase activity, and enzyme activity of glycosylating a phenolic hydroxy group, or a treated product thereof."

In Non Patent Literature 4, there is a report that "a betanin synthesis system of *Mirabilis jalapa* synthesizes 88% of betanin, which is an S-form, and 12% of isobetanin, which is an R-form."

In Non Patent Literature 2, there is a report that "a betanin synthesis system of potato synthesizes both the S-form and the R-form."

In Non Patent Literature 5, there is a report that "a betanin synthesis system of *Nicotiana benthamiana* synthesizes both the S-form and the R-form."

However, in any of the Literatures, there is no disclosure or suggestion of an amaranthin or gomphrenin-I-glucuronide synthetase gene of the present invention.

CITATION LIST

Patent Literature

[PTL 1] JP 2016-182044 A

Non Patent Literature

[NPL 1] Jain, G., Schwinn, K. E. and Gould, K. S. (2015) Betalain induction byl-DOPA application confers photoprotection to saline-exposed leaves of Disphymaaustrale. New Phytol. 207, 1075-1083.

[NPL 2] Polturak, G., Grossman, N., Vela-Corcia, D., et al. 2017, Engineered gray mold resistance, antioxidant capacity, and pigmentation in betalain-producing crops and ornamentals. Proc. Natl. Acad. Sci. U.S.A, 114, 9062-7.

[NPL 3] Imamura, T., Takagi, H., Miyazato, A., Ohki, S., Mizukoshi, H. and Mori, M. (2018) Isolation and characterization of the betalain biosynthesis gene involved in hypocotyl pigmentation of the allotetraploid *Chenopodium quinoa*. Biochem. Biophys. Res. Commun. 496, 280-286.

[NPL 4] Sasaki, N., Abe, Y., Goda, Y., Adachi, T., Kasahara, K. and Ozeki, Y. 2009, Detection of DOPA 4,5-dioxygenase (DOD) activity using recombinant protein prepared from *Escherichia coli* cells harboring cDNA encoding DOD from *Mirabilis jalapa*. Plant Cell Physiol., 50, 1012-6.

[NPL 5] Polturak, G., Breitel, D., Grossman, N., etal. 2016, Elucidation of the first committed step in betalain biosynthesis enables the heterologous engineering of betalain pigments in plants. New Phytol., 210, 269-83.

SUMMARY OF INVENTION

Technical Problem

An object of the present invention is to provide a method of synthesizing amaranthin or gomphrenin-I-glucuronide.

Solution to Problem

In order to achieve the above-mentioned object, the inventors of the present invention have isolated genes each having an amaranthin or gomphrenin-I-glucuronide synthesis ability from *quinoa* and the like, and have used the isolated genes to verify the amaranthin or gomphrenin-I-glucuronide synthesis ability in non-betalain-producing plants.

Thus, the inventors have completed a synthesis method for a betalain pigment, an amaranthin synthesis method, a gomphrenin-I-glucuronide synthesis method, an amaranthin or gomphrenin-I-glucuronide synthesis composition, and a betalain pigment-producing host of the present invention.

That is, the present invention is as described below.

1. A synthesis method for a betalain pigment, including:

culturing a host that has introduced therein the following gene encoding an amaranthin or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding an enzyme having activity of glycosylating a phenolic hydroxy group, and a gene encoding an enzyme having DOPA 4,5-dioxygenase activity, and that has an ability to produce tyrosine or 3-hydroxy-L-tyrosine (L-DOPA), and extracting a betalain pigment from the host after the culturing; or culturing a host that has introduced therein the following gene encoding an amaranthin or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding a betanidin-to-betanin synthetase, and a gene encoding an enzyme having DOPA 4,5-dioxygenase activity, and that has an ability to produce tyrosine or 3-hydroxy-L-tyrosine, and extracting a betalain pigment from the host after the culturing; or culturing a host that has introduced therein the following gene encoding an amaranthin or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding a betanidin-to-gomphrenin-I (betanidin 6-O-glucoside) synthetase, and a gene encoding an enzyme having DOPA 4,5-dioxygenase activity, and that has an ability to produce tyrosine or 3-hydroxy-L-tyrosine, and extracting a betalain pigment from the host after the culturing;

or culturing a host that has introduced therein the following gene encoding an amaranthin or gomphrenin-I-glucuronide synthetase, and that has enzyme activity of having activity of hydroxylating a 3-position of a phenol ring of tyrosine, enzyme activity of having L-DOPA oxidase activity, enzyme activity of having activity of glycosylating a phenolic hydroxy group, enzyme activity of having DOPA 4,5-dioxygenase activity, and an ability to produce tyrosine or 3-hydroxy-L-tyrosine, and extracting a betalain pigment from the host after the culturing; or culturing a host that has introduced therein the following gene encoding an amaranthin or gomphrenin-I-glucuronide synthetase, and that has enzyme activity of having activity of hydroxylating a 3-position of a phenol ring of tyrosine, enzyme activity of having L-DOPA oxidase activity, enzyme activity of having betanidin-to-betanin synthesis activity, enzyme activity of having DOPA 4,5-dioxygenase activity, and an ability to produce tyrosine or 3-hydroxy-L-tyrosine, and extracting a betalain pigment from the host after the culturing; or culturing a host that has introduced therein the following gene encoding an amaranthin or gomphrenin-I-glucuronide synthetase, and that has enzyme activity of having activity of hydroxylating a 3-position of a phenol ring of tyrosine, enzyme activity of having L-DOPA oxidase activity, enzyme activity of having betanidin-to-gomphrenin-I synthesis activity, enzyme activity of having DOPA 4,5-dioxygenase activity, and an ability to produce tyrosine or 3-hydroxy-L-tyrosine, and extracting a betalain pigment from the host after the culturing, wherein, in the production method for a betalain pigment, the gene encoding an amaranthin or gomphrenin-I-glucuronide synthetase is any one or more selected from the following:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11;

(7) a gene formed of DNA having 90% or more homology to DNA formed of the base sequence set forth in SEQ ID NO: 1, 3, 5, 7, 9, or 11; and (8) a gene formed of DNA formed of a degenerate isomer of the base sequence set forth in SEQ ID NO: 1, 3, 5, 7, 9, or 11.

2. The synthesis method for a betalain pigment according to the above-mentioned item 1, wherein the betalain pigment is amaranthin.

3. The synthesis method for a betalain pigment according to the above-mentioned item 1, wherein the betalain pigment is gomphrenin-I-glucuronide.

4. The synthesis method for a betalain pigment according to any one of the above-mentioned items 1 to 3, wherein the gene encoding an amaranthin or gomphrenin-I-glucuronide synthetase is any one or more selected from SEQ ID NOS: 1, 3, 5, 7, 9, and 11.

5. An amaranthin synthesis or gomphrenin-I-glucuronide synthesis composition, including a gene shown in any one of the following items (1) to (7) or a vector carrying the gene:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11;

(7) a gene formed of DNA having 90% or more homology to DNA formed of the base sequence set forth in SEQ ID NO: 1, 3, 5, 7, 9, or 11; and (8) a gene formed of DNA formed of a degenerate isomer of the base sequence set forth in SEQ ID NO: 1, 3, 5, 7, 9, or 11.

6. An amaranthin synthesis or gomphrenin-I-glucuronide synthesis composition, including a peptide represented by an amino acid sequence of any one of the following items (1) to (3):

(1) an amino acid sequence set forth in SEQ ID NO: 2, 4, 6, 8, 10, or 12;

(2) an amino acid sequence that has 1 to 20 amino acids substituted, deleted, inserted, and/or added in the amino acid sequence set forth in SEQ ID NO: 2, 4, 6, 8, 10, or 12, and that forms a polypeptide having a substantially equivalent ability to synthesize amaranthin or gomphrenin-I-glucuronide to that of the amino acid sequence set forth in SEQ ID NO: 2, 4, 6, 8, 10, or 12; and (3) an amino acid sequence that has 90% or more homology to the amino acid sequence set forth in SEQ ID NO: 2, 4, 6, 8, 10, or 12, and that forms a polypeptide having a substantially equivalent ability to synthesize amaranthin or gomphrenin-I-glucuronide to that of the amino acid sequence set forth in SEQ ID NO: 2, 4, 6, 8, 10, or 12.

7. A betalain pigment-producing host having introduced therein the synthesis composition of the above-mentioned item 5 or 6.

8. An amaranthin synthesis method, including the following (1) or (2)

(1) a step of bringing betanin into contact with the amaranthin synthesis or gomphrenin-I-glucuronide synthesis composition of the above-mentioned item 6; or (2) (a) a step of bringing betanidin into contact with a betanidin-to-betanin synthetase, and (b) a step of bringing betanin obtained in the step (a) into contact with the amaranthin synthesis or gomphrenin-I-glucuronide synthesis composition of the above-mentioned item 6.

9. A gomphrenin-I-glucuronide synthesis method, including the following (1) or (2):

(1) a step of bringing gomphrenin-I into contact with the amaranthin synthesis or gomphrenin-I-glucuronide synthesis composition of the above-mentioned item 6; or (2) (a) a step of bringing betanidin into contact with a betanidin-to-gomphrenin-I synthetase, and (b) a step of bringing gomphrenin-I obtained in the step (a) into contact with the amaranthin synthesis or gomphrenin-I-glucuronide synthesis composition of the above-mentioned item 6.

10. A betalain pigment-producing host, the host having introduced therein the following gene encoding an amaranthin or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding an enzyme having activity of glycosylating a phenolic hydroxy group, and a gene encoding an enzyme having DOPA 4,5-dioxygenase activity, and having an ability to produce tyrosine or L-DOPA, or the host having introduced therein the following gene encoding an amaranthin or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding a betanidin-to-betanin synthetase, and a gene encoding an enzyme having DOPA 4,5-dioxygenase activity, and having an ability to produce tyrosine or L-DOPA, or the host having introduced therein the following gene encoding an amaranthin or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding an enzyme having betanidin-to-gomphrenin-I synthesis activity, and a gene encoding an enzyme having DOPA 4,5-dioxygenase activity, and having an ability to produce tyrosine or L-DOPA, or the host having introduced therein the following gene encoding an amaranthin or gomphrenin-I-glucuronide synthetase, and having enzyme activity of having activity of hydroxylating a 3-position of a phenol ring of tyrosine, enzyme activity of having L-DOPA oxidase activity, enzyme activity of having activity of glycosylating a phenolic hydroxy group, enzyme activity of having DOPA 4,5-dioxygenase activity, and an ability to produce tyrosine or 3-hydroxy-L-tyrosine, or the host having introduced therein the following gene encoding an amaranthin or gomphrenin-I-O-glucuronide synthetase, and having enzyme activity of having activity of hydroxylating a 3-position of a phenol ring of tyrosine, enzyme activity of having L-DOPA oxidase activity, enzyme activity of having betanidin-to-betanin synthesis activity, enzyme activity of having DOPA 4,5-dioxygenase activity, and an ability to produce tyrosine or 3-hydroxy-L-tyrosine, or the host having introduced therein the following gene encoding an amaranthin or gomphrenin-I-glucuronide synthetase, and having enzyme activity of having activity of hydroxylating a 3-position of a phenol ring of tyrosine, enzyme activity of having L-DOPA oxidase activity, enzyme activity of having betanidin-to-gomphrenin-I synthesis activity, enzyme activity of having DOPA 4,5-dioxygenase activity, and an ability to produce tyrosine or 3-hydroxy-L-tyrosine, wherein the gene encoding an amaranthin or gomphrenin-I-glucuronide synthetase is any one or more selected from the following:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11;

(7) a gene formed of DNA having 90% or more homology to DNA formed of the base sequence set forth in SEQ ID NO: 1, 3, 5, 7, 9, or 11; and (8) a gene formed of DNA formed of a degenerate isomer of the base sequence set forth in SEQ ID NO: 1, 3, 5, 7, 9, or 11.

11. A therapeutic or preventive agent for cancer, including any one of the following items (1) to (4):

(1) amaranthin;

(2) amaranthin obtained by the synthesis method for a betalain pigment of any one of the above-mentioned items 1, 2, and 4;

(3) amaranthin obtained by the amaranthin synthesis method of the above-mentioned item 8; and (4) amaranthin obtained from the betalain pigment-producing host of the above-mentioned item 10.

12. An HIV-1 protease activity inhibitor, including any one of the following items (1) to (4):

(1) amaranthin;

(2) amaranthin obtained by the synthesis method for a betalain pigment of any one of the above-mentioned items 1, 2, and 4;

(3) amaranthin obtained by the amaranthin synthesis method of the above-mentioned item 8; and (4) amaranthin obtained from the betalain pigment-producing host of the above-mentioned item 10.

Advantageous Effects of Invention

According to the present invention, the synthesis method for a betalain pigment, the amaranthin synthesis or gomphrenin-I-glucuronide synthesis composition, the amaranthin synthesis method, the gomphrenin-I-glucuronide synthesis method, and the betalain pigment-producing host can be provided.

BRIEF DESCRIPTION OF DRAWINGS

FIG. 3 are schematic diagrams of an amaranthin synthesis reaction.

FIG. 7 show the results of identification of the amaranthin biosynthesis gene.

FIG. 9 show the results of identification of amaranthin biosynthesis genes in beets and amaranth.

FIG. 11 show the results of estimation of a substrate for CqAmaSy1.

FIG. 13 show the results of production of betalain pigments in tobacco BY-2 cell lines.

FIG. 14 show the results of evaluation of cell proliferation in MCF-7 cells.

FIG. 15 show the results of evaluation of inhibition of an HIV-1 protease.

DESCRIPTION OF EMBODIMENTS

The present invention relates to a synthesis method for a betalain pigment, an amaranthin or gomphrenin-I-glucuronide synthesis composition, an amaranthin synthesis method, a gomphrenin-I-glucuronide synthesis method, and a betalain pigment-producing host. The present invention is described in detail below.

(Betalain Pigment)

Betalain pigments in the present invention are classified into betaxanthins and betacyanins on the basis of their structural features. The betaxanthins exhibit yellow colors and the betacyanins exhibit red-violet colors, and hence the betaxanthins and the betacyanins have heretofore been utilized as natural colorants. The term "betacyanins" collectively refers to a group of compounds in each of which a sugar is glycosidically bonded to a phenolic hydroxy group of betanidin.

(Betalain Pigment Synthesis System)

Figure 1:
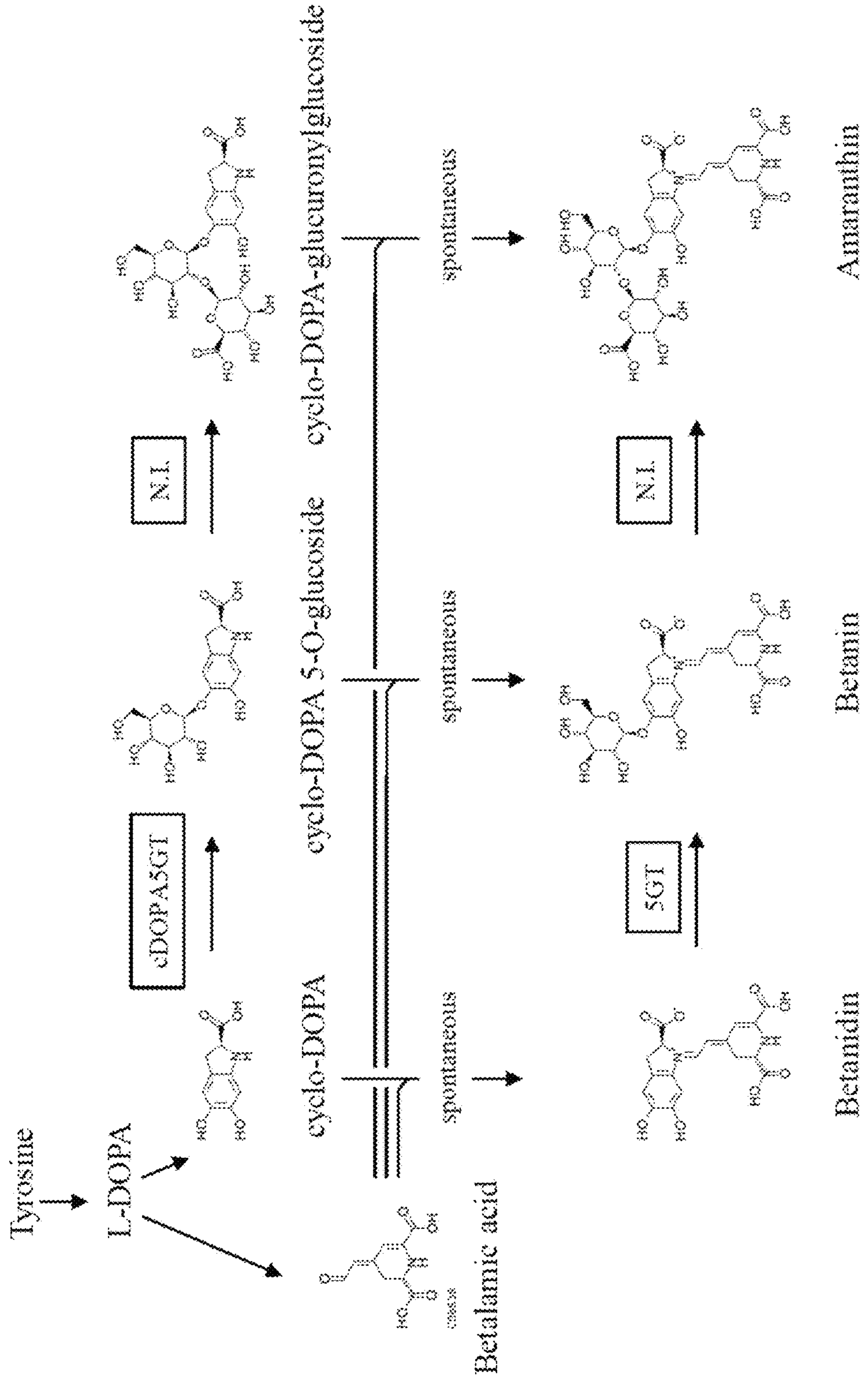
FIG. 1 is a scheme for a biosynthetic pathway of betacyanins, which are a group of betalain pigments. Boxes indicate betacyanin-modifying enzymes. cDOPA5GT represents cyclo-DOPA 5-O-glucosyltransferase, and 5GT represents betanidin 5-O-glucosyltransferase. N.I. means not identified.
Figure 2:
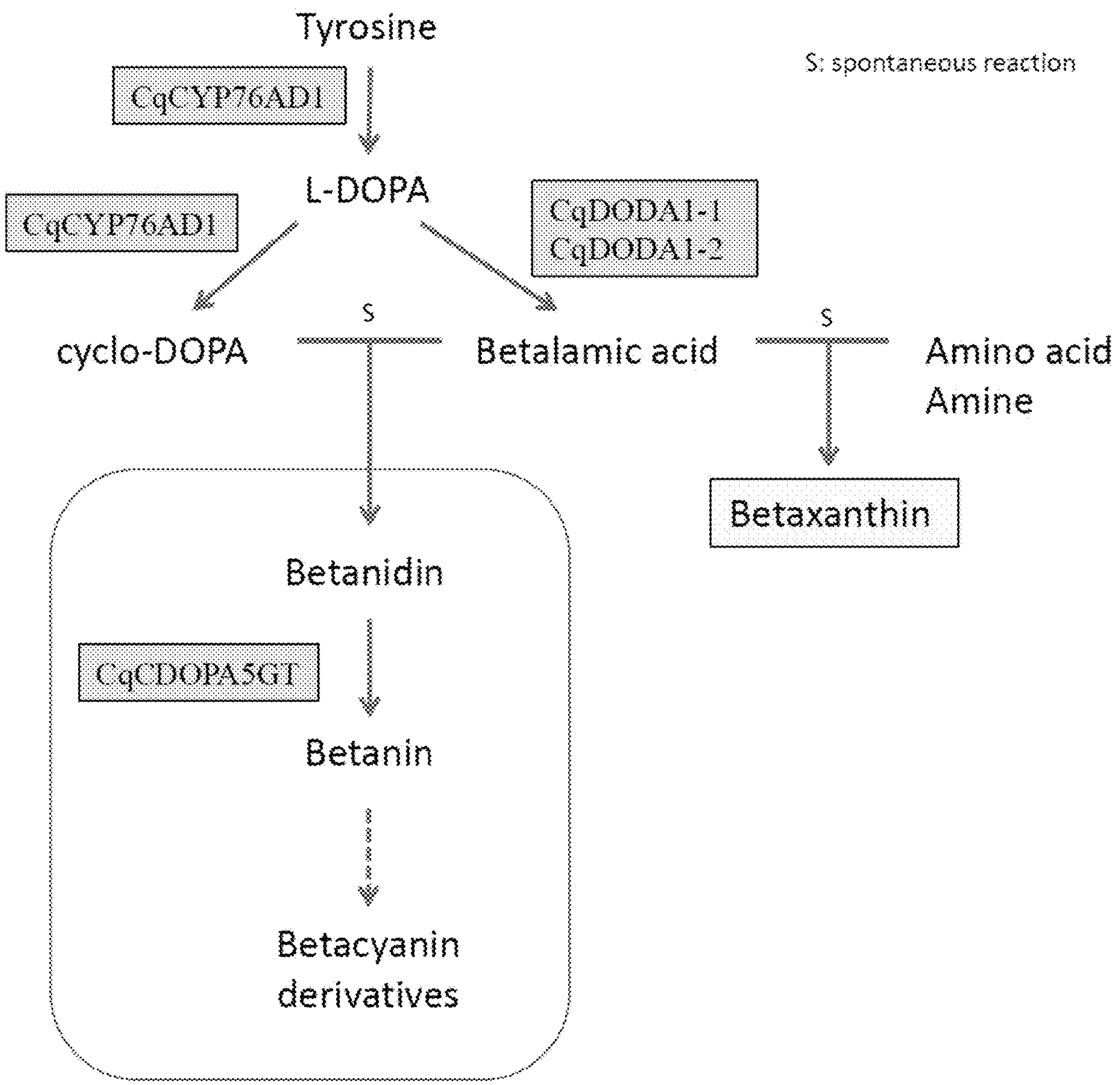
FIG. 2 is a scheme for a betalain pigment synthetic pathway.
Figure 16:
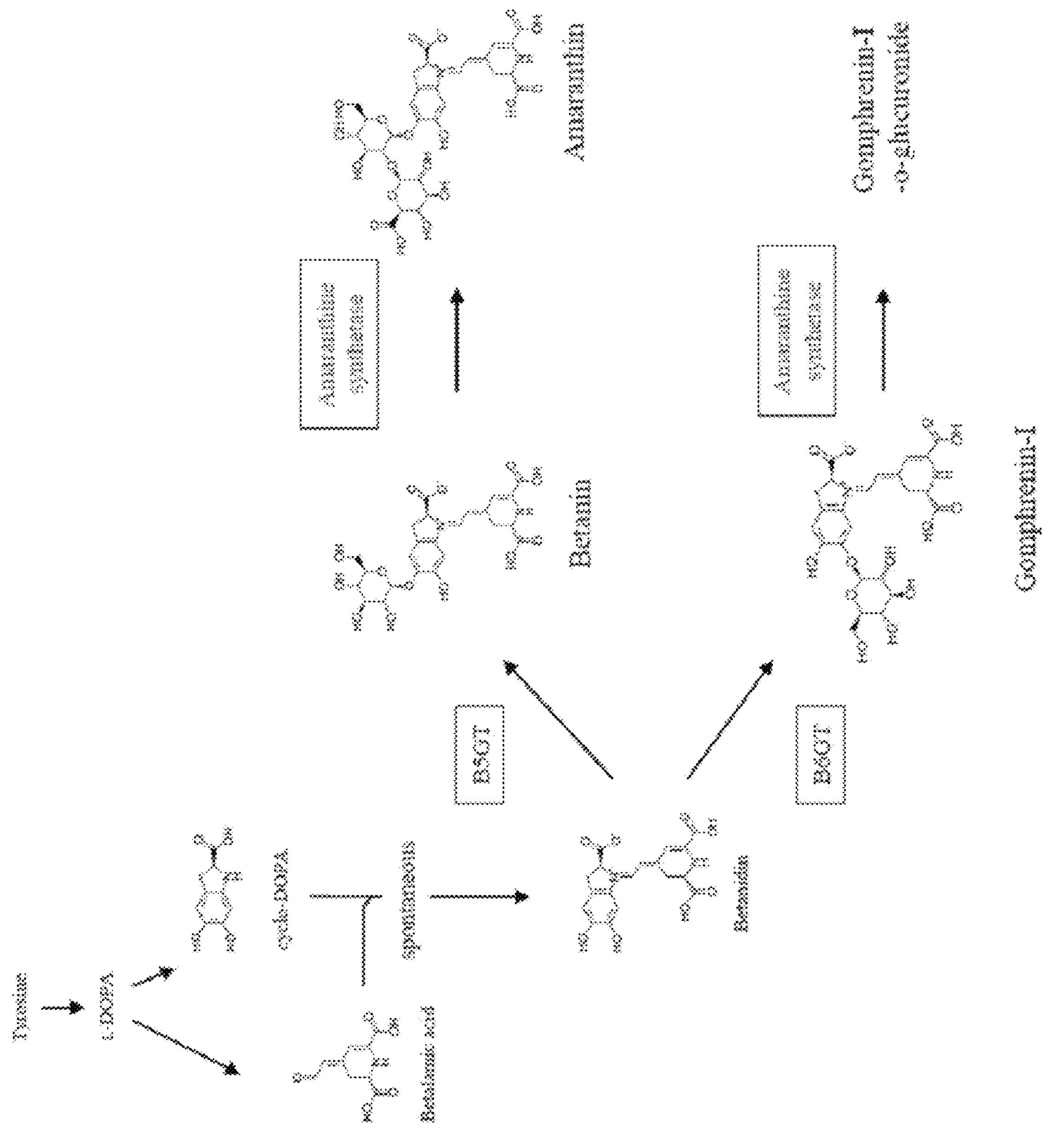
FIG. 16 is an illustration of amaranthin and gomphrenin-I-O-glucuronide synthetic pathways.

Schemes for betacyanin biosynthetic pathways in the present invention are illustrated in FIG. 1, FIG. 2, and FIG. 16.

As apparent from the illustrations in FIG. 1 and FIG. 2, when a host having an ability to produce tyrosine or 3-hydroxy-L-tyrosine (L-DOPA), and an amino acid or an amine (e.g., putrescine, spermidine, or spermine) (including a host capable of incorporating these compounds from outside) has enzyme activities of the following item (1) or (2), amaranthin can be synthesized.

(1) Enzyme (e.g., CqCYP76AD1) activity of hydroxylating the 3-position of the phenol ring of tyrosine, enzyme (e.g., CqCYP76AD1) activity of having L-DOPA oxidase activity, enzyme (e.g., CqDODA-1) activity of having DOPA 4,5-dioxygenase activity, the activity of an enzyme having activity of glycosylating a phenolic hydroxy group {e.g., an enzyme having betanidin 5-O-glucosyltransferase activity (e.g., Cyclo-DOPA 5-O-glucosyltransferase, CqCDOPA5GT), and amaranthin or gomphrenin-I-glucuronide synthetase activity of the present invention. CqCYP76AD1 has both of the following properties: enzyme activity of hydroxylating the 3-position of the phenol ring of tyrosine; and enzyme activity of having L-DOPA oxidase activity.

(2) Enzyme activity of hydroxylating the 3-position of the phenol ring of tyrosine, enzyme activity of having L-DOPA oxidase activity, enzyme activity of having DOPA 4,5-dioxygenase activity, betanidin-to-betanin synthetase {betanidin 5-O-glucosyltransferase (5GT) enzyme}activity, and amaranthin or gomphrenin-I-glucuronide synthetase activity of the present invention.

According to the results of Example 4 to be described below, a plant body that is a host having introduced therein a gene group of a gene encoding an enzyme having activity of hydroxylating the 3-position of the phenol ring of tyrosine (gene encoding an enzyme having L-DOPA oxidase activity), a gene encoding an enzyme having activity of glycosylating a phenolic hydroxy group, a gene encoding an enzyme having DOPA 4,5-dioxygenase activity, and a gene encoding an amaranthin or gomphrenin-I-glucuronide synthetase of the present invention has an ability to synthesize amaranthin, which is a betalain pigment.

As apparent from the illustration in FIG. 16, when a host having an ability to produce tyrosine or L-DOPA, and an amino acid or an amine (e.g., putrescine, spermidine, or spermine) (including a host capable of incorporating these compounds from outside) has the following enzyme activities, gomphrenin-I-glucuronide can be synthesized.

Enzyme activity of hydroxylating the 3-position of the phenol ring of tyrosine, enzyme activity of having L-DOPA oxidase activity, enzyme activity of having DOPA 4,5-dioxygenase activity, betanidin-to-gomphrenin-I synthetase {betanidin 6-O-glucosyltransferase (6GT(B6GT)) enzyme}activity, and amaranthin or gomphrenin-I-glucuronide synthetase activity of the present invention.

According to the results of Example 7 to be described below, a plant body that is a host having introduced a gene group of a gene encoding an enzyme having activity of hydroxylating the 3-position of the phenol ring of tyrosine (gene encoding an enzyme having L-DOPA oxidase activity), a gene encoding an enzyme having betanidin-to-gomphrenin-I synthesis activity, a gene encoding an enzyme having DOPA 4,5-dioxygenase activity, and a gene encoding an amaranthin or gomphrenin-I-glucuronide synthetase of the present invention has an ability to synthesize gomphrenin-I-glucuronide, which is a betalain pigment.

As apparent from the illustrations in FIG. 1 and FIG. 2, the present invention also encompasses the following amaranthin synthesis method.

(1) Betanin is brought into contact with the amaranthin or gomphrenin-I-glucuronide synthetase of the present invention. As required, a metal ion is added.

(2) Betanidin is brought into contact with a betanidin-to-betanin synthetase to provide betanin, which is then brought into contact with the amaranthin or gomphrenin-I-glucuronide synthetase of the present invention. As required, a metal ion is added.

As apparent from the illustration in FIG. 16, the present invention also encompasses the following gomphrenin-I-glucuronide synthesis method.

(1) Gomphrenin-I is brought into contact with an amaranthin synthesis or gomphrenin-I-glucuronide synthesis composition of the present invention. As required, a metal ion is added.

(2) (a) A step of bringing betanidin into contact with a betanidin-to-gomphrenin-I synthetase is performed, and (b) the gomphrenin-I obtained in the step (a) is brought into contact with the amaranthin synthesis or gomphrenin-I-glucuronide synthesis composition of the present invention. As required, a metal ion is added.

(Enzyme for Hydroxylating 3-Position of Phenol Ring of Tyrosine)

The enzyme for hydroxylating the 3-position of the phenol ring of tyrosine in the present invention has activity of allowing a hydroxy group to be added to the 3-position of the phenol ring that tyrosine has, and the enzyme may be derived from any species as long as the enzyme has the activity.

Examples of the enzyme for hydroxylating the 3-position of the phenol ring of tyrosine include tyrosinase, cytochromes P450 (in particular, CYP76AD1, CYP76AD2, CYP76AD3, and the like), and catechol oxidase. Of those, CqCYP76AD1 (base sequence: SEQ ID NO: 13, amino acid sequence: SEQ ID NO: 14, accession number: XP_021769302) is preferred.

(Enzyme Having L-DOPA Oxidase Activity)

The enzyme having L-DOPA oxidase activity in the present invention has activity of converting L-DOPA into cyclo-DOPA, and may be derived from any species as long as the enzyme has the activity.

Examples of the enzyme having L-DOPA oxidase activity include tyrosinase and cytochromes P450, such as CYP76AD1, CYP76AD2, CYP76AD3, CYP76AD5, and CYP76AD6. Of those, CqCYP76AD1 (base sequence: SEQ ID NO: 13, amino acid sequence: SEQ ID NO: 14) is preferred.

(Enzyme for Glycosylating Phenolic Hydroxy Group)

The enzyme for glycosylating a phenolic hydroxy group in the present invention has activity of glycosylating a phenolic hydroxy group present at the 5-position or the 6-position of a cyclo-DOPA skeleton, and may be derived from any species as long as the enzyme has the activity.

Examples of the enzyme for glycosylating a phenolic hydroxy group include cyclo-DOPA5-O-glucosyltransferase, betanidin 5-O-glucosyltransferase (cyclo-DOPA 5-O-glucosyltransferase), and betanidin 6-O-glucosyltransferase. Of those, CqCDOPA5GT (base sequence: SEQ ID NO: 15, amino acid sequence: SEQ ID NO: 16, accession number: XP_021748306) is preferred.

(Betanidin-to-Betanin Synthetase)

The betanidin-to-betanin synthetase in the present invention is not particularly limited as long as betanin can be synthesized from betanidin, and examples thereof may include betanidin 5-O-glucosyltransferase (e.g., 5GT (B5GT)) and cyclo-DOPA 5-O-glucosyltransferase (CDOPA5GT).

(Betanidin-to-Gomphrenin-I Synthetase)

The betanidin-to-gomphrenin-I synthetase in the present invention is not particularly limited as long as gomphrenin-I can be synthesized from betanidin, and examples thereof may include betanidin 6-O-glucosyltransferase (e.g., 6GT (B6GT): SEQ ID NOS: 36 and 37) and cyclo-DOPA 6-O-glucosyltransferase (CDOPA6GT) (see: Substrate specificity and sequence analysis define a polyphyleticorigin of betanidin 5- and 6-O-glucosyltransferase from *Dorotheanthus bellidiformis*. planta 214, 492-495).

(Amaranthin or Gomphrenin-I-Glucuronide Synthetase)

The amaranthin or gomphrenin-I-glucuronide synthetase of the present invention may be derived from any species as long as the synthetase has activity of synthesizing amaranthin by bonding glucuronic acid to betanin (e.g., UDP-glucoronate (betanin beta-D-glucuronosyltransferase) or activity of synthesizing gomphrenin-I-glucuronide (in particular, gomphrenin-I-O-glucuronide) by bonding glucuronic acid to gomphrenin-I.

The gene encoding the amaranthin or gomphrenin-I-glucuronide synthetase (amaranthin synthetase gene or gomphrenin-I-glucuronide synthetase gene) of the present invention is any one or more selected from the following:

(1) a gene encoding a polypeptide formed of an amino acid sequence set forth in SEQ ID NO: 2, 4, 6, 8, 10, or 12;
(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;
(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;
(4) a gene formed of DNA formed of a base sequence set forth in SEQ ID NO: 1, 3, 5, 7, 9, or 11;
(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;
(6) a gene formed of DNA having a 1- to 50-base sequence substituted, deleted, inserted, and/or added in DNA formed of the base sequence set forth in SEQ ID NO: 1, 3, 5, 7, 9, or 11;
(7) a gene formed of DNA having 90% or more homology to DNA formed of the base sequence set forth in SEQ ID NO: 1, 3, 5, 7, 9, or 11; and
(8) a gene formed of DNA formed of a degenerate isomer of the base sequence set forth in SEQ ID NO: 1, 3, 5, 7, 9, or 11.

The gene of the above-mentioned item (2) is a gene encoding a polypeptide having introduced therein such a mutation as not to cause the loss of the ability to synthesize amaranthin or gomphrenin-I-glucuronide. Such mutation encompasses an artificial mutation as well as a naturally occurring mutation. As means for causing the artificial mutation, there may be given, for example, a site-directed mutagenesis method (Nucleic Acids Res. 10, 6487-6500, 1982). The number of mutated amino acids is generally 20 or less, preferably 10 or less, more preferably 5 or less, most preferably 3. Whether or not the polypeptide having introduced therein the mutation retains the ability to synthesize amaranthin or gomphrenin-I-glucuronide can be found by, for example, introducing a gene encoding the polypeptide having introduced therein the mutation into a plant body or the like, and checking the ability to synthesize amaranthin or gomphrenin-I-glucuronide in the plant body.

With regard to the gene of the above-mentioned item (3), the "substantially equivalent ability to synthesize amaranthin or gomphrenin-I-glucuronide to that of the amino acid sequence set forth in SEQ ID NO: 2, 4, 6, 8, 10, or 12" may be stronger or weaker in degree of the action as compared to the substantially equivalent ability to synthesize amaranthin or gomphrenin-I-glucuronide to that of the amino acid sequence set forth in SEQ ID NO: 2, 4, 6, 8, 10, or 12. The degree of the action may be, for example, about 50%, about 60%, about 70%, about 80%, about 90%, about 100%, about 110%, about 120%, about 130%, about 140%, or about 150% as compared to the ability of the amino acid sequence set forth in SEQ ID NO: 2, 4, 6, 8, 10, or 12 to synthesize amaranthin or gomphrenin-I-glucuronide.

In addition, the identity may be calculated using the Basic Local Alignment Search Tool at the National Center for Biological Information (BLAST) or the like (using, for example, default, namely initially set, parameters).

The gene of the above-mentioned item (5) is a gene obtained by utilizing hybridization between DNAs. The term "stringent conditions" in this gene refers to conditions under which only specific hybridization occurs and non-specific hybridization does not occur. Such conditions are generally conditions such as hybridization in a buffer containing 5×SSC and 1% SDS at 37° C. and washing treatment with a buffer containing 1×SSC and 0.1% SDS at 37° C., preferably conditions such as hybridization in a buffer containing 5×SSC and 1% SDS at 42° C. and washing treatment with a buffer containing 0.5×SSC and 0.1% SDS at 42° C., more preferably conditions such as hybridization in a buffer containing 5×SSC and 1% SDS at 65° C. and washing treatment with a buffer containing 0.2×SSC and 0.1% SDS at 65° C. Whether or not DNA obtained by utilizing hybridization encodes a polypeptide having activity can be found by, for example, introducing the DNA into a plant body or the like, and checking the ability of the plant body to synthesize amaranthin or gomphrenin-I-glucuronide. The DNA obtained by hybridization generally has high identity to the gene of the above-mentioned item (4) (SEQ ID NO: 1, 3, 5, 7, 9, or 11). The "high identity" refers to 90% or more identity, preferably 95% or more identity, more preferably 98% or more identity.

The gene of the above-mentioned item (6) is a gene formed of DNA having a 1- to 50-base sequence, preferably a 1- to 30-base sequence, more preferably a 1- to 20-base sequence, most preferably a 1- to 10-base sequence, even most preferably a 1- to 5-base sequence substituted, deleted, inserted, and/or added in DNA formed of the base sequence set forth in SEQ ID NO: 1, 3, 5, 7, 9, or 11.

The gene of the above-mentioned item (7) is a gene formed of DNA having 90% or more, preferably 93% or more, more preferably 95% or more, most preferably 98% or more identity to DNA formed of the base sequence set forth in SEQ ID NO: 1, 3, 5, 7, 9, or 11.

The enzyme having amaranthin or gomphrenin-I-glucuronide (in particular, gomphrenin-I-O-glucuronide) synthetase activity of the present invention has any one or more amino acid sequences selected from the following:

(1) an amino acid sequence set forth in SEQ ID NO: 2, 4, 6, 8, 10, or 12;

(2) an amino acid sequence that has 1 to 20 amino acids substituted, deleted, inserted, and/or added in the amino acid sequence set forth in SEQ ID NO: 2, 4, 6, 8, 10, or 12, and that forms a polypeptide having a substantially equivalent ability to synthesize amaranthin or gomphrenin-I-glucuronide to that of the amino acid sequence set forth in SEQ ID NO: 2, 4, 6, 8, 10, or 12; and (3) an amino acid sequence that has 90% or more homology to the amino acid sequence set forth in SEQ ID NO: 2, 4, 6, 8, 10, or 12, and that forms a polypeptide having a substantially equivalent ability to synthesize amaranthin or gomphrenin-I-glucuronide to that of the amino acid sequence set forth in SEQ ID NO: 2, 4, 6, 8, 10, or 12.

In the introduction of a mutation into a peptide, for example, a substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable from the viewpoint of preventing basic properties (e.g., physical properties, function, physiological activity, or immunological activity) of the peptide from being changed.

(Enzyme Having DOPA 4,5-Dioxygenase Activity)

The enzyme having DOPA 4,5-dioxygenase activity in the present invention has an ability to convert L-DOPA into 4,5-seco-DOPA through activity of catalyzing extradiol cleavage of L-3,4-dihydroxyphenylalanine. Further, 4,5-seco-DOPA converts into betalamic acid through a spontaneous reaction.

The gene encoding the enzyme having DOPA 4,5-dioxygenase activity in the present invention is any one or more selected from the following:

(1) a gene encoding a polypeptide formed of an amino acid sequence set forth in SEQ ID NO: 17 (accession number: XP 021769303), 19 (accession number: XP 021769301), 21, 23, 25, 27, or 34;

(2) a gene encoding a polypeptide that has 1 to 20 amino acids substituted, deleted, inserted, and/or added in the amino acid sequence set forth in SEQ ID NO: 17, 19, 21, 23, 25, 27, or 34, and that has a substantially equivalent ability to convert L-DOPA into 4,5-seco-DOPA to that of the amino acid sequence set forth in SEQ ID NO: 17, 19, 21, 23, 25, or 27;

(3) a gene encoding a polypeptide that has 90% or more homology to the amino acid sequence set forth in SEQ ID NO: 17, 19, 21, 23, 25, 27, or 34, and that has a substantially equivalent ability to convert L-DOPA into 4,5-seco-DOPA to that of the amino acid sequence set forth in SEQ ID NO: 17, 19, 21, 23, 25, 27, or 34;

(4) a gene formed of DNA formed of a base sequence set forth in SEQ ID NO: 18, 20, 22, 24, 26, 28, or 35;

(5) a gene formed of DNA that hybridizes with DNA formed of a base sequence complementary to DNA formed of the base sequence set forth in SEQ ID NO: 18, 20, 22, 24, 26, 28, or 35 under stringent conditions, and that encodes a polypeptide having an ability to convert L-DOPA into 4,5-seco-DOPA;

(6) a gene formed of DNA having a 1- to 50-base sequence substituted, deleted, inserted, and/or added in DNA formed of the base sequence set forth in SEQ ID NO: 18, 20, 22, 24, 26, 28, or 35;

(7) a gene formed of DNA having 90% or more homology to DNA formed of the base sequence set forth in SEQ ID NO: 18, 20, 22, 24, 26, 28, or 35;

(8) the gene of any one or more of the above-mentioned items (1) to (7) including a gene encoding a polypeptide formed of an amino acid sequence set forth in SEQ ID NO: 33; and (9) a gene formed of DNA formed of a degenerate isomer of the base sequence set forth in SEQ ID NO: 18, 20, 22, 24, 26, 28, or 35.

The gene of the above-mentioned item (2) is a gene encoding a polypeptide having introduced therein such a mutation as not to cause the loss of the ability to convert L-DOPA into 4,5-seco-DOPA. Such mutation may be introduced by the method described above.

With regard to the gene of the above-mentioned item (3), the "substantially equivalent ability to convert L-DOPA into 4,5-seco-DOPA to that of the amino acid sequence set forth in SEQ ID NO: 17, 19, 21, 23, 25, 27, or 34" may be stronger or weaker in degree of the action as compared to the ability of the amino acid sequence set forth in SEQ ID NO: 17, 19, 21, 23, 25, 27, or 34 to convert L-DOPA into 4,5-seco-DOPA. The degree of the action may be, for example, about 50%, about 60%, about 70%, about 80%, about 90%, about 100%, about 110%, about 120%, about 130%, about 140%, or about 150% as compared to the ability of the amino acid sequence set forth in SEQ ID NO: 17, 19, 21, 23, 25, 27, or 34 to convert L-DOPA into 4,5-seco-DOPA.

The gene of the above-mentioned item (5) is a gene obtained by utilizing hybridization between DNAs. DNA obtained by hybridization generally has high identity to the gene of the above-mentioned item (4) (SEQ ID NO: 18, 20, 22, 24, 26, 28, or 35). The "high identity" refers to 90% or more identity, preferably 95% or more identity, more preferably 98% or more identity.

The gene of the above-mentioned item (6) is a gene formed of DNA having a 1- to 50-base sequence, preferably a 1- to 30-base sequence, more preferably a 1- to 20-base sequence, most preferably a 1- to 10-base sequence, even most preferably a 1- to 5-base sequence substituted, deleted, inserted, and/or added in DNA formed of the base sequence set forth in SEQ ID NO: 18, 20, 22, 24, 26, 28, or 35.

The gene of the above-mentioned item (7) is a gene formed of DNA having 90% or more, preferably 93% or more, more preferably 95% or more, most preferably 98% or more identity to DNA formed of the base sequence set forth in SEQ ID NO: 18, 20, 22, 24, 26, 28, or 35.

The enzyme having DOPA 4,5-dioxygenase activity in the present invention is any one or more selected from the following:

(1) an amino acid sequence set forth in SEQ ID NO: 17, 19, 21, 23, 25, 27, or 34;

(2) an amino acid sequence that has 1 to 20 amino acids substituted, deleted, inserted, and/or added in the amino acid sequence set forth in SEQ ID NO: 17, 19, 21, 23, 25, 27, or 34, and that has a substantially equivalent ability to convert L-DOPA into 4,5-seco-DOPA to that of the amino acid sequence set forth in SEQ ID NO: 17, 19, 21, 23, 25, 27, or 34;

(3) an amino acid sequence that has 90% or more homology to the amino acid sequence set forth in SEQ ID NO: 17, 19, 21, 23, 25, 27, or 34, and that has a substantially equivalent ability to convert L-DOPA into 4,5-seco-DOPA to that of the amino acid sequence set forth in SEQ ID NO: 1; and (4) the amino acid sequence of any one or more of the above-mentioned items (1) to (3) including the amino acid sequence set forth in SEQ ID NO: 33.

In the introduction of a mutation into a peptide, for example, a substitution between homologous amino acids (e.g., polar amino acids, non-polar amino acids, hydrophobic amino acids, hydrophilic amino acids, positively charged amino acids, negatively charged amino acids, and aromatic amino acids) is easily conceivable from the viewpoint of preventing basic properties (e.g., physical properties, function, physiological activity, or immunological activity) of the peptide from being changed.

In particular, the amino acid sequence set forth in SEQ ID NO: 33 contains the sequence of an active site. When a mutation is introduced into this sequence, the ability to convert L-DOPA into 4,5-seco-DOPA is highly liable to be lost, and hence it is preferred that the mutation be introduced at an amino acid outside those domains.

(Synthesis Method for Betalain Pigment)

A synthesis method for a betalain pigment of the present invention may be exemplified by the following:

(1) culturing a host that has introduced therein a gene encoding an amaranthin or gomphrenin-I-glucuronide synthetase, a gene encoding an enzyme having activity of hydroxylating the 3-position of the phenol ring of tyrosine, a gene encoding an enzyme having L-DOPA oxidase activity, a gene encoding an enzyme having activity of glycosylating a phenolic hydroxy group, and a gene encoding an enzyme having DOPA 4,5-dioxygenase activity, and that has an ability to produce tyrosine or L-DOPA, and extracting a betalain pigment from the host after the culturing;

(2) culturing a host that has introduced therein a gene encoding an amaranthin or gomphrenin-I-glucuronide synthetase, a gene encoding an enzyme having activity of hydroxylating the 3-position of the phenol ring of tyrosine, a gene encoding an enzyme having L-DOPA oxidase activity, a gene encoding a betanidin-to-betanin synthetase, and a gene encoding an enzyme having DOPA 4,5-dioxygenase activity, and that has an ability to produce tyrosine or L-DOPA, and extracting a betalain pigment from the host after the culturing;

(3) culturing a host that has introduced therein a gene encoding an amaranthin or gomphrenin-I-glucuronide synthetase, and that has enzyme activity of having activity of hydroxylating the 3-position of the phenol ring of tyrosine, enzyme activity of having L-DOPA oxidase activity, enzyme activity of having activity of glycosylating a phenolic hydroxy group, enzyme activity of having DOPA 4,5-dioxygenase activity, and an ability to produce tyrosine or 3-hydroxy-L-tyrosine, and extracting a betalain pigment from the host after the culturing;

(4) culturing a host that has introduced therein a gene encoding an amaranthin or gomphrenin-I-glucuronide synthetase, and that has enzyme activity of having activity of hydroxylating the 3-position of the phenol ring of tyrosine, enzyme activity of having L-DOPA oxidase activity, enzyme activity of having betanidin-to-betanin synthesis activity, enzyme activity of having DOPA 4,5-dioxygenase activity, and an ability to produce tyrosine or 3-hydroxy-L-tyrosine, and extracting a betalain pigment from the host after the culturing;

(5) culturing a host that has introduced therein a gene encoding an amaranthin or gomphrenin-I-glucuronide synthetase, a gene encoding an enzyme having activity of hydroxylating the 3-position of the phenol ring of tyrosine, a gene encoding an enzyme having L-DOPA oxidase activity, a gene encoding a betanidin-to-gomphrenin-I synthetase, and a gene encoding an enzyme having DOPA 4,5-dioxygenase activity, and that has an ability to produce tyrosine or L-DOPA, and extracting a betalain pigment from the host after the culturing; or (6) culturing a host that has introduced therein a gene encoding an amaranthin or gomphrenin-I-glucuronide synthetase, and that has enzyme activity of having activity of hydroxylating the 3-position of the phenol ring of tyrosine, enzyme activity of having L-DOPA oxidase activity, enzyme activity of having betanidin-to-gomphrenin-I synthesis activity, enzyme activity of having DOPA 4,5-dioxygenase activity, and an ability to produce tyrosine or 3-hydroxy-L-tyrosine, and extracting a betalain pigment from the host after the culturing.

(Host)

The host to be used in the synthesis method for a betalain pigment of the present invention is not particularly limited as long as the host has an ability to produce tyrosine or 3-hydroxy-L-tyrosine. For example, there may be used a synthesis system known per se, such as a recombinant *Escherichia coli* protein synthesis system, an insect protein synthesis system, a yeast protein synthesis system, a plant cell protein synthesis system, a cell-free protein synthesis system, a plant protein synthesis system, or animal cultured cells.

A method known per se may be used as a method of introducing each gene into the host to be used in the synthesis method for a betalain pigment of the present invention. For example, the gene may be introduced into the host using a vector carrying the gene.

As the vector, a viral vector known per se, in particular, a plant virus vector (e.g., a vector derived from a virus belonging to the genus Tobamovirus, a tobacco mosaic virus vector, or a tomato mosaic virus vector) may be utilized.

In addition, an *Agrobacterium* method involving using a Ti plasmid may be utilized.

(Method of Introducing Each Gene into Host)

In the synthesis method for a betalain pigment of the present invention, with regard to the method of introducing each gene into the host, the gene may be introduced into a plant body by a method known per se. For example, each gene may be introduced into the host by applying a solution containing a plant virus vector carrying each gene to a leaf, a stalk, a root, an ear, or the like of the plant body. Other examples of the method may include a particle gun method and an *Agrobacterium* method.

(Method of Introducing Each Protein into Host)

In the synthesis method for a betalain pigment of the present invention, with regard to a method of introducing each protein into the host (in particular, a plant body), the protein may be introduced into the plant body by a method known per se. For example, each protein may be introduced into the host by applying a solution containing each protein to a leaf, a stalk, a root, an ear, or the like of the plant body.

Other examples of the method may include a particle gun method and an *Agrobacterium* method.

(Betalain Pigment-Producing Host)

A betalain pigment-producing host of the present invention has, for example, any one or more of the following configurations and features:

(1) the host has introduced therein a gene encoding an amaranthin or gomphrenin-I-glucuronide synthetase, a gene encoding an enzyme having activity of hydroxylating the 3-position of the phenol ring of tyrosine, a gene encoding an enzyme having L-DOPA oxidase activity, a gene encoding an enzyme having activity of glycosylating a phenolic hydroxy group, and a gene encoding an enzyme having DOPA 4,5-dioxygenase activity, and has an ability to produce tyrosine or 3-hydroxy-L-tyrosine (L-DOPA);

(2) the host has introduced therein a gene encoding an amaranthin or gomphrenin-I-glucuronide synthetase, a gene encoding an enzyme having activity of hydroxylating the 3-position of the phenol ring of tyrosine, a gene encoding an enzyme having L-DOPA oxidase activity, a gene encoding an enzyme having betanidin-to-betanin synthesis activity, and a gene encoding an enzyme having DOPA 4,5-dioxygenase activity, and has an ability to produce tyrosine or 3-hydroxy-L-tyrosine (L-DOPA);

(3) the host has introduced therein a gene encoding an amaranthin or gomphrenin-I-glucuronide synthetase, and has enzyme activity of having activity of hydroxylating the 3-position of the phenol ring of tyrosine, enzyme activity of having L-DOPA oxidase activity, enzyme activity of having activity of glycosylating a phenolic hydroxy group, enzyme activity of having DOPA 4,5-dioxygenase activity, and an ability to produce tyrosine or 3-hydroxy-L-tyrosine;

(4) the host has introduced therein a gene encoding an amaranthin or gomphrenin-I-glucuronide synthetase, and has enzyme activity of having activity of hydroxylating the 3-position of the phenol ring of tyrosine, enzyme activity of having L-DOPA oxidase activity, enzyme activity of having betanidin-to-betanin synthesis activity, enzyme activity of having DOPA 4,5-dioxygenase activity, and an ability to produce tyrosine or 3-hydroxy-L-tyrosine;

(5) the host has introduced therein a gene encoding an amaranthin or gomphrenin-I-glucuronide synthetase, a gene encoding an enzyme having activity of hydroxylating the 3-position of the phenol ring of tyrosine, a gene encoding an enzyme having L-DOPA oxidase activity, a gene encoding an enzyme having betanidin-to-gomphrenin-I synthesis activity, and a gene encoding an enzyme having DOPA 4,5-dioxygenase activity, and has an ability to produce tyrosine or 3-hydroxy-L-tyrosine (L-DOPA);

(6) the host has introduced therein a gene encoding an amaranthin or gomphrenin-I-glucuronide synthetase, and has enzyme activity of having activity of hydroxylating the 3-position of the phenol ring of tyrosine, enzyme activity of having L-DOPA oxidase activity, enzyme activity of having betanidin-to-gomphrenin-I synthesis activity, enzyme activity of having DOPA 4,5-dioxygenase activity, and an ability to produce tyrosine or 3-hydroxy-L-tyrosine; and (7) the host has introduced therein an amaranthin or gomphrenin-I-glucuronide synthesis composition.

(Amaranthin or Gomphrenin-I-Glucuronide Synthesis Composition)

An amaranthin or gomphrenin-I-glucuronide synthesis composition (amaranthin synthesis agent, amaranthin synthetase agent, gomphrenin-I-glucuronide synthesis agent, or gomphrenin-I-glucuronide synthetase agent) of the present invention contains a gene shown in any one of the following items (1) to (7) or a vector carrying the gene:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11;

(7) a gene formed of DNA having 90% or more homology to DNA formed of the base sequence set forth in SEQ ID NO: 1, 3, 5, 7, 9, or 11; and (8) a gene formed of DNA formed of a degenerate isomer of the base sequence set forth in SEQ ID NO: 1, 3, 5, 7, 9, or 11.

In addition, the amaranthin or gomphrenin-I-glucuronide synthesis composition of the present invention has a peptide represented by an amino acid sequence of any one of the following items (1) to (3):

(1) an amino acid sequence set forth in SEQ ID NO: 2, 4, 6, 8, 10, or 12;

(2) an amino acid sequence that forms a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12; and (3) an amino acid sequence that forms a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12.

(Therapeutic or Preventive Agent for Cancer)

A therapeutic or preventive agent for cancer of the present invention contains any one of the following items (1) to (4):

(1) amaranthin;

(2) amaranthin obtained by the synthesis method for a betalain pigment described herein;

(3) amaranthin obtained by the amaranthin synthesis method described herein; and (4) amaranthin obtained from the betalain pigment-producing host described herein.

The kind of cancer applicable to the therapeutic or preventive agent for cancer of the present invention is not particularly limited as long as the cancer is a malignant tumor. The therapeutic or preventive agent for cancer may be used for one kind or a plurality of kinds of cancers selected from liver cancer, pancreatic cancer, breast cancer, colorectal cancer, non-small cell lung cancer, small cell lung cancer, prostate cancer, stomach cancer, thyroid cancer, ovarian cancer, salivary gland adenoid cystic carcinoma, acute myeloid leukemia, acute lymphocytic leukemia, chronic lymphocytic leukemia, chronic myeloid leukemia, malignant lymphoma, myxoid liposarcoma, glioblastoma, alveolar rhabdomyosarcoma, Wilms' tumor, oligodendroglioma, adrenocortical carcinoma, multiple myeloma, medulloblastoma, endometrial cancer, esophageal cancer, and Ewing sarcoma. Of those, breast cancer is preferred.

(HIV-1 Protease Activity Inhibitor)

An HIV-1 protease activity inhibitor of the present invention contains any one of the following items (1) to (4):

(1) amaranthin;

(2) amaranthin obtained by the synthesis method for a betalain pigment described herein;

(3) amaranthin obtained by the amaranthin synthesis method described herein; and (4) amaranthin obtained from the betalain pigment-producing host described herein.

EXAMPLES

Now, the present invention is specifically described by way of Examples. However, the present invention is by no means limited to these Examples.

Examples 1 to 7 were carried out by the following methods.

[Homology Search and Phylogenetic Tree Analysis]

BLAST searches were performed for a *quinoa* genome, a beet genome, and an amaranth genome through utilization of the amino acid sequence of *Arabidopsis* flavonoid 3-O-glucoside:2"-O-glucosyltransferase (alternative name: UGT79B6, accession number: NP_200212).

A phylogenetic tree was constructed using amino acid sequences showing 40% or more homology according to the result of the BLAST searches and previously reported flavonoid-glycoside glycosyltransferases, using a neighbor-joining method with MAGA7 software (Table 1).

TABLE 1

Phylogenetic tree analysis list

| NCBI accession number | Gene name | Plant species |
|---|---|---|
| CAA50376 | Ph3RT | *Petunia hybrida* |
| ABA18631 | Cs1,6RhaT | *Citrus sinensis* |
| BAN91401 | GmF3G6"Rt | *Glycine max* |
| BAD95881 | IpA3G2"GT | *Ipomoea purpurea* |
| BAR88077 | GmF3G2"Gt | *Glycine max* |
| NP_200212 | AtF3G2"GT | *Arabidopsis thaliana* |
| BAD77944 | BpUGAT | *Bellis perennis* |
| BAH80312 | CaUGT3 | *Catharanthus roseus* |
| AAL06646 | Cm1,2RhaT | *Citrus maxima* |
| BAU68118 | ABRT2 | *Lobelia erinus* |
| BAU68119 | ABRT4 | *Lobelia erinus* |
| AAM13132 | AtUGT89C1 | *Arabidopsis thaliana* |
| AEC09298 | AtUGT73C6 | *Arabidopsis thaliana* |
| BAA83484 | SbUBGT | *Scutellaria baicalensis* |
| XP_021719267 | CqUGT79B6-like1 | *Chenopodium quinoa* |
| XP_021726554 | Cq3GGT-like1 | *Chenopodium quinoa* |
| XP_021731181 | CqUGT79B2-like | *Chenopodium quinoa* |
| XP_021735671 | CqUGT79B30-like1 | *Chenopodium quinoa* |
| XP_021735839 | Cq3GGT-like2 | *Chenopodium quinoa* |
| XP_021735840 | CqUGT79B30-like2 | *Chenopodium quinoa* |
| XP_021735841 | CqAmaSy2 (CqUGT79B30-like3) | *Chenopodium quinoa* |
| XP_021747968 | CqUGT79B6-like2 | *Chenopodium quinoa* |
| XP_021754077 | CqAmaSy1 (CqUGT79B30-like4) | *Chenopodium quinoa* |
| XP_021758620 | CqUGT79B30-like5 | *Chenopodium quinoa* |
| XP_021766006 | Cq3GGT-like3 | *Chenopodium quinoa* |
| XP_021773738 | CqUGT79B6-like3 | *Chenopodium quinoa* |
| XP_010695817 | Bv3GGT-like1 | *Beta vulgaris* |
| XP_010686377 | Bv3GGT-like2 | *Beta vulgaris* |
| XP_010666234 | BvUGT97B30-like | *Beta vulgaris* |
| XP_010674067 | BvUGT97B6-like1 | *Beta vulgaris* |
| XP_010675464 | BvUGT97B6-like2 | *Beta vulgaris* |
| **Phytozome accession number** | **Gene name** | **Plant species** |
| AH008037-RA | AhUGT79B6-like | *Amaranthus hypochondriacus* |
| AH008346-RA | AhUGT79B30-like1 | *Amaranthus hypochondriacus* |
| AH018627-RA | AhUGT79B30-like2 | *Amaranthus hypochondriacus* |
| AH018628-RA | AhUGT79B30-like3 | *Amaranthus hypochondriacus* |
| AH018629-RA | AhUGT79B30-like4 | *Amaranthus hypochondriacus* |

[Analysis of Expression in *Quinoa* Hypocotyls]

RNA was extracted from hypocotyls of *quinoa* (*Chenopodium quinoa*) on day 5 of germination through use of an RNeasy Plant Mini kit (Qiagen). A High Capacity cDNA Reverse Transcription Kit (Thermo Fisher Scientific) was used to synthesize cDNA from the extracted RNA. The procedure followed the accompanying instructions.

The synthesized cDNA was used as a template to amplify the full-length ORF of a betalain biosynthesis gene through PCR using the enzyme of Prime STAR GXL (TaKaRa). Primers used for the PCR are shown in Table 2. Primers Nos. 1 (SEQ ID NO: 38) and 2 (SEQ ID NO: 39) were used for Cq3GGT-like1, Primers Nos. 3 (SEQ ID NO: 40) and 4 (SEQ ID NO: 41) were used for Cq3GGT-like3, Primers Nos. 5 (SEQ ID NO: 42) and 6 (SEQ ID NO: 43) were used for Cq3GGT-like2, Primers Nos. 7 (SEQ ID NO: 44) and 8 (SEQ ID NO: 45) were used for CqUGT79B30-like2, Primers Nos. 9 (SEQ ID NO: 46) and 10 (SEQ ID NO: 47) were used for CqAmaSy2, Primers Nos. 11 (SEQ ID NO: 48) and 12 (SEQ ID NO: 49) were used for CqAmaSy1, Primers Nos. 13 (SEQ ID NO: 50) and 14 (SEQ ID NO: 51) were used for CqUGT79B30-like1, and Primers Nos. 15 (SEQ ID NO: 52) and 16 (SEQ ID NO: 53) were used for CqUGT79B30-like5. As a positive control, CqCYP76AD1 was amplified using Primers Nos. 17 (SEQ ID NO: 54) and 18 (SEQ ID NO: 55).

TABLE 2

| Quinoa hypocotyl expression | | |
|---|---|---|
| Primer No. | Gene name | Base sequence |
| 1(SEQ ID NO: 38) | Cq3GGT-like1 | ATGTCCAAGGAAAATGGCATTGCCAATGGC |
| 2(SEQ ID NO: 39) | | TCATACGAGAATACCTTTCAGACTCTGTAT |
| 3(SEQ ID NO: 40) | Cq3GGT-like3 | ATGTCCAAGGAAAATGGCATTGCTAATGGCAAT |
| 4(SEQ ID NO: 41) | | TTATACGAGAATGTCTTTCAGACTCTGTATGAACC |
| 5(SEQ ID NO: 42) | Cq3GGT-like2 | ATGTCATCATCAAACAATAACAATGGCAAGACTT |
| 6(SEQ ID NO: 43) | | TCAAACCAAATCTTGTAGACTTTGAACAAACTT |
| 7(SEQ ID NO: 44) | CqUGT79B30-like2 | ATGTCAAAGATTAACGAAACCAATGAATGT |
| 8(SEQ ID NO: 45) | | TCAAACCAAATCTTGTAGACTTTGAACAAACTT |
| 9(SEQ ID NO: 46) | CqAmaSy2 | ATGTCACAAAACAAAGACACCCAAATTCTA |
| 10(SEQ ID NO: 47) | | TCATGATCCAATCAATTGTTGCAAACTCATA |
| 11(SEQ ID NO: 48) | CqAmaSy1 | ATGTCACAAAACAAAGACAACCAAA |
| 12(SEQ ID NO: 49) | | TTATGATCCTATCAATTGTTGCAAACTCTG |
| 13(SEQ ID NO: 50) | CqUGT79B30-like1 | ATGTCTAACAACAAAAACTCCAAAATTCTAAAAG |
| 14(SEQ ID NO: 51) | | TCACTCAAGCAACTTTTGTAGATTATAAATGAAGC |
| 15(SEQ ID NO: 52) | CqUGT79B30-like5 | ATGGATAAAAAAATAGCAAGTATGGTTGAGGAAAAAG |
| 16(SEQ ID NO: 53) | | TCATGTAACTAGATCTAGTAGATTTTCAACA |
| 17(SEQ ID NO: 54) | CqCYP76AD1-1 | ATGGATCATGCAACACTAGCAATGAT |
| 18(SEQ ID NO: 55) | | TCAATACCTAAGAACGGGAATAATCT |

[Generation of Plasmids for Plant Expression]

For the expression of betalain pigment biosynthesis genes used in this experiment, a pCAMBIA1301 modification vector (Imamura, T., Takagi, H., Miyazato, A., Ohki, S., Mizukoshi, H. and Mori, M. (2018) Isolation and characterization of the betalain biosynthesis gene involved in hypocotyl pigmentation of the allotetraploid *Chenopodium quinoa*. Biochem. Biophys. Res. Commun. 496, 280-286) was used. For betalain pigment-associated synthesis genes, a fragment in which restriction enzyme sites were added to the 5' and 3' ends of each gene was synthesized by PCR. Then, the resultant PCR fragment was cleaved at the added sites and inserted into the plant modification vector to construct a plant expression vector.

[Analysis of Three-Dimensional Structure of Amaranthin Synthetase]

The Phyre2 web server (Kelley, L. A., Mezulis, S., Yates, C. M., Wass, M. N. and Sternberg, M. J. (2015) The Phyre2 web portal for protein modeling, prediction and analysis. Nat. Protoc. 10, 845-858) was used for the prediction of the three-dimensional structure of the amaranthin synthetase. UDP-glucosyltransferase (PDB code; 5NLM) was utilized as a protein for modeling.

[*Agrobacterium* Transformation Method]

The constructed plasmid was introduced from *Escherichia coli* harboring the plasmid into *Agrobacterium* using a triparental mating method (Wise, A. A., Liu, Z. and Binns, A. N. (2006) Three methods for the introduction of foreign DNA into *Agrobacterium. Methods Mol. Biol.* 343, 43-53) to generate a transformed *Agrobacterium.*

[Analysis of Transient Expression in *Nicotiana benthamiana*]

The plasmid harbored by the transformed *Agrobacterium* was introduced into green leaves of *Nicotiana benthamiana* through use of an agroinfiltration method (Shamloul, M., Trusa, J., Mett, V. and Yusibov, V. (2014) Optimization and utilization of *Agrobacterium*-mediated transient protein production in *Nicotiana*. Journal of visualized experiments: JoVE.). Inoculated and grown green leaves were utilized for analysis.

[Analysis of Constitutive Expression in Tobacco BY2 Cells]

The plasmid harbored by the transformed *Agrobacterium* was introduced into tobacco BY2 cells through use of an *Agrobacterium* method (Hagiwara, Y., Komoda, K., Yamanaka, T., Tamai, A., Meshi, T., Funada, R., Tsuchiya, T., Naito, S. and Ishikawa, M. (2003) Subcellular localization of host and viral proteins associated with tobamovirus RNA replication. EMBO J. 22, 344-353). The resultant transformed line was maintained and utilized for analysis.

[Betalain Pigment Extraction and HPLC Analysis]

The transformed plant sample was disrupted, and water was added, followed by centrifugation (20,000 g, 10 minutes or 15 minutes). The centrifuged supernatant was collected, and an equal amount of acetonitrile was added, followed by further centrifugation (20,000 g, 10 minutes or 15 minutes). The supernatant obtained by the centrifugal operation was concentrated with a centrifugal concentrator (CC-105, Tomy Seiko). The resultant concentrate was subjected to HPLC analysis as a pigment extract.

The HPLC analysis was performed by: using a reversed-phase column (Shim-pack GWS C18 column, 5 μm; 200×

4.6 mm i.d.; Shimadzu GLC); using 0.05% TFA in water as solvent A and 0.05% TFA in acetonitrile as solvent B; setting a flow rate to 0.5 ml/min; setting an analysis program to such a condition that the concentration of acetonitrile was linearly changed from 0% at an analysis time of 0 minutes to reach 45% over 45 minutes; and setting an analytical wavelength to 536 nm allowing betacyanin to be detected.

The purified betalain pigments were subjected to measurement with a UV-2450 spectrophotometer (Shimadzu), followed by the calculation of the concentrations of solutions using the molar extinction coefficient of amaranthin and betanin (ε=54,000 $M^{-1}$ $cm^{-1}$ at 536 nm) (Gandía-Herrero, F., Escribano, J. and García-Carmona, F. (2010) Structural implications on color, fluorescence, and antiradical activity in betalains. Planta 232, 449-460; Schwartz, S. J. and Von Elbe, J. H. (1980) Quantitative determination of individual betacyanin pigments by high-performance liquid chromatography. J. Agric. Food Chem. 28, 540-543).

[Influence of Betalain Pigment on Human Breast Cancer Cells]

Human breast cancer cells (MCF-7) were received from the RIKEN BioResource Center. For the culture of the cells, Dulbecco's modified Eagle's medium-high glucose (4.5 g $L^{-1}$ glucose; DMEM-HG) supplemented with 10% FBS and antibiotics (100 U $mL^{-1}$ penicillin and 100 μg $mL^{-1}$ streptomycin) was used. The cells were cultured under the culture conditions of 37° C., a humidity of 100%, and a 5% $CO_2$/95% air atmosphere. For the culture, the breast cancer cells were added at 5,000 cells per well on 96-well plates, and at the same time, amaranthin or betanin was added at different concentrations, and the cells were cultured for 72 hours. After that, the activity of the breast cancer cells was evaluated by an AlamarBlue assay (alamarBlue Cell Viability Reagent, Thermo Fisher Scientific). The procedure followed the accompanying instructions.

[Evaluation of HIV-1 Protease Inhibitory Activity of Betalain Pigment]

A recombinant HIV-1 protease (ab84117) from Abcam was used as an HIV-1 protease, and an HIV-1 protease substrate (Lys-Ala-Arg-Val-Nle-p-nitro-Phe-Glu-Ala-Nle amide) from Sigma-Aldrich was used as a substrate peptide for the HIV-1 protease. HIV-1 protease activity evaluation was performed with reference to a previously reported method (Boso, G., Orvell, C. and Somia, N. V. (2015) The nature of the N-terminal amino acid residue of HIV-1 RNase H is critical for the stability of reverse transcriptase in viral particles. J. Virol. 89, 1286-1297). Amaranthin or betanin was added to 16 pmol of the HIV-1 protease and 4 nmol of the HIV-1 protease substrate, a buffer (25 mM NaCl, 25 mM $Na_2HPO_4$, 1 mM dithiothreitol, pH 4.7) was added so that the amount of a reaction liquid was 30 μl, and a reaction was performed at 25° C. for 2 hours. With regard to the addition amount of amaranthin or betanin, amaranthin and betanin were each added at the ratios of 0-, 10-, 50-, and 100-fold amounts with respect to the amount of the HIV-1 protease.

After the reaction, the reaction liquid was measured for the amount of the residual substrate peptide through use of HPLC, and a residual ratio with respect to the substrate before the reaction was calculated. For the HPLC, LC-20AD from Shimadzu was utilized, and a Shim-pack GWS C18 column (5 μm; 200×4.6 mm i.d.; Shimadzu GLC) was used as an analytical column. For an analytical solvent system, 0.05% TFA in water was used as solvent A and 0.05% TFA in acetonitrile was used as solvent B. An HPLC program was set to a linear gradient from 0% of solvent B at 0 minutes to 50% of solvent B at 50 minutes, and the HPLC was performed at a flow rate of 0.5 mL/min and 25° C. Analysis was performed with an analytical wavelength being set to 260 nm allowing the HIV-1 protease substrate peptide to be detected.

Example 1

[Search for Amaranthin Synthetase Gene]

Figure 3A:
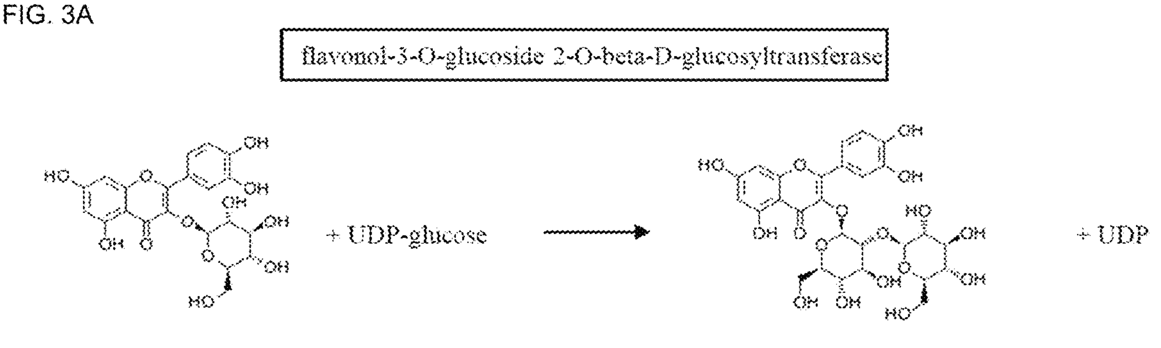
FIG. 3A is an illustration of a quercetin 3-O-beta-glucosyl-(1→2)-beta-glucoside synthesis reaction.
Figure 3B:
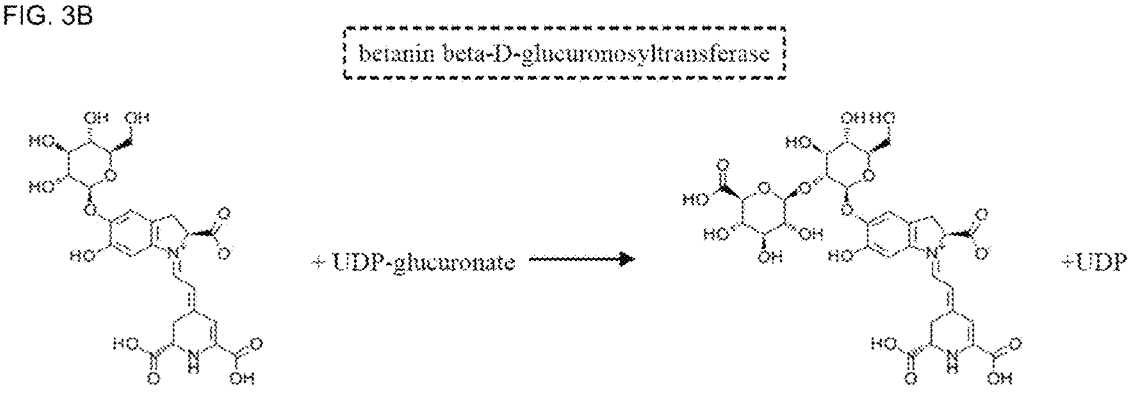
FIG. 3B is an illustration of an amaranthin synthesis reaction. The box and the dashed box indicate identified and predicted enzymes, respectively.

Amaranthin is a substance in which glucuronic acid is β-1,2-linked to glucose present in the molecule of betanin (FIG. 1 and FIG. 3B). In a flavonoid, another plant pigment, an enzyme that adds glucose to a flavonoid glucoside via a β-1,2 linkage has already been isolated (FIG. 3). In view of this, the amino acid sequence of *Arabidopsis* flavonoid 3-O-glucoside:2"-O-glucosyltransferase (alternative name: UGT79B6, accession number: NP_200212) was utilized to select homologous proteins from the *quinoa* genome.

(Homology Search and Phylogenetic Tree Analysis)

In order to isolate an amaranthin-synthesizing gene from the *quinoa* genome, candidate genes were narrowed down on the basis of homology search and phylogenetic tree analysis.

(Results)

Figure 4:
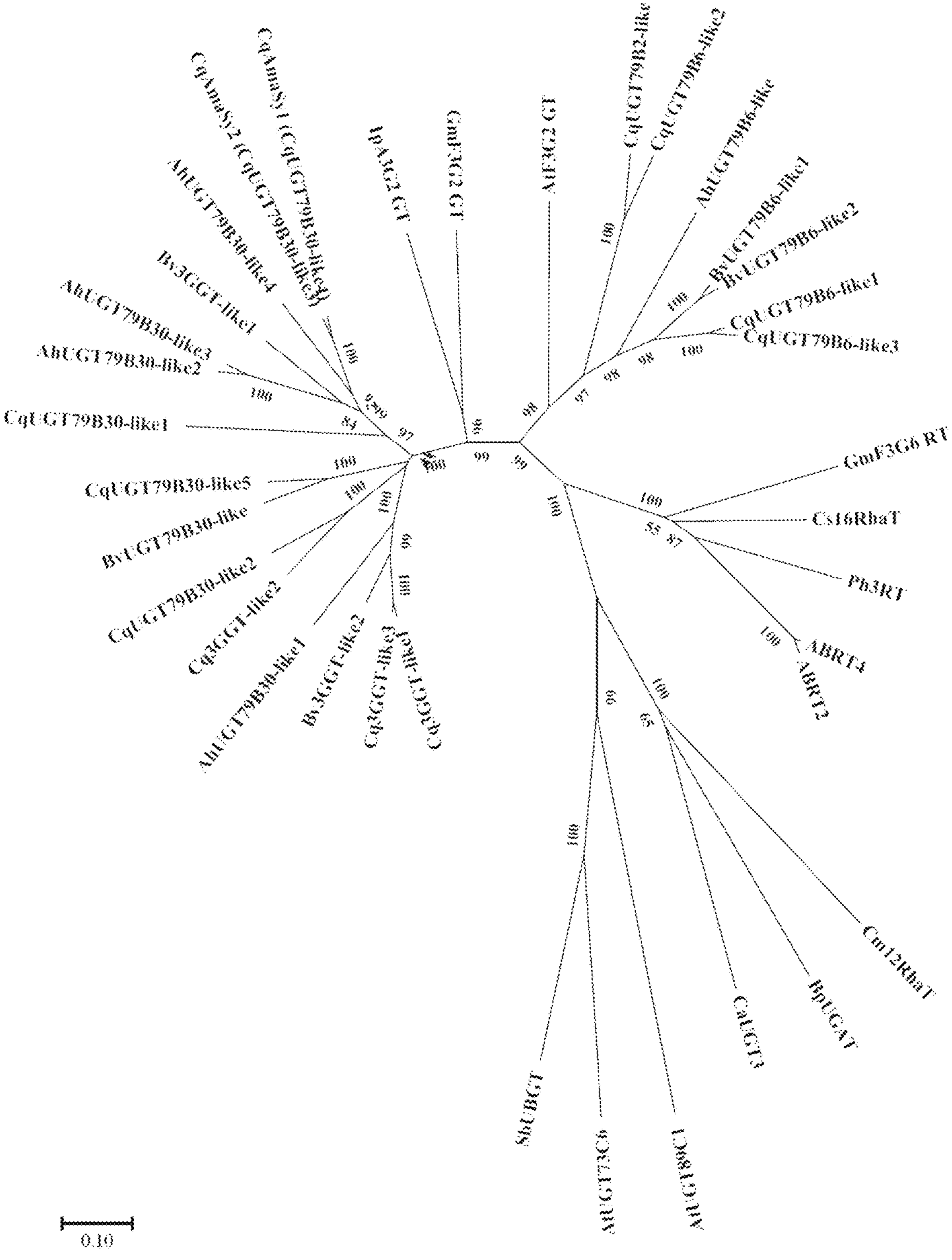
FIG. 4 is a molecular phylogenetic tree of flavonoid glycosyltransferases based on amino acid sequences. A plurality of sequences were aligned using MUSCLE and were used for phylogenetic tree construction by a maximum likelihood method using MEGA7. Bootstrap values from 5,000 replicates are shown on branches. The bar represents 0.1 amino acid substitutions per site. CqAmaSy1 and CqUGT79B30-like1 represent genes expressed in *quinoa* hypocotyls. CqAmaSy2, AhUGT79B30-like4, Bv3GGT-like1, AhUGT79B30-like3, and AhUGT79B30-like2 represent an amaranthin synthetase cluster. Details of flavonoid glycosyltransferase homologs from other plant species are shown in Table 1. Abbreviations for species: Ah represents *Amaranthus hypochondriacus*, At represents *Arabidopsis thaliana*, Bp represents *Bellis perennis*, By represents *Beta vulgaris*, Ca represents *Catharanthus roseus*, Cm represents *Citrus Maxima*, Cq represents *Chenopodium quinoa*, Cs represents *Citrus sinensis*, Gm represents *Glycine max*, Ip represents *Ipomoea purpurea*, Ph represents *Petunia hybrida*, and Sb represents *Scutellaria baicalensis*.

According to the results of selecting, from the *quinoa* genome, proteins having amino acid sequences homologous to *Arabidopsis* flavonoid 3-O-glucoside:2"-O-glucosyltransferase, there were twelve proteins showing 40% or more homology. Further, as betalain-producing Amaranthaceae plants, beets and amaranth were similarly analyzed, and as a result, it was found that there were six and four such proteins in beets and amaranth, respectively. Phylogenetic tree analysis was performed for those selected genes and flavonoid glycosyltransferases (Table 1). As a result, four of the candidates in *quinoa* (CqUGT79B2-like, CqUGT79B6-like2, CqUGT79B6-like1, and CqUGT79B6-like3) belonged to the existing group of the flavonoid glycosyltransferases. Meanwhile, the remaining eight candidates (CqAmaSy1, CqAmaSy2, CqUGT79B30-like1, CqUGT79B30-like5, CqUGT79B30-like2, Cq3GGT-like2, Cq3GGT-like3, and Cq3GGT-like1) formed a novel group (FIG. 4). The novel group was formed only of candidates in the Amaranthaceae plants, to which three candidates in beets and four candidates in amaranth belonged (FIG. 4). It was predicted from the phylogenetic tree analysis that the novel group was different in function from the heretofore reported enzymes for flavonoids.

(Analysis of Expression in *Quinoa* Hypocotyls)

On the basis of the accumulation of amaranthin in *quinoa* seedlings, it was predicted that candidate genes for synthesizing amaranthin were expressed in *quinoa* hypocotyls. In view of this, the eight candidates that belonged to a novel group according to the phylogenetic tree analysis were examined for gene expression in *quinoa* seedlings by RT-PCR method.

(Results)

Figure 5:
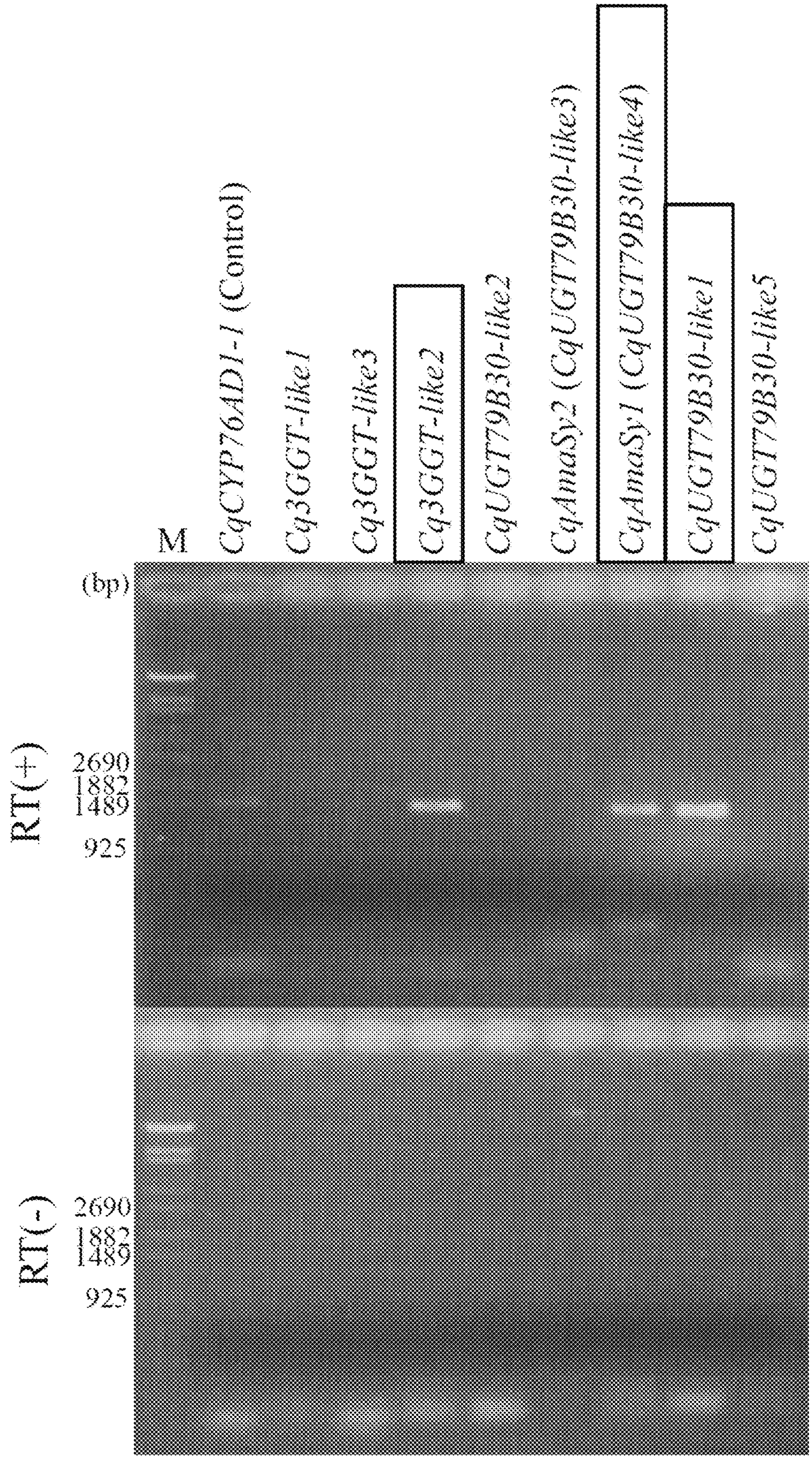
FIG. 5 shows the results of expression analysis of candidate genes involved in amaranthin synthesis. RT-PCR analysis of candidate gene expression in *quinoa* hypocotyls. (Upper panel) RT(+) represents reverse-transcribed samples. (Lower panel) RT(−) represents the corresponding controls containing no reverse transcriptase. Boxes indicate genes expressed in *quinoa* hypocotyls.

According to the results of the examination of gene expression in *quinoa* seedlings by the RT-PCR method, three candidate genes were expressed in *quinoa* seedlings (FIG. 5).

(Analysis of Transient Expression in *Nicotiana benthamiana*)

Figure 6:
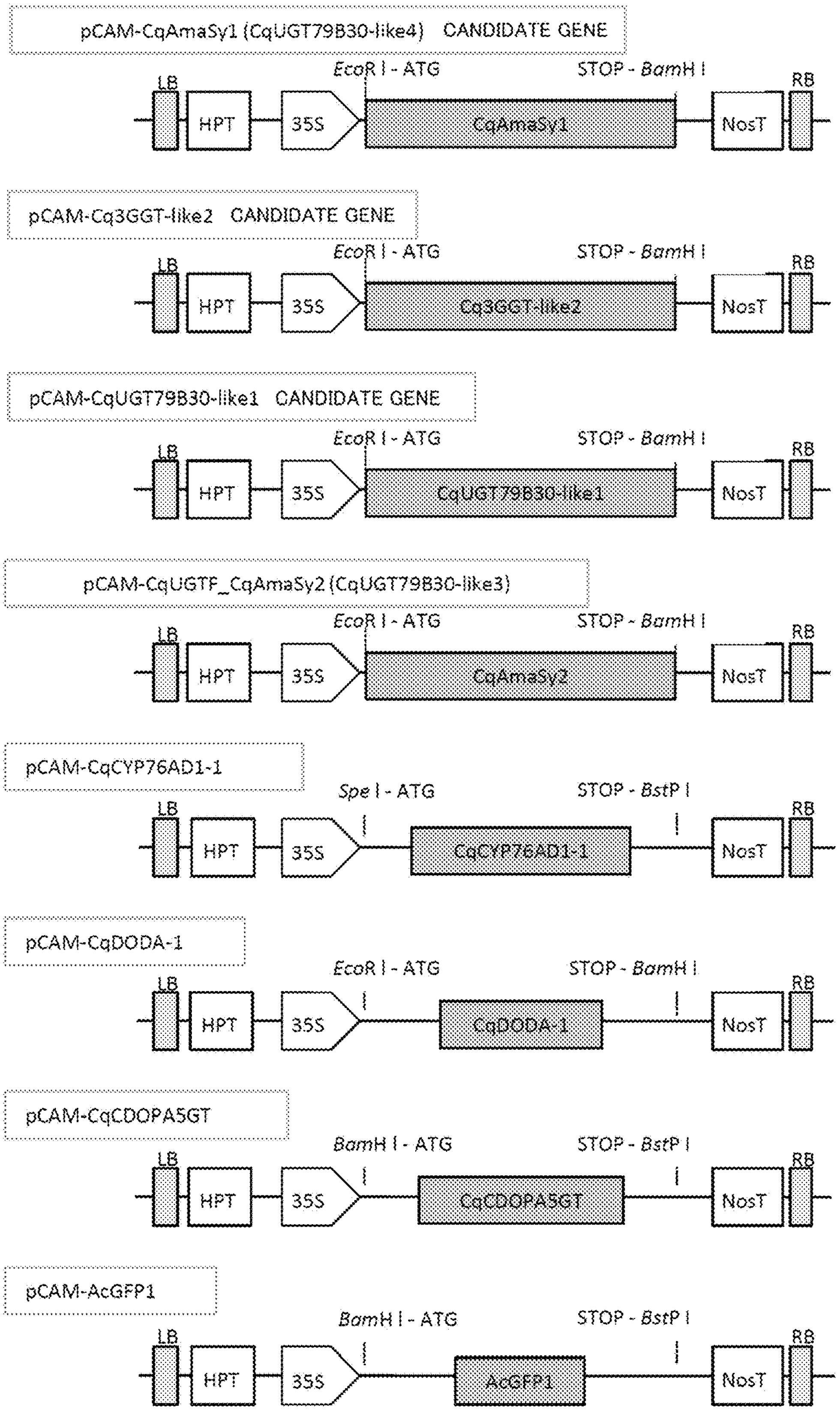
FIG. 6 includes schematic diagrams of plant expression vectors. CqAmaSy1 represents CqAmaSy1 CDS, CqAmaSy2 represents CqAmaSy2 CDS, Cq3GGT-like2 represents Cq3GGT-like2 CDS, CqUGT79B30-like1 represents CqUGT79B30-like1 CDS, CqCYP76AD1-1 represents CqCYP76AD1-1 CDS, CqDODA-1 represents CqDODA-1 CDS, CqCDOPA5GT represents CqCDOPA5GT CDS, AcGFP1 represents AcGFP1 CDS, 35S represents a CaMV 35S promoter, NosT represents a nopaline synthase terminator, RB represents a right border, and LB represents a left border. HPT represents a hygromycin phosphotransferase expression cassette, ATG represents a start codon, and STOP represents a stop codon.

In recent years, it has been reported that betalains can be produced by introducing betalain biosynthesis genes into non-betalain-producing plants, such as tobacco, eggplant, potato, and tomato (Polturak, G., Grossman, N., Vela-Corcia, D., Dong, Y., Nudel, A., Pliner, M., Levy, M., Rogachev, I. and Aharoni, A. (2017) Engineered gray mold resistance, antioxidant capacity, and pigmentation in betalain-producing crops and ornamentals. Proc. Natl. Acad. Sci. U.S.A 114, 9062-9067). The inventors of the present invention have also succeeded in producing betanin, which is a precursor of amaranthin, by expressing the betalain biosynthesis gene of *quinoa* in *Nicotiana benthamiana* (Imamura, T., Takagi, H., Miyazato, A., Ohki, S., Mizukoshi, H. and Mori, M. (2018) Isolation and characterization of the betalain biosynthesis gene involved in hypocotyl pigmentation of the allotetraploid *Chenopodium quinoa*. Biochem. Biophys. Res. Commun. 496, 280-286). In view of this, through utilization of the betalain production system in *Nicotiana benthamiana*, vectors for the three candidates that were expressed in the hypocotyls were constructed (FIG. 6), and whether the candidates possessed an ability to produce amaranthin was evaluated with an expression system using *Nicotiana benthamiana.*

(Results)

Figure 7B:
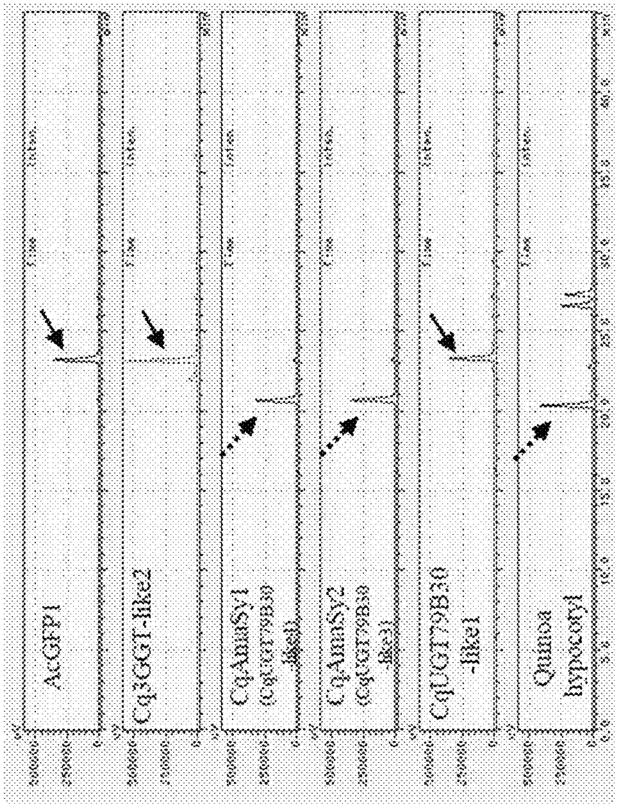
FIG. 7B includes HPLC chromatograms of infected *N. benthamiana* leaf extracts. Hypocotyl indicates the extract of the *quinoa* hypocotyl from CQ127 variety. Dashed and solid arrows indicate amaranthin and betanin, respectively. The horizontal axis indicates the retention time (min). The vertical axis indicates the signal intensity (μV).
Figure 7A:
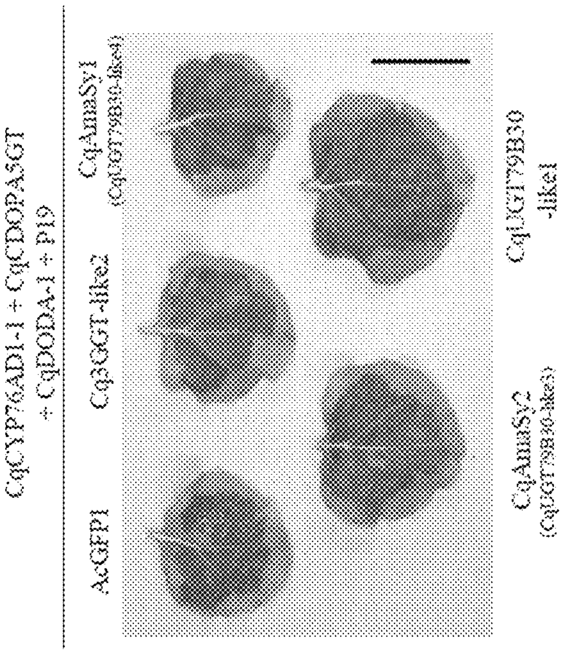
FIG. 7A: recombinant expression of candidate genes for amaranthin synthases (Cq3GGT-like2, CqAmaSy1 (CqUGT79B30-like4), CqAmaSy2 (CqUGT79B30-like3), and CqUGT79B30-like1) in *N. benthamiana* leaves. Co-infiltration of transgenic *Agrobacterium* harboring plasmids for the expression of candidate genes using CqCYP76AD1-1, CqCDOPA5GT, CqDODA-1, and P19. AcGFP1 is a negative control. The bar represents 4 cm.
Figure 7C:
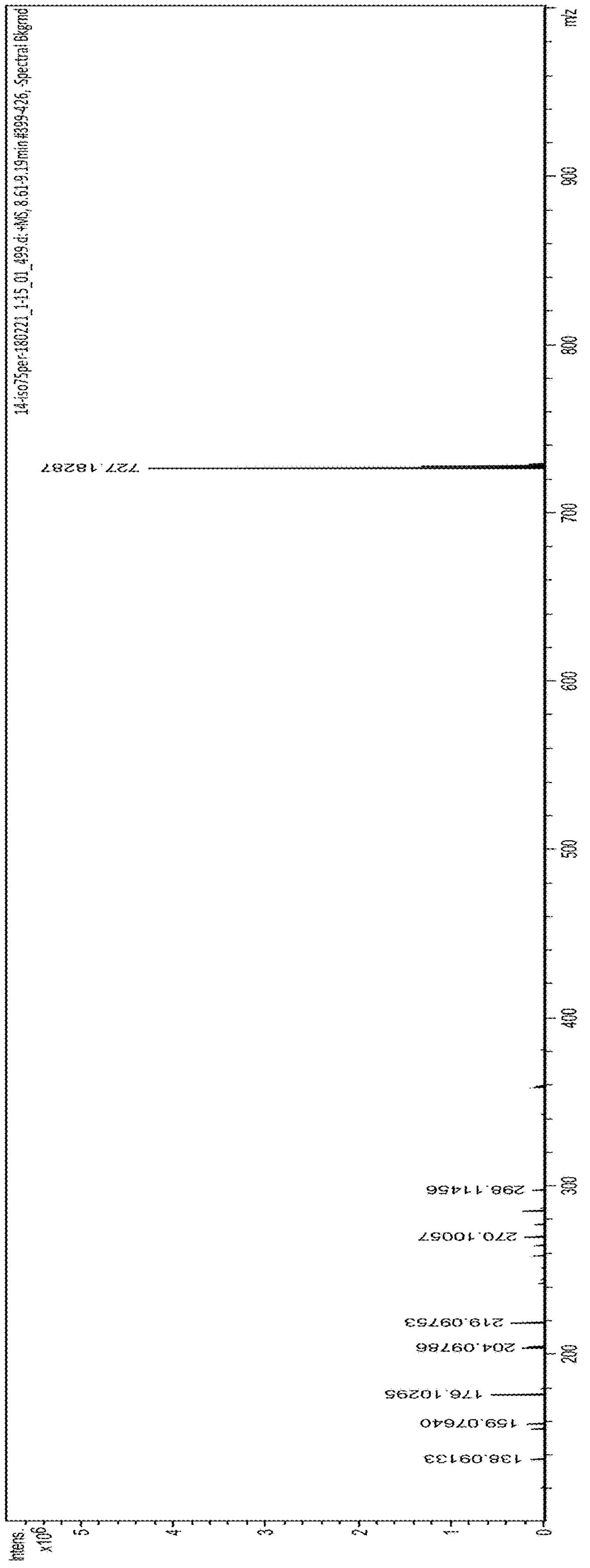
FIG. 7C includes MS spectra of HPLC elution samples from *N. benthamiana* leaf extracts. The upper and lower panels indicate HPLC elution samples at 21 min (dashed arrows in b) and 24 min (solid arrows in b), respectively. HPLC elution samples at 21 min and 24 min indicate amaranthin and betanin, respectively. The horizontal axis indicates the mass-to-charge ratio (m/z). The vertical axis indicates the relative abundance.

Red pigments produced in *Nicotiana benthamiana* were subjected to HPLC and MS analysis, and as a result, it was revealed that one candidate (accession number: XM_021898386) had an ability to produce amaranthin (FIG. 7).

On the basis of the above-mentioned results, the candidate gene having an amaranthin synthesis ability was named amaranthin synthetase {Amaranthin synthetase 1 (AmaSy1, accession number: XP_021754077, base sequence: SEQ ID NO: 1, amino acid sequence: SEQ ID NO: 2)}.

*Quinoa* is an allotetraploid plant, and hence it was predicted that it was highly likely that there was a homolog of AmaSy1. In view of this, a homology search was performed with respect to AmaSy1, and as a result, one gene (accession number: XM_021880149) was obtained. This homolog was evaluated for an ability to produce amaranthin through use of an expression system using *Nicotiana benthamiana*, and as a result, was revealed to have an ability to synthesize amaranthin (FIG. 7). In view of this, this gene was named Amaranthin synthetase 2 (AmaSy2, accession number: XP_021735841, base sequence: SEQ ID NO: 3, amino acid sequence: SEQ ID NO: 4).

Further, a search for orthologs of Amaranthin synthetase was also made for other Amaranthaceae plants producing betalains, and as a result, there were: one ortholog in beets {Bv3GGT-like1 (accession number: XP_010695817, base sequence: SEQ ID NO: 5, amino acid sequence: SEQ ID NO: 6)}; and three orthologs in amaranth {AhUGT79B30-like3 (Phytozome accession number: AH018628-RA, base sequence: SEQ ID NO: 7, amino acid sequence: SEQ ID NO: 8), AhUGT79B30-like4 (Phytozome accession number: AH018629-RA, base sequence: SEQ ID NO: 9, amino acid sequence: SEQ ID NO: 10), and AhUGT79B30-like2 (Phytozome accession number: AH018627-RA, base sequence: SEQ ID NO: 11, amino acid sequence: SEQ ID NO: 12)}.

Figure 8:
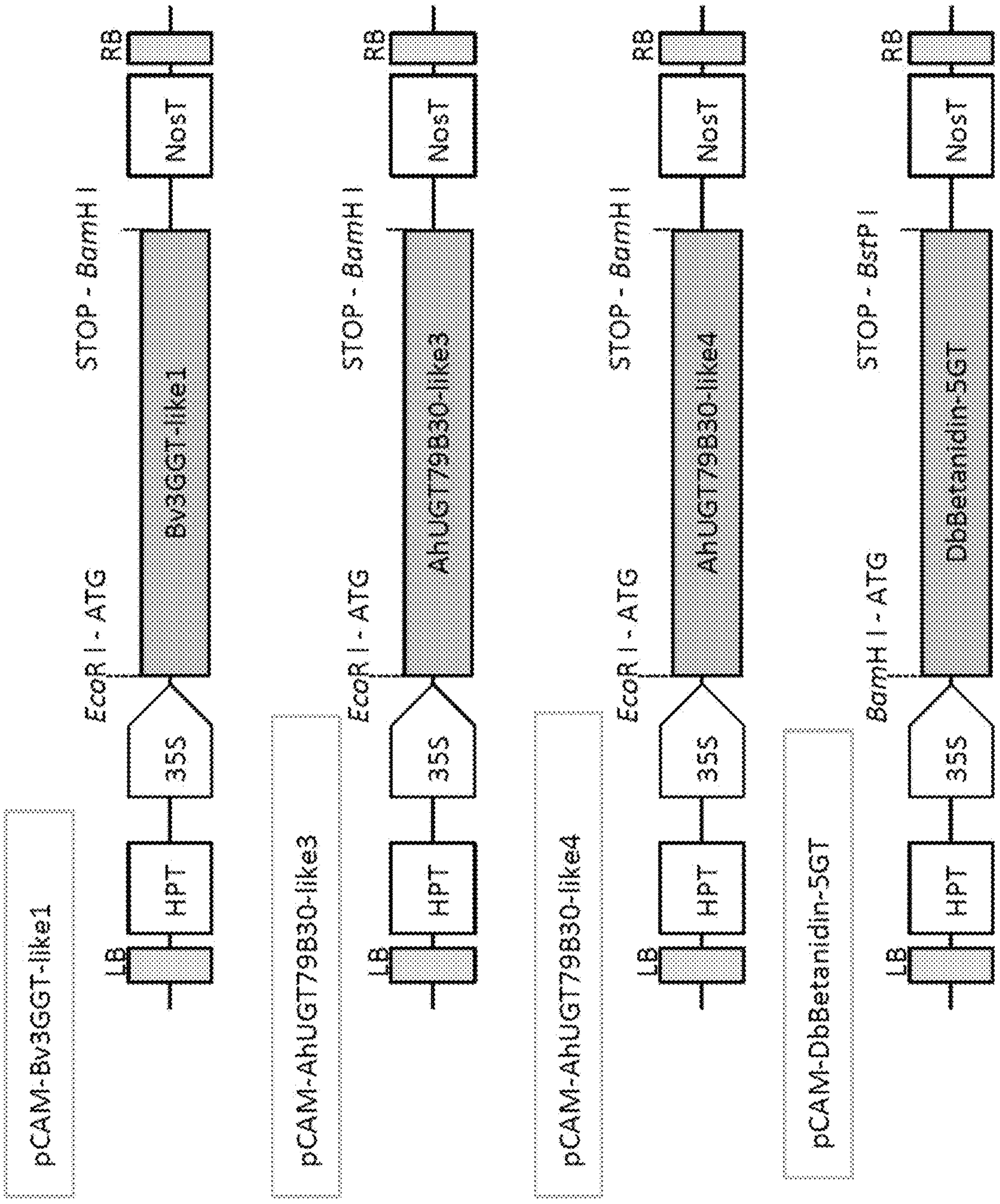
FIG. 8 includes schematic diagrams of plant expression vectors. Bv3GGT-like1 represents Bv3GGT-like1 CDS, AhUGT79B30-like3 represents AhUGT79B30-like3 CDS, AhUGT79B30-like4 represents AhUGT79B30-like4 CDS, DbBetanidin-15GT represents Dbbetanidin-5GT CDS, 35S represents a CaMV 35S promoter, NosT represents a nopaline synthase terminator, RB represents a right border, and LB represents a left border. HPT represents a hygromycin phosphotransferase expression cassette, ATG represents a start codon, and STOP represents a stop codon. Abbreviations for species: Ah represents *Amaranthus hypochondriacus*, By represents *Beta vulgaris*, and Db represents *Dorotheanthus bellidiformis.*
Figure 9A:
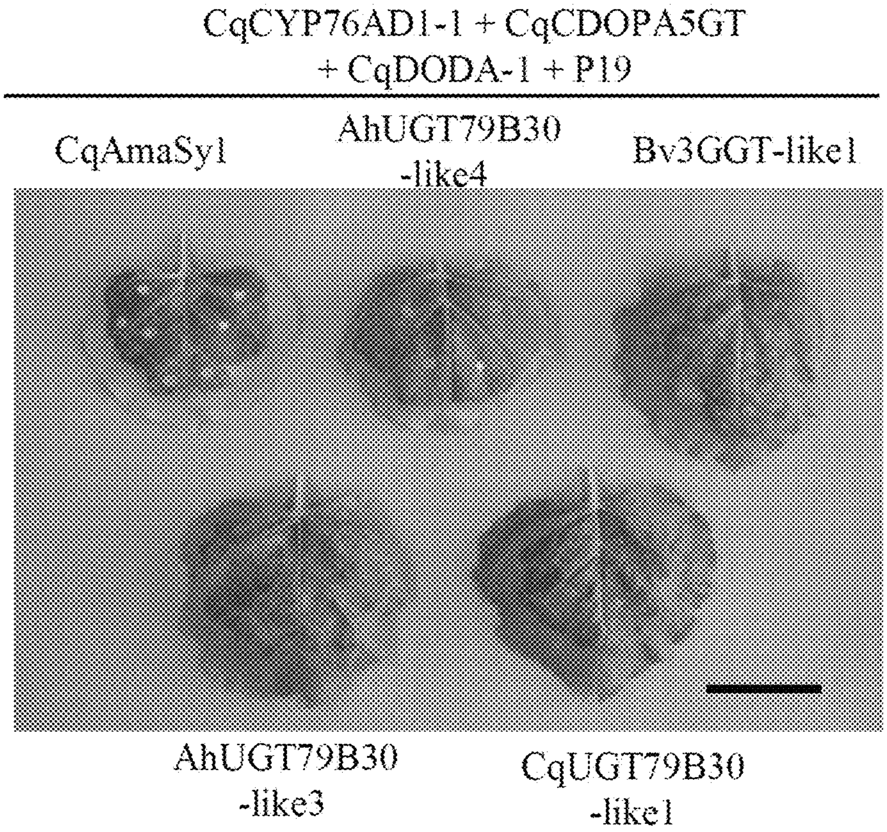
FIG. 9A: recombinant expression of candidate genes for amaranthin synthetase genes (Bv3GGT-like1, AhUGT79B30-like3, and AhUGT79B30-like4), CqAmaSy1 and CqUGT79B30-like1 in *N. benthamiana* leaves. Co-infiltration of transgenic *Agrobacterium* harboring plasmids for expressing the candidate genes with CqCYP76AD1-1, CqCDOPA5GT, CqDODA-1, and P19. CqUGT79B30-like1 is the closest homolog of the amaranthin synthetase cluster. The bar represents 4 cm.
Figure 9B:
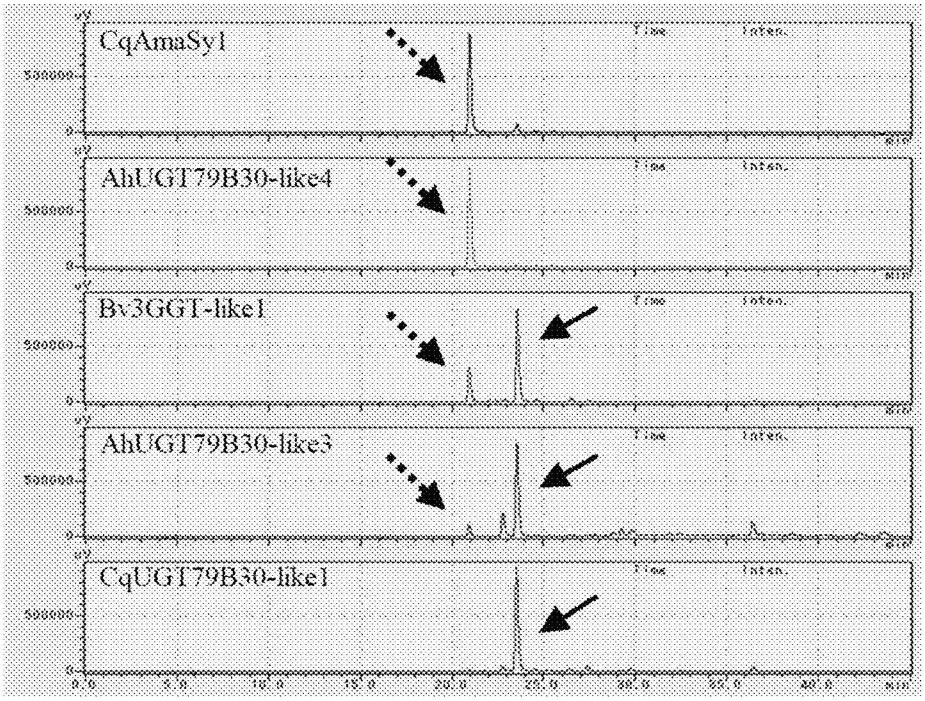
FIG. 9B includes HPLC chromatograms of infected *N. benthamiana* leaf extracts. Dashed and solid arrows indicate amaranthin and betanin, respectively. The horizontal axis indicates the retention time (min), and the vertical axis indicates the signal intensity (PV).

Also for those candidates, vectors were constructed (FIG. 8), and evaluation was performed with an expression system using *Nicotiana benthamiana*, and as a result, it was revealed that all the evaluated genes synthesized amaranthin (FIG. 9).

As apparent from the above-mentioned results, genes having an amaranthin synthesis ability were successfully isolated from *quinoa*. Further, it was revealed that such genes also existed in Amaranthaceae plants other than *quinoa.*

Example 2

[Analysis of Three-Dimensional Structure of Amaranthin Synthetase]

The three-dimensional structure analysis of a protein was performed on the basis of the amino acid sequence of amaranthin synthetase 1 of *quinoa.*

(Results)

Figure 10:
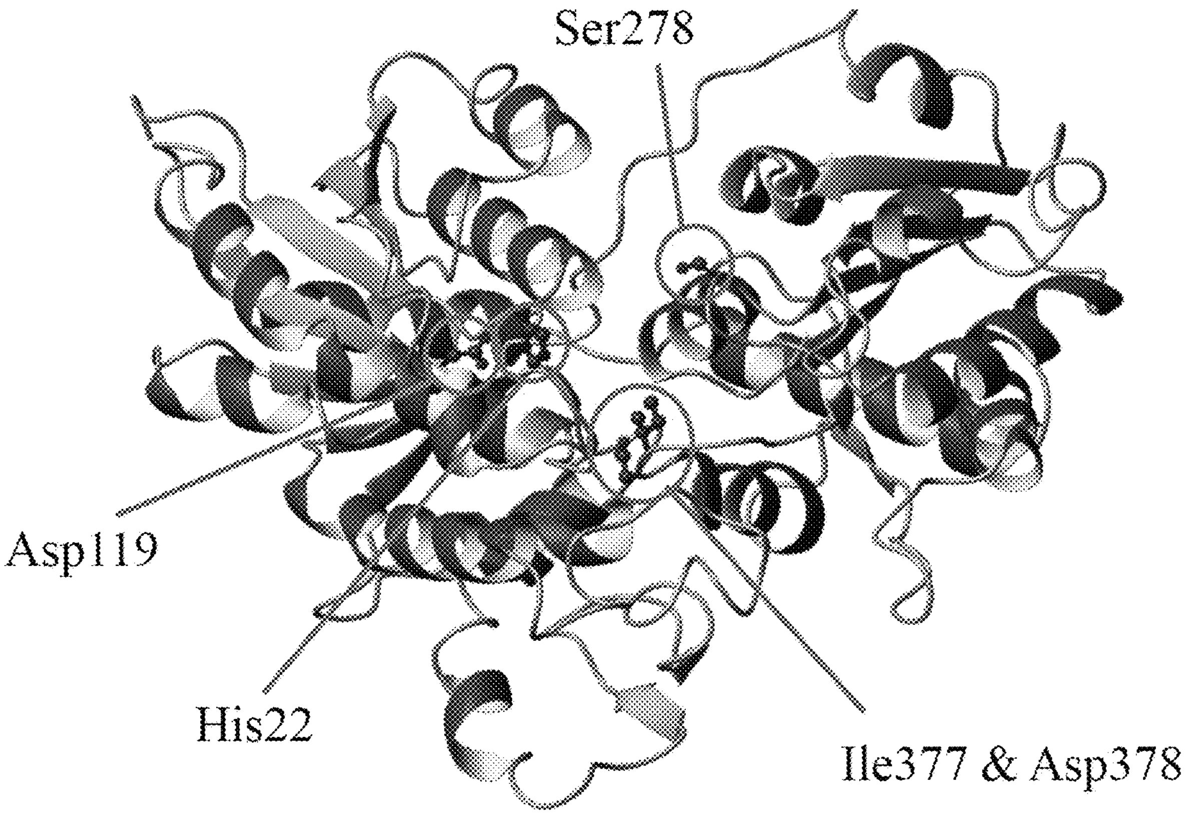
FIG. 10 is an illustration of the model structure of CqAmaSy1. The structure was calculated using coordinate 5NLM. The residues, expected to be responsible for the activity, are shown in ball-and-stick model.

It was predicted that five amino acid residues (His22, Asp119, Ser278, Ile377, and Asp378) were associated with enzyme activity (FIG. 10). Those amino acid residues were conserved in other amaranthin synthesizing proteins as well.

Example 3

[Analysis of Substrate for Amaranthin Synthetase]

Two pathways are predicted for amaranthin synthesis. One is a pathway in which glucuronic acid is bonded to betanin, and the other is a pathway in which glucuronic acid is bonded to cyclo-DOPA glucoside, followed by the bonding of betalamic acid through a spontaneous reaction (FIG. 1 and FIG. 2). Via which pathway the amaranthin synthetase isolated this time synthesized amaranthin was examined with an expression system using *Nicotiana benthamiana.*

Cyclo-DOPA 5-glucosyltransferase (cDOPA5GT), which is a gene used in a *Nicotiana benthamiana* expression system, can synthesize both of precursors (cyclo-DOPA 5-glucoside and betanin) of the two pathways. Accordingly, cDOPA5GT is not suited for identifying a constitutive pathway. In view of this, in order to synthesize only the precursor betanin, betanidin 5-glucosyltransferase (Betanidin-5GT) was used instead of cDOPA5GT for the *Nicotiana benthamiana* expression system (FIG. 8). The amaranthin synthetase gene was also simultaneously expressed in the expression system having incorporated therein Betanidin-5GT.

(Results)

Figure 11A:
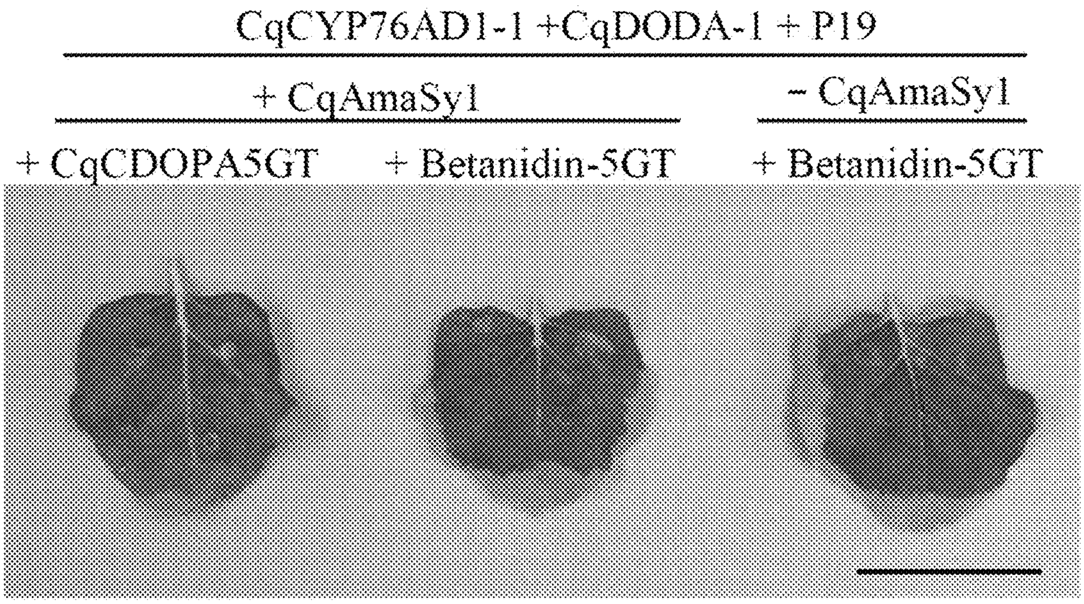
FIG. 11A: recombinant expression of CqCDOPA5GT or Cbbetanidin-5GT in *N. benthamiana* leaves. Co-infiltration of transgenic *Agrobacterium* harboring plasmids for CqCDOPA5GT or Cbbetanidin-5GT, expressing CqCYP76AD1-1, CqDODA-1, CqAmaSy1, and P19. −CqAmaSy1 functioned as a negative control. The bar represents 4 cm.
Figure 11B:
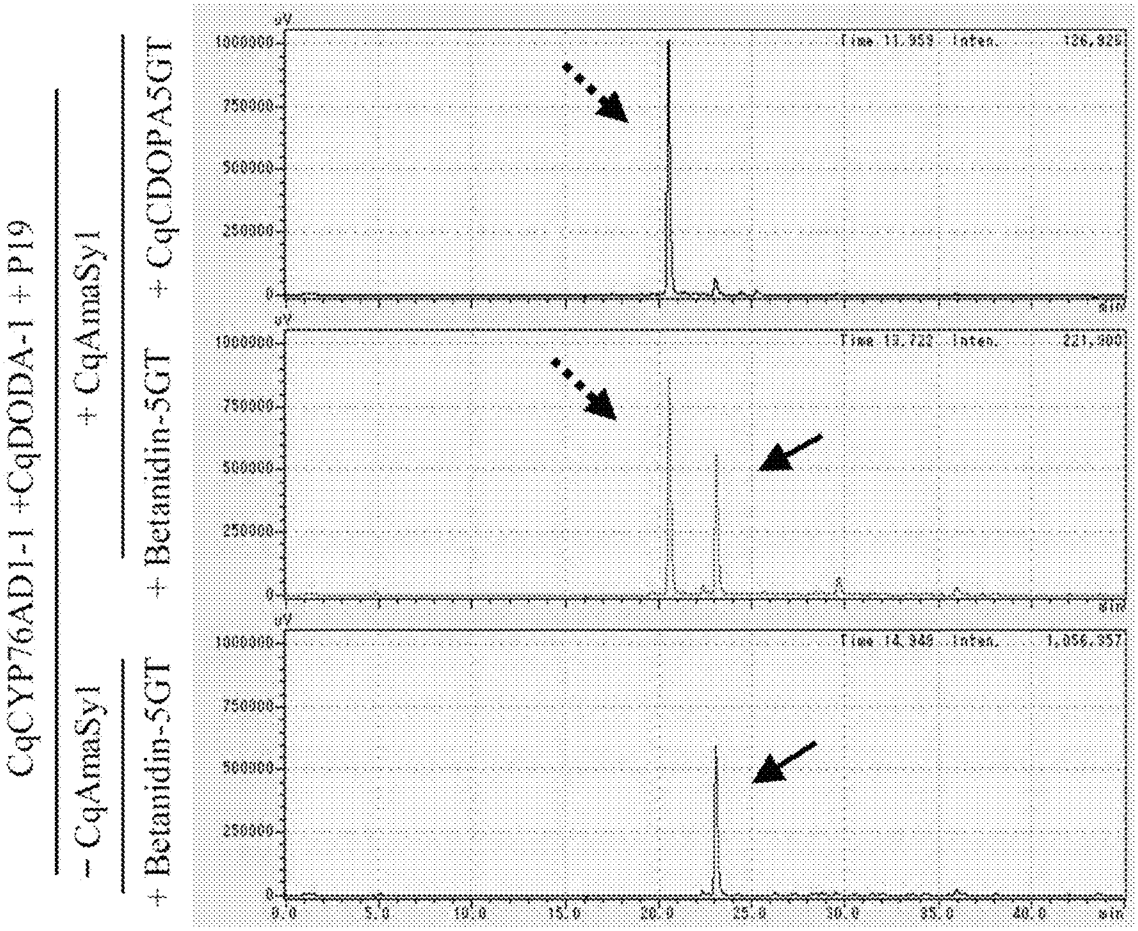
FIG. 11B includes HPLC chromatograms of infected *N. benthamiana* leaf extracts. Dashed and solid arrows indicate amaranthin and betanin, respectively. The horizontal axis indicates the retention time (min), and the vertical axis indicates the signal intensity (μV).

When the amaranthin synthetase gene was also simultaneously expressed in the expression system having incorporated therein Betanidin-5GT, the synthesis of amaranthin was recognized (FIG. 11). This result revealed that the amaranthin synthetase isolated this time possessed an ability to synthesize amaranthin by bonding glucuronic acid to betanin.

Example 4

[Mass Production of Amaranthin in Tobacco Cultured Cells (BY-2 Cells)]

The amaranthin synthetase gene was successfully isolated, and hence an attempt was made to mass produce amaranthin in tobacco BY-2 cells.

Figure 12:
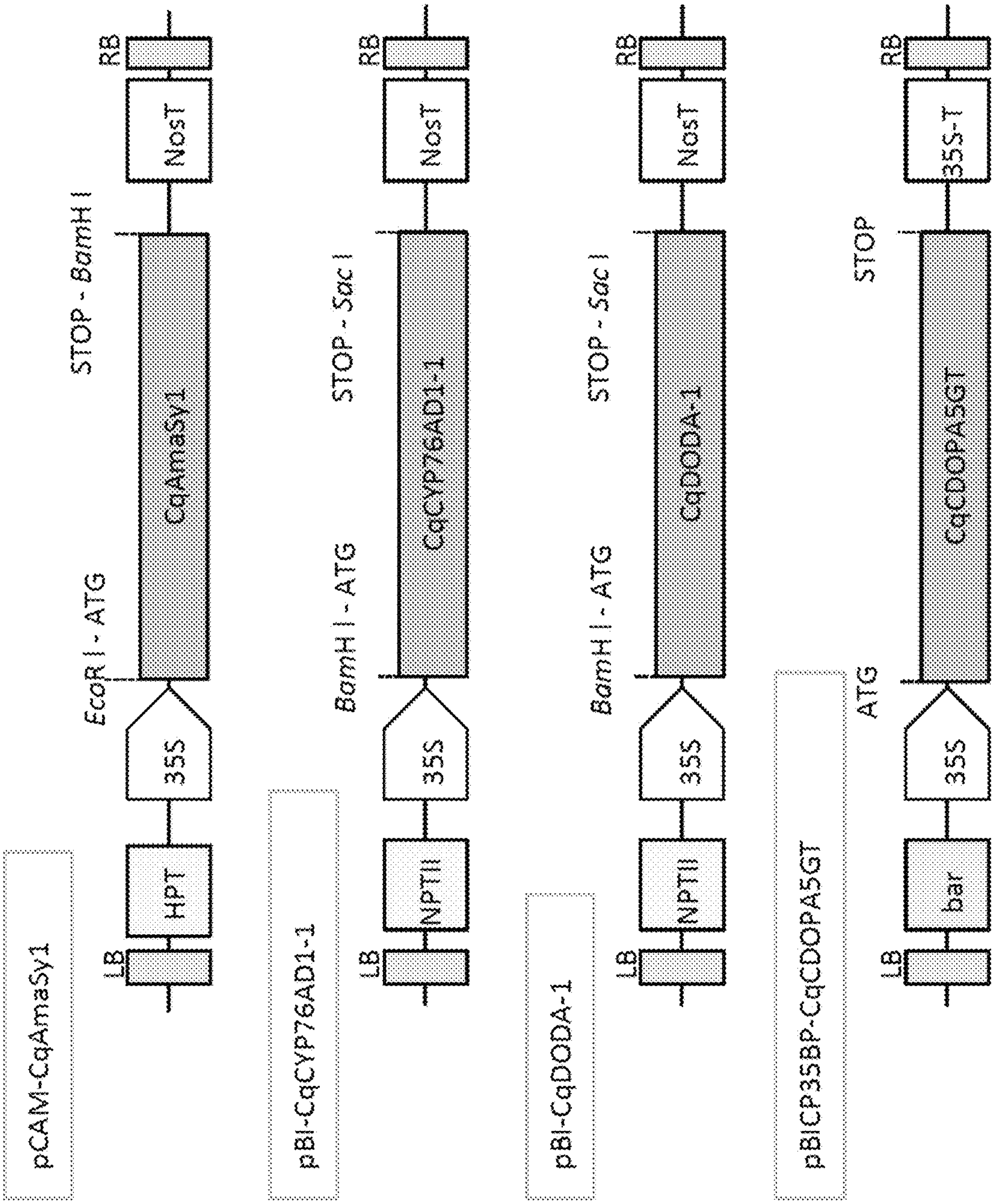
FIG. 12 includes schematic diagrams of plant expression vectors. CqAmaSy1 represents CqAmaSy1 CDS, CqCYP76AD1-1 represents CqCYP76AD1-1 CDS, CqDODA-1 represents CqDODA-1 CDS, CqCDOPA5GT represents qCDOPA5GT CDS, 35S represents a CaMV 35S promoter, NosT represents a nopaline synthase terminator, 35S-T represents a 35S terminator, RB represents a right border, and LB represents a left border. HPT represents a hygromycin phosphotransferase expression cassette, NPTII represents a neomycin phosphotransferase II expression cassette, bar represents a bar gene expression cassette, ATG represents a start codon, and STOP represents a stop codon.
Figure 13A:
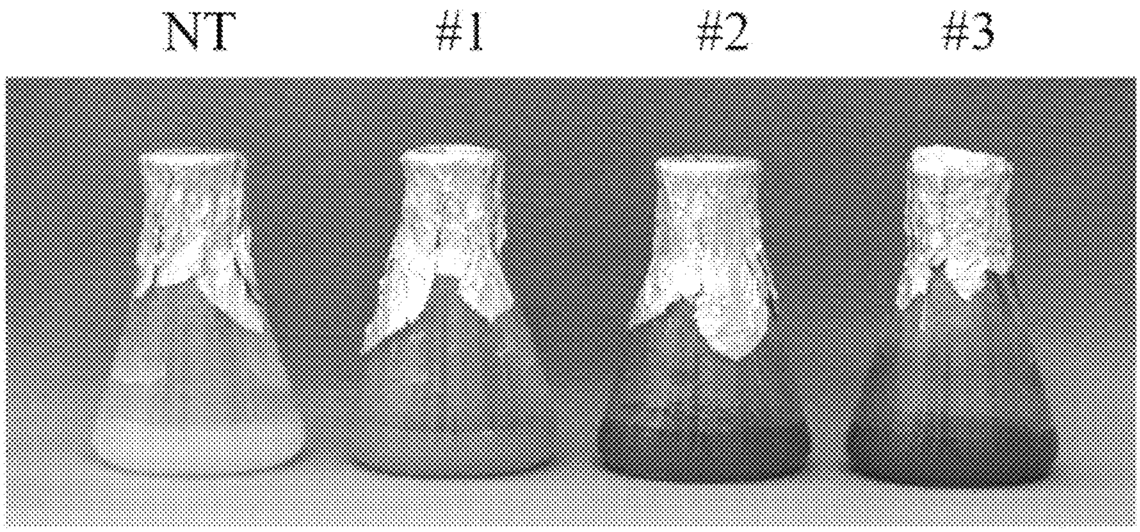
FIG. 13A is a photograph of transformed tobacco BY-2 cell lines. #1, #2, and #3 indicate transgenic tobacco BY-2 cell lines producing betanidin, betanin, and amaranthin, respectively. NT denotes the non-transgenic tobacco BY-2 cell line.
Figure 13B:
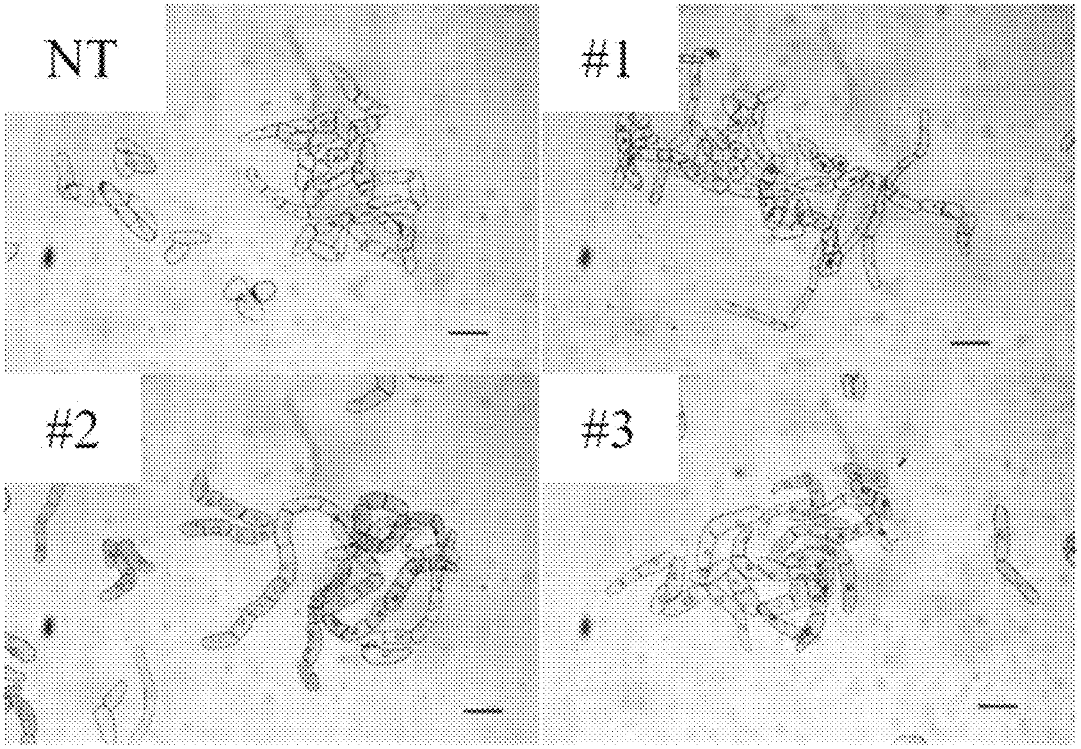
FIG. 13B includes photographs of the transformed tobacco BY-2 cells. Bars represent 100 μm.
Figure 13C:
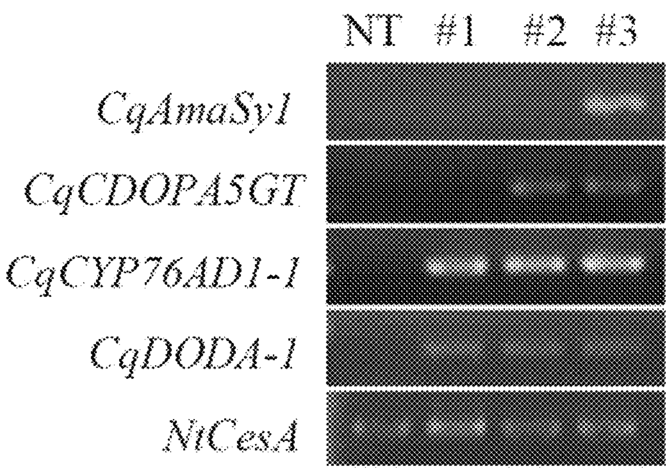
FIG. 13C: RT-PCR analysis of gene expression in the transformed tobacco BY-2 cells. NtCesA represents an internal control.
Figure 13D:
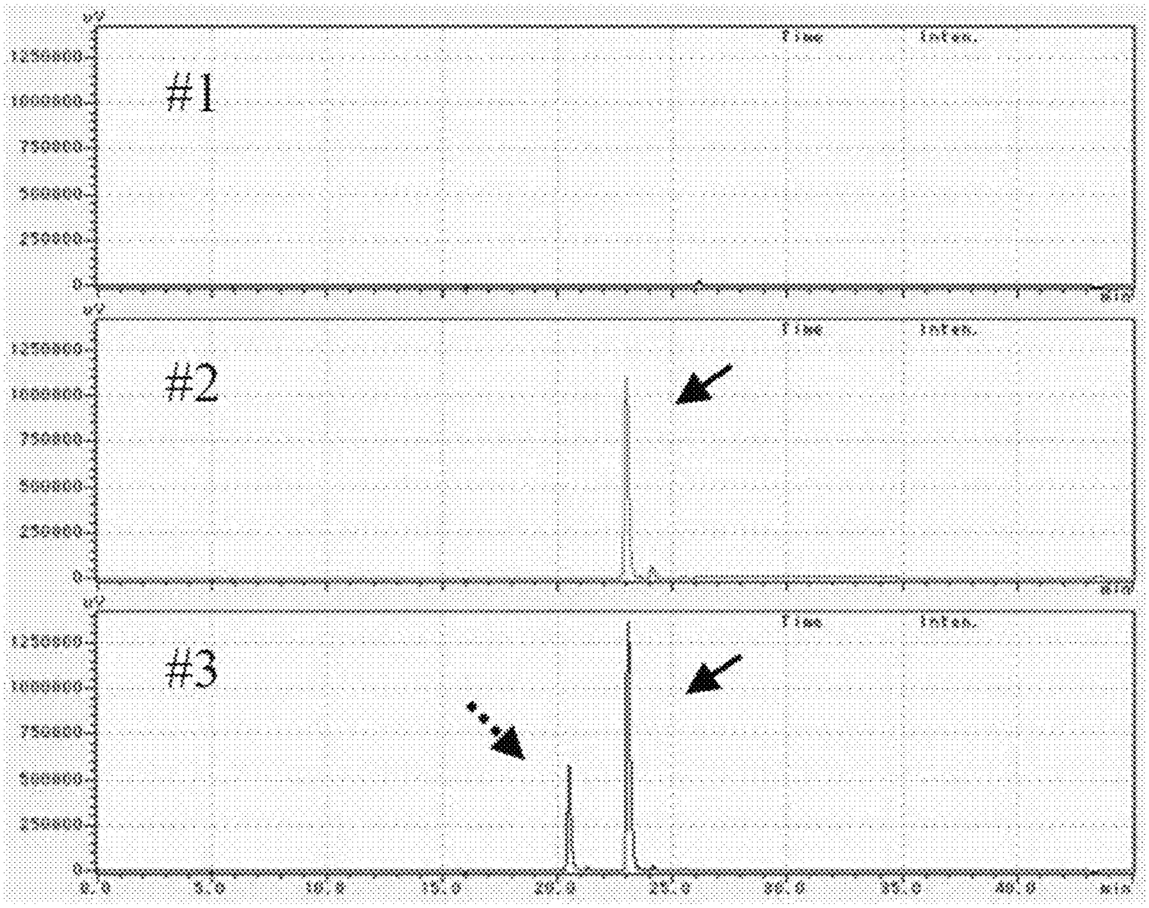
FIG. 13D includes HPLC chromatograms of the transformed tobacco BY-2 cell lines. Dashed and solid arrows indicate amaranthin and betanin, respectively. The horizontal axis indicates the retention time (min). The vertical axis indicates the signal intensity (μV).

In order to produce amaranthin, in accordance with the following method, vectors for expression in BY-2 cells were constructed (FIG. 12), and transformants having introduced therein four kinds of betalain biosynthesis genes (CqCYP76AD1-1, CqDODA-1, CqCDOPA5GT, and CqAmaSy1) were generated.

A strongly red line was selected from the resultant transformed BY-2 lines by the following method. At the same time with the production of the amaranthin-producing transformed line, a betanin-producing transformed line and a betanidin-producing transformed line were also generated and selected.

(Results)

The results of the generation and selection of the amaranthin-producing transformed line having introduced therein CqCYP76AD1-1, CqDODA-1, CqCDOPA5GT, and CqAmaSy1, the betanin-producing transformed line having introduced therein CqCYP76AD1-1, CqDODA-1, and CqCDOPA5GT, and the betanidin-producing transformed line having introduced therein CqCYP76AD1-1 and CqDODA-1 are shown in FIG. 13.

The three betalain-producing transformed lines thus selected were subjected to HPLC and mass spectrometry, and as a result, the production of amaranthin and betanin was recognized in the amaranthin-producing transformed line, and the production of betanin was recognized in the betanin-producing line. Meanwhile, in the betanidin-producing line, the production of betanidin was recognized.

For each transformed line, a betalain production amount in 150 mL culture were investigated. In the amaranthin-producing line, the amounts of amaranthin and betanin were 2.05±0.62 μmol and 3.99±0.23 μmol, respectively. In the betanin-producing line, betanin was produced in an amount of 2.93±1.29 μmol. In those transformed lines, the production of optical isomers such as isobetanin and isoamaranthin was not recognized.

According to this experiment, betalain pigments (amaranthin and betanin) can be mass produced in tobacco BY-2 cultured cells, i.e., a non-betalain-producing plant.

Example 5

[Influence of Betalain Pigment on Human Breast Cancer Cells]

It has been reported that a betanin/isobetanin mixture induces cell death of human breast cancer cells (MCF-7 cells) (Nowacki, L., Vigneron, P., Rotellini, L., Cazzola, H., Merlier, F., Prost, E., Ralanairina, R., Gadonna, J. P., Rossi, C. and Vayssade, M. (2015) Betanin-Enriched Red Beetroot (*Beta vulgaris* L.) Extract Induces Apoptosis and Autophagic Cell Death in MCF-7 Cells. Phytother. Res. 29, 1964-1973). In order to elucidate the physiological activity of amaranthin on the breast cancer cells, amaranthin and betanin produced in BY-2 cells were purified, and evaluated for their influences on the breast cancer cells.

(Results)

Figure 14A:
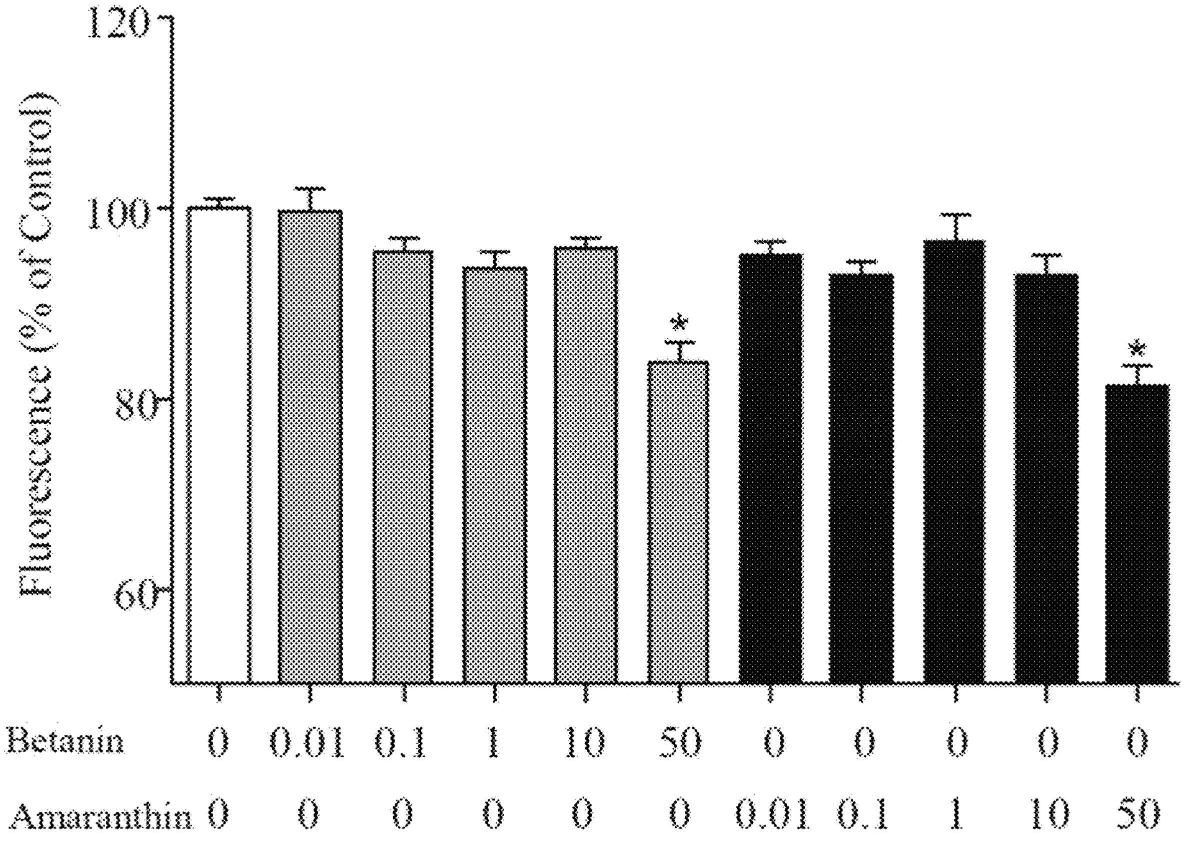
FIG. 14A: MCF-7 cells were cultured together with increasing concentrations of betanin or amaranthin (0.01 mM, 0.1 mM, 1 mM, 10 mM, and 50 mM) for 72 hours. Cell proliferation was determined using an AlamarBlue assay according to the manufacturer's instructions. Bars represent the mean±SE (n=5). Symbol "*" represents $p<0.05$ as compared to untreated cells.
Figure 14B:
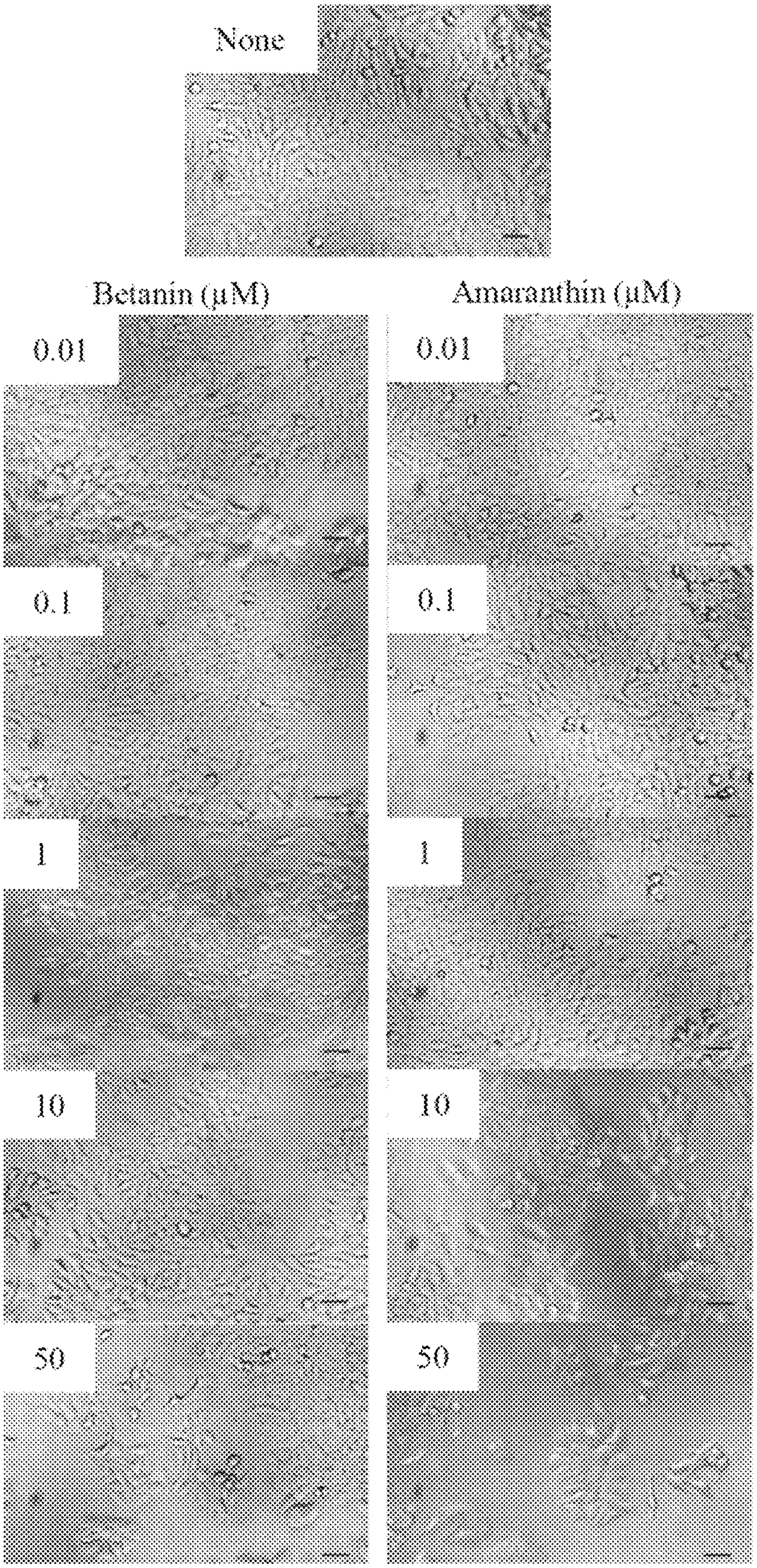
FIG. 14B shows the morphology of MCF-7 cells cultured for 72 hours with betanin or amaranthin. Cells were examined under an inverted microscope. Bars represent 100 μm.

It was revealed that both amaranthin and betanin significantly suppressed the cancer cell activity of the breast cancer cells at a concentration of 50 μM (FIG. 14).

Example 6

[Effect of Amaranthin on HIV-1 Protease Activity]

Amaranthin has been predicted by a virtual screening method to be a candidate of a novel HIV-1 protease inhibitor derived from a natural product (Yanuar, A., Suhartanto, H., Munim, A., Anugraha, B. H. and Syahdi, R. R. (2014) Virtual Screening of Indonesian Herbal Database as HIV-1 Protease Inhibitor. Bioinformation 10, 52-55). However, there is no report that amaranthin actually inhibits HIV-1 protease activity. In view of this, the inventors of the present invention used amaranthin and betanin produced in BY-2 cells to test whether these betalain pigments inhibited HIV-1 protease activity.

(Results)

Figure 15A:
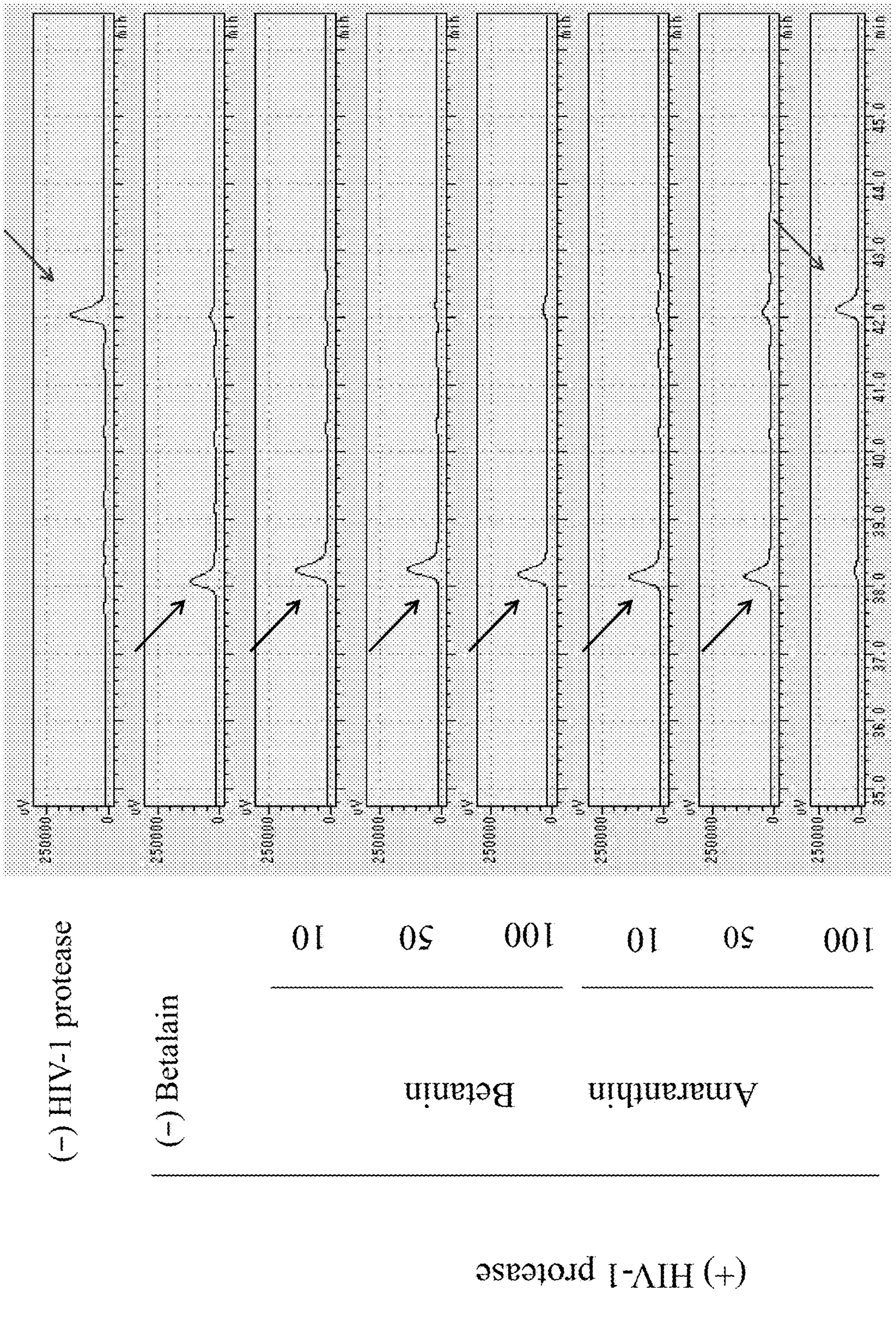
FIG. 15A includes HPLC chromatograms of HIV-1 protease reaction mixtures. Dashed and solid arrows indicate an HIV-1 protease substrate and its degradation product, respectively. (+) and (−)HIV-1 protease indicate reaction mixtures with and without the HIV-1 protease, respectively. (−)Betalain indicates a reaction mixture without betalain pigments. The horizontal axis indicates the retention time (min), and the vertical axis indicates the signal intensity (μV).
Figure 15B:
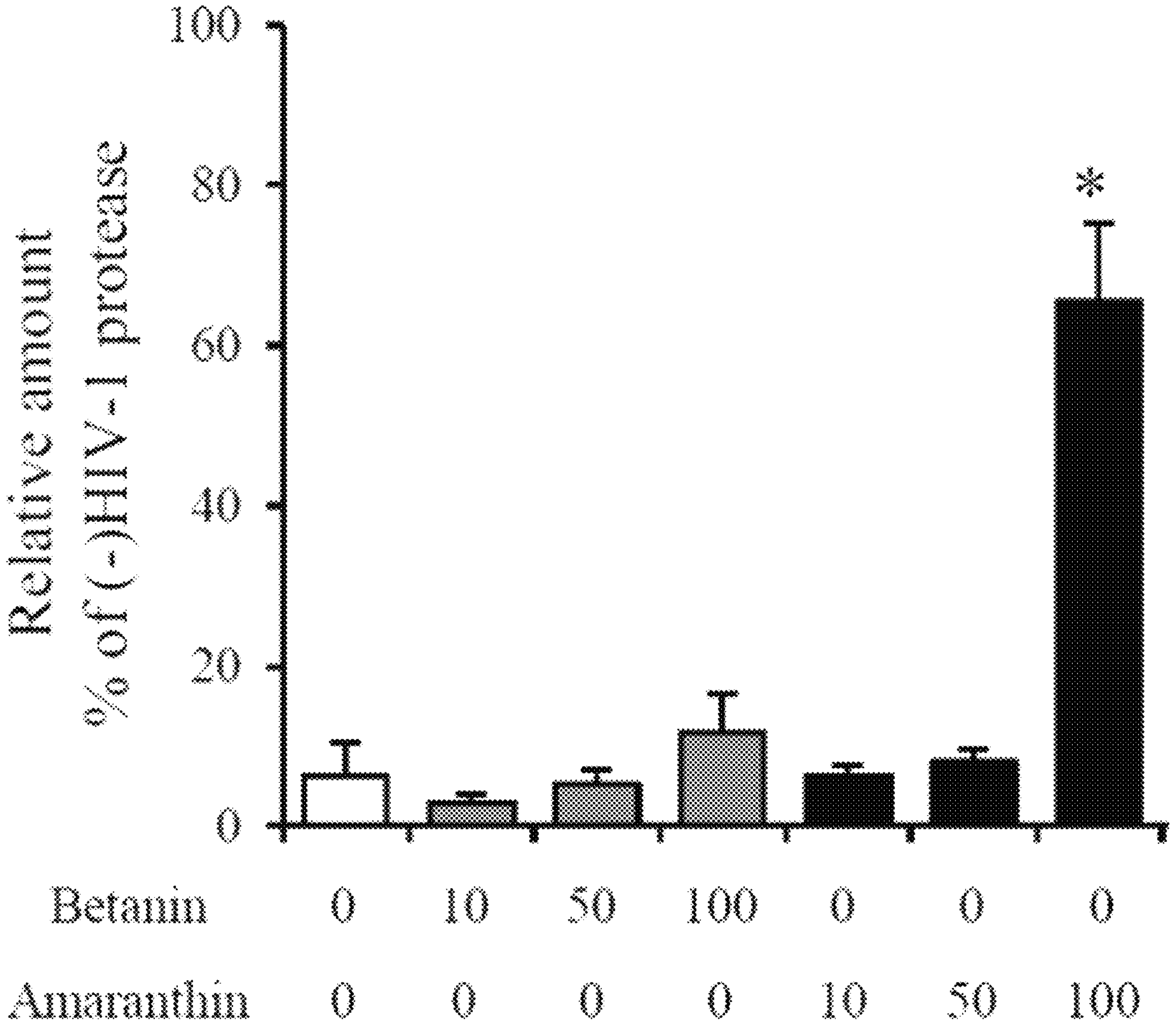
FIG. 15B shows the relative amounts of the HIV-1 substrate in the reaction mixtures. Gray and black bars indicate reaction mixtures containing betanin and amaranthin, respectively. The white bar indicates the reaction mixture without betalain pigments as a negative control. Bars represent the mean±SE (n=3). Symbol "*" represents $p<0.05$ as compared to the reaction mixture without betalain pigments. 0, 10, 50, and 100 indicate 0-, 10-, 50-, and 100-fold amounts of betalain as compared to the HIV-1 protease.

It was revealed that, when amaranthin was added in a 100-fold amount with respect to the HIV-1 protease, the activity of the HIV-1 protease was significantly inhibited (FIG. 15). Meanwhile, betanin was not found to have inhibitory activity on the HIV-1 protease (FIG. 15).

Example 7

[Recognition of Gomphrenin-I-O-Glucuronide Synthesis]

In order to recognize that the amaranthin synthetase of the present invention also has a gomphrenin-I-O-glucuronide synthetase action, with reference to the method of Example 1, a vector having incorporated therein CqAmaSy1 assumed to have a gomphrenin-I-O-glucuronide synthetase action was constructed (FIG. 17), and evaluation was performed with an expression system using *Nicotiana benthamiana.*

(Results)

Figure 17A:
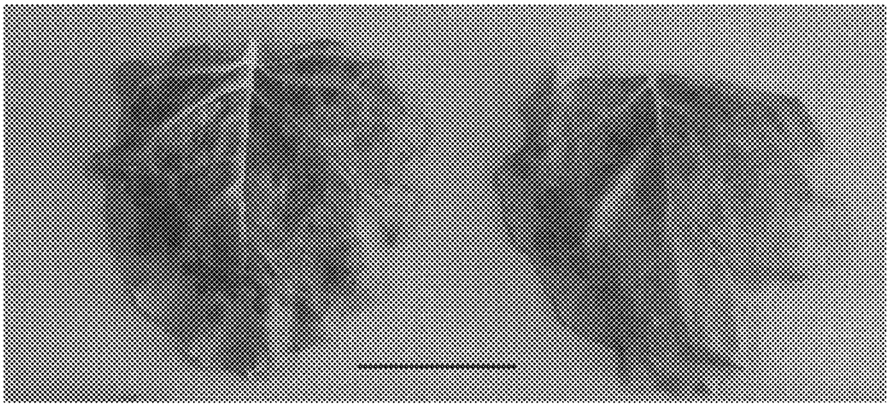
FIGS. 17A-B show the results of transient expression analysis using *Nicotiana benthamiana*. Co-infiltration of transgenic *Agrobacterium* harboring plasmids for expressing candidate genes with a gomphrenin-I-glucuronide synthetase gene (CqAmaSy1), CqCYP76AD1-1, DbB6GT, CqDODA-1, and P19 in *N. benthamiana* leaves. The bar represents 4 cm. HPLC chromatograms of infected *N. benthamiana* leaf extracts.
Figure 17B:
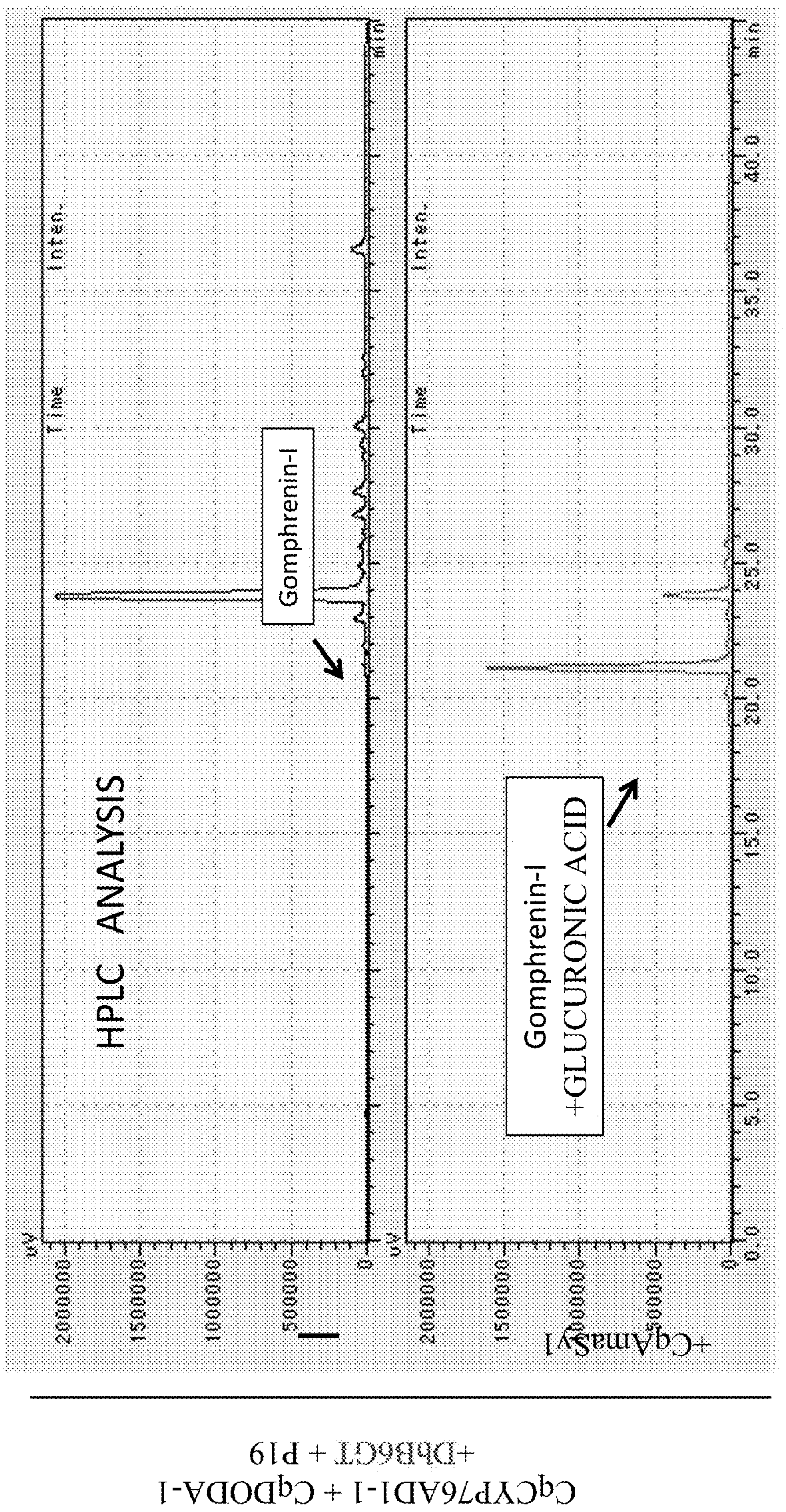

A red pigment produced in *Nicotiana benthamiana* was subjected to HPLC and MS analysis, and as a result, was revealed to have an ability to produce gomphrenin-I-glucuronide (FIGS. 17A-B).

Thus, it was recognized that the amaranthin synthetase of the present invention also had a gomphrenin-I-glucuronide synthetase action.

INDUSTRIAL APPLICABILITY

According to the present invention, the synthesis method for a betalain pigment, the amaranthin synthesis composition, the gomphrenin-I-glucuronide synthesis composition, and the betalain pigment-producing host can be provided.

The invention claimed is:

1. A synthesis method for a betalain pigment, comprising:

culturing a host that has introduced therein the following gene encoding an amaranthin synthetase or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding an enzyme having activity of glycosylating a phenolic hydroxy group, and a gene encoding an enzyme having DOPA 4,5-dioxygenase activity, and that has an ability to produce tyrosine or 3-hydroxy-L-tyrosine (L-DOPA), and extracting a betalain pigment from the host after the culturing, wherein the gene encoding an enzyme having activity of hydroxylating a 3-position of a phenol ring of tyrosine and the gene encoding an enzyme having L-DOPA oxidase activity is a single gene or different genes; or culturing a host that has introduced therein the following gene encoding an amaranthin synthetase or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding a betanidin-to-betanin synthetase, and a gene encoding an enzyme having DOPA 4,5-dioxygenase activity, and that has an ability to produce tyrosine or 3-hydroxy-L-tyrosine, and extracting a betalain pigment from the host after the culturing, wherein the gene encoding an enzyme having activity of hydroxylating a 3-position of a phenol ring of tyrosine and the gene encoding an enzyme having L-DOPA oxidase activity is a single gene or different genes; or culturing a host that has introduced therein the following gene encoding an amaranthin synthetase or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding a betanidin-to-gomphrenin-I (betanidin 6-O-glucoside) synthetase, and a gene encoding an enzyme having DOPA 4,5-dioxygenase activity, and that has an ability to produce tyrosine or 3-hydroxy-L-tyrosine, and extracting a betalain pigment from the host after the culturing, wherein the gene encoding an enzyme having activity of hydroxylating a 3-position of a phenol ring of tyrosine and the gene encoding an enzyme having L-DOPA oxidase activity is a single gene or different genes; or culturing a host that has introduced therein the following gene encoding an amaranthin synthetase or gomphrenin-I-glucuronide synthetase, and that has enzyme activity of having activity of hydroxylating a 3-position of a phenol ring of tyrosine, enzyme activity of having L-DOPA oxidase activity, enzyme activity of having activity of glycosylating a phenolic hydroxy group, enzyme activity of having DOPA 4,5-dioxygenase activity, and an ability to produce tyrosine or 3-hydroxy-L-tyrosine, and extracting a betalain pigment from the host after the culturing; or culturing a host that has introduced therein the following gene encoding an amaranthin synthetase or gomphrenin-I-glucuronide synthetase, and that has enzyme activity of having activity of hydroxylating a 3-position of a phenol ring of tyrosine, enzyme activity of having L-DOPA oxidase activity, enzyme activity of having betanidin-to-betanin synthesis activity, enzyme activity of having DOPA 4,5-dioxygenase activity, and an ability to produce tyrosine or 3-hydroxy-L-tyrosine, and extracting a betalain pigment from the host after the culturing; or culturing a host that has introduced therein the following gene encoding an amaranthin synthetase or gomphrenin-I-glucuronide synthetase, and that has enzyme activity of having activity of hydroxylating a 3-position of a phenol ring of tyrosine, enzyme activity of having L-DOPA oxidase activity, enzyme activity of having betanidin-to-gomphrenin-I synthesis activity, enzyme activity of having DOPA 4,5-dioxygenase activity, and an ability to produce tyrosine or 3-hydroxy-L-tyrosine, and extracting a betalain pigment from the host after the culturing, wherein, in the production method for a betalain pigment, the gene encoding an amaranthin synthetase or gomphrenin-I-glucuronide synthetase is any one or more selected from the following:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11; and (7) a gene formed of DNA having 90% or more homology to DNA formed of the base sequence set forth in SEQ ID NO: 1, 3, 5, 7, 9, or 11.

2. The synthesis method for a betalain pigment according to claim 1, wherein the betalain pigment is amaranthin.

3. The synthesis method for a betalain pigment according to claim 1, wherein the betalain pigment is gomphrenin-I-glucuronide.

4. The synthesis method for a betalain pigment according to claim 1, wherein the gene encoding an amaranthin synthetase or gomphrenin-I-glucuronide synthetase is any one or more selected from SEQ ID NOS: 1, 3, 5, 7, 9, and 11.

5. The synthesis method for a betalain pigment according to claim 2, wherein the gene encoding an amaranthin synthetase is any one or more selected from SEQ ID NOS: 1, 3, 5, 7, 9, and 11.

6. The synthesis method for a betalain pigment according to claim 3, wherein the gene encoding gomphrenin-I-glucuronide synthetase is any one or more selected from SEQ ID NOS: 1, 3, 5, 7, 9, and 11.

7. A betalain pigment-producing host having introduced therein a gene shown in any one of the following items (1) to (7) or a vector carrying the gene:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11; and (7) a gene formed of DNA having 90% or more homology to DNA formed of the base sequence set forth in SEQ ID NO: 1, 3, 5, 7, 9, or 11.

8. The betalain pigment-producing host according to claim 7, wherein the betalain pigment is amaranthin.

9. The betalain pigment-producing host according to claim 7, wherein the betalain pigment is gomphrenin-I-glucuronide.

10. A betalain pigment-producing host, the host having introduced therein the following gene encoding an amaranthin synthetase or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding an enzyme having activity of glycosylating a phenolic hydroxy group, and a gene encoding an enzyme having DOPA 4,5-dioxygenase activity, and having an ability to produce tyrosine or L-DOPA, wherein the gene encoding an enzyme having activity of hydroxylating a 3-position of a phenol ring of tyrosine and the gene encoding an enzyme having L-DOPA oxidase activity is a single gene or different genes, or the host having introduced therein the following gene encoding an amaranthin synthetase or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding a betanidin-to-betanin synthetase, and a gene encoding an enzyme having DOPA 4,5-dioxygenase activity, and having an ability to produce tyrosine or L-DOPA, wherein the gene encoding an enzyme having activity of hydroxylating a 3-position of a phenol ring of tyrosine and the gene encoding an enzyme having L-DOPA oxidase activity is a single gene or different genes, or the host having introduced therein the following gene encoding an amaranthin synthetase or gomphrenin-I-glucuronide synthetase, a gene encoding an enzyme having activity of hydroxylating a 3-position of a phenol ring of tyrosine, a gene encoding an enzyme having L-DOPA oxidase activity, a gene encoding an enzyme having betanidin-to-gomphrenin-I synthesis activity, and a gene encoding an enzyme having DOPA 4,5-dioxygenase activity, and having an ability to produce tyrosine or L-DOPA, wherein the gene encoding an enzyme having activity of hydroxylating a 3-position of a phenol ring of tyrosine and the gene encoding an enzyme having L-DOPA oxidase activity is a single gene or different genes, or the host having introduced therein the following gene encoding an amaranthin synthetase or gomphrenin-I-glucuronide synthetase, and having enzyme activity of having activity of hydroxylating a 3-position of a phenol ring of tyrosine, enzyme activity of having L-DOPA oxidase activity, enzyme activity of having activity of glycosylating a phenolic hydroxy group, enzyme activity of having DOPA 4,5-dioxygenase activity, and an ability to produce tyrosine or 3-hydroxy-L-tyrosine, or the host having introduced therein the following gene encoding an amaranthin synthetase or gomphrenin-I-glucuronide synthetase, and having enzyme activity of having activity of hydroxylating a 3-position of a phenol ring of tyrosine, enzyme activity of having L-DOPA oxidase activity, enzyme activity of having betanidin-to-betanin synthesis activity, enzyme activity of having DOPA 4,5-dioxygenase activity, and an ability to produce tyrosine or 3-hydroxy-L-tyrosine, or the host having introduced therein the following gene encoding an amaranthin synthetase or gomphrenin-I-glucuronide synthetase, and having enzyme activity of having activity of hydroxylating a 3-position of a phenol ring of tyrosine, enzyme activity of having L-DOPA oxidase activity, enzyme activity of having betanidin-to-gomphrenin-I synthesis activity, enzyme activity of having DOPA 4,5-dioxygenase activity, and an ability to produce tyrosine or 3-hydroxy-L-tyrosine, wherein the gene encoding an amaranthin synthetase or gomphrenin-I-glucuronide synthetase is any one or more selected from the following:

(1) a gene encoding a polypeptide formed of an amino acid sequence set forth in SEQ ID NO: 2, 4, 6, 8, 10, or 12;

(2) a gene encoding a polypeptide that has 1 to 20 amino acids substituted, deleted, inserted, and/or added in the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(3) a gene encoding a polypeptide that has 90% or more homology to the amino acid sequence set forth in SEQ ID NO: 2, 4, 6, 8, 10, or 12, and that has a substantially equivalent ability to synthesize amaranthin or gomphrenin-I-glucuronide to that of the amino acid sequence set forth in SEQ ID NO: 2, 4, 6, 8, 10, or 12;

(4) a gene formed of DNA formed of a base sequence set forth in SEQ ID NO: 1, 3, 5, 7, 9, or 11;

(5) a gene formed of DNA that hybridizes with DNA formed of a base sequence complementary to DNA formed of the base sequence set forth in SEQ ID NO: 1, 3, 5, 7, 9, or 11 under stringent conditions, and that encodes a polypeptide having an ability to synthesize amaranthin or gomphrenin-I-glucuronide;

(6) a gene formed of DNA having a 1- to 50-base sequence substituted, deleted, inserted, and/or added in DNA formed of the base sequence set forth in SEQ ID NO: 1, 3, 5, 7, 9, or 11; and (7) a gene formed of DNA having 90% or more homology to DNA formed of the base sequence set forth in SEQ ID NO: 1, 3, 5, 7, 9, or 11.

11. The betalain pigment-producing host according to claim 10, wherein the betalain pigment is amaranthin.

12. The betalain pigment-producing host according to claim 10, wherein the betalain pigment is gomphrenin-I-glucuronide.

13. The betalain pigment-producing host according to claim 10, wherein the gene encoding an amaranthin synthetase or gomphrenin-I-glucuronide synthetase is any one or more selected from SEQ ID NOS: 1, 3, 5, 7, 9, and 11.

14. The betalain pigment-producing host according to claim 11, wherein the gene encoding an amaranthin synthetase is any one or more selected from SEQ ID NOS: 1, 3, 5, 7, 9, and 11.

15. The betalain pigment-producing host according to claim 12, wherein the gene encoding gomphrenin-I-glucuronide synthetase is any one or more selected from SEQ ID NOS: 1, 3, 5, 7, 9, and 11.

* * * * *